(12) United States Patent
Carson et al.

(10) Patent No.: US 9,443,370 B2
(45) Date of Patent: Sep. 13, 2016

(54) METHOD AND APPARATUS FOR ONSITE DISTRIBUTION OF MEDICATIONS AND MEDICAL SUPPLIES

(71) Applicant: Omnicare, Inc., Cincinnati, OH (US)

(72) Inventors: Bradley E. Carson, Ottawa Hills, OH (US); Michael J. Szesko, Freehold, NJ (US)

(73) Assignee: Omnicare, Inc., Cincinnati, OH (US)

( * ) Notice: Subject to any disclaimer, the term of this patent is extended or adjusted under 35 U.S.C. 154(b) by 630 days.

(21) Appl. No.: 13/801,944

(22) Filed: Mar. 13, 2013

(65) Prior Publication Data

US 2013/0253700 A1  Sep. 26, 2013

Related U.S. Application Data

(60) Provisional application No. 61/615,711, filed on Mar. 26, 2012.

(51) Int. Cl.

| G07F 11/54 | (2006.01) |
|---|---|
| G07F 9/00 | (2006.01) |
| G07F 17/00 | (2006.01) |
| G06F 19/00 | (2011.01) |

(52) U.S. Cl.
CPC ............ G07F 9/006 (2013.01); G07F 11/54 (2013.01); G07F 17/0092 (2013.01); *G06F 19/3462* (2013.01)

(58) Field of Classification Search
CPC ..... G07F 17/0092; G07F 9/006; G07F 11/54
See application file for complete search history.

(56) References Cited

U.S. PATENT DOCUMENTS

| 3,917,045 A | 11/1975 | Williams et al. |
|---|---|---|
| 4,267,942 A | 5/1981 | Wick, Jr. et al. |
| 4,519,522 A | 5/1985 | McElwee |
| 4,546,901 A | 10/1985 | Buttarazzi |
| 4,635,053 A | 1/1987 | Banks et al. |
| 4,664,289 A | 5/1987 | Shimizu et al. |
| 4,674,652 A | 6/1987 | Aten et al. |
| 4,695,954 A | 9/1987 | Rose et al. |
| 4,737,910 A | 4/1988 | Kimbrow |
| 4,785,969 A | 11/1988 | McLaughlin |
| 4,811,764 A | 3/1989 | McLaughlin |
| 4,839,806 A | 6/1989 | Goldfischer et al. |

(Continued)

OTHER PUBLICATIONS

D2, RoboCrib, pp. 1-6, Jan. 2010.†

(Continued)

*Primary Examiner* — Timothy Waggoner
(74) *Attorney, Agent, or Firm* — Wood, Herron & Evans, LLP

(57) ABSTRACT

Secure access distribution machines and methods for distributing a plurality of medical items to an authorized user. The distribution machine includes a housing enclosing a plurality of bins for storing medical items mounted on carousels. Once the distribution machine has been provided with user identification data, patient identification data, and an item selection, the plurality of carousels is actuated to move a bin holding a selected medical item to a location behind an access door in the housing. The user can then reach into the housing to manually retrieve and then verify the removal of the selected medical item. Only one access door into the housing is opened at any time, thereby preventing unauthorized removal of medical items stored in any other bins within the housing.

17 Claims, 36 Drawing Sheets

(56) References Cited

U.S. PATENT DOCUMENTS

| | | | |
|---|---|---|---|
| 4,847,764 | A | 7/1989 | Halvorson |
| 4,967,928 | A | 11/1990 | Carter |
| 5,014,875 | A * | 5/1991 | McLaughlin ........ G07F 17/0092 221/122 |
| 5,190,185 | A | 3/1993 | Blechl |
| 5,225,825 | A | 7/1993 | Warren |
| 5,292,029 | A | 3/1994 | Pearson |
| 5,313,393 | A | 5/1994 | Varley et al. |
| 5,314,243 | A | 5/1994 | McDonald et al. |
| 5,337,919 | A | 8/1994 | Spaulding et al. |
| 5,337,920 | A * | 8/1994 | Clausen ................. G07F 11/54 700/243 |
| 5,377,864 | A | 1/1995 | Blechl et al. |
| 5,390,711 | A | 2/1995 | Murphey |
| 5,392,951 | A | 2/1995 | Gardner et al. |
| 5,438,523 | A | 8/1995 | Humm et al. |
| 5,441,165 | A | 8/1995 | Kemp et al. |
| 5,502,944 | A | 4/1996 | Kraft et al. |
| 5,520,450 | A | 5/1996 | Colson, Jr. et al. |
| 5,608,643 | A | 3/1997 | Wichter et al. |
| 5,671,592 | A | 9/1997 | Yuyama et al. |
| 5,713,485 | A | 2/1998 | Liff et al. |
| 5,720,154 | A | 2/1998 | Lasher et al. |
| 5,790,409 | A | 8/1998 | Fedor et al. |
| 5,797,515 | A | 8/1998 | Liff et al. |
| 5,799,787 | A | 9/1998 | Talbot |
| 5,805,456 | A | 9/1998 | Higham et al. |
| 5,844,808 | A | 12/1998 | Konsmo et al. |
| 5,848,593 | A | 12/1998 | McGrady et al. |
| 5,852,911 | A | 12/1998 | Yuyama et al. |
| 5,896,298 | A | 4/1999 | Richter |
| 5,905,653 | A | 5/1999 | Higham et al. |
| 5,907,493 | A | 5/1999 | Boyer et al. |
| 5,912,818 | A * | 6/1999 | McGrady ............ G07F 17/0092 700/214 |
| 5,971,593 | A | 10/1999 | McGrady |
| 5,971,594 | A | 10/1999 | Sahai et al. |
| 5,993,046 | A | 11/1999 | McGrady et al. |
| 6,003,006 | A | 12/1999 | Colella et al. |
| 6,019,249 | A | 2/2000 | Michael et al. |
| 6,039,467 | A | 3/2000 | Holmes |
| 6,056,150 | A | 5/2000 | Kasper |
| 6,068,156 | A | 5/2000 | Liff et al. |
| 6,073,834 | A | 6/2000 | Michael et al. |
| 6,112,502 | A * | 9/2000 | Frederick ............ G06F 19/3462 221/10 |
| 6,163,737 | A | 12/2000 | Fedor et al. |
| 6,175,779 | B1 | 1/2001 | Barrett |
| 6,237,806 | B1 | 5/2001 | Sala et al. |
| 6,338,007 | B1 | 1/2002 | Broadfield et al. |
| 6,405,893 | B1 | 6/2002 | Tobe et al. |
| 6,438,451 | B1 | 8/2002 | Lion |
| 6,462,644 | B1 | 10/2002 | Howell et al. |
| 6,464,142 | B1 * | 10/2002 | Denenberg ........... G07F 17/0092 235/440 |
| 6,470,234 | B1 | 10/2002 | McGrady |
| 6,471,089 | B2 | 10/2002 | Liff et al. |
| 6,564,121 | B1 | 5/2003 | Wallace et al. |
| 6,581,798 | B2 | 6/2003 | Liff et al. |
| 6,604,019 | B2 | 8/2003 | Ahlin et al. |
| 6,650,964 | B2 | 11/2003 | Spano, Jr. et al. |
| 6,671,579 | B2 | 12/2003 | Spano, Jr. et al. |
| 6,694,217 | B2 | 2/2004 | Bloom |
| 6,697,704 | B2 | 2/2004 | Rosenblum |
| 6,715,267 | B2 | 4/2004 | Schaefer et al. |
| 6,735,497 | B2 | 5/2004 | Wallace et al. |
| 6,760,643 | B2 | 7/2004 | Lipps |
| 6,814,254 | B2 | 11/2004 | Liff et al. |
| 6,814,255 | B2 | 11/2004 | Liff et al. |
| 6,850,815 | B1 | 2/2005 | Veenstra |
| 6,874,684 | B1 | 4/2005 | Denenberg et al. |
| 6,975,922 | B2 | 12/2005 | Duncan et al. |
| 7,080,755 | B2 | 7/2006 | Handfield et al. |
| 7,086,558 | B1 * | 8/2006 | Pixley ................ G07F 17/0042 221/2 |
| 7,093,755 | B2 | 8/2006 | Jordan et al. |
| 7,147,107 | B2 | 12/2006 | Haggard et al. |
| 7,151,982 | B2 | 12/2006 | Liff et al. |
| 7,228,200 | B2 | 6/2007 | Baker et al. |
| 7,263,410 | B1 | 8/2007 | Frederick et al. |
| 7,263,411 | B2 | 8/2007 | Shows et al. |
| 7,286,900 | B1 | 10/2007 | Frederick et al. |
| 7,336,174 | B1 | 2/2008 | Maloney |
| 7,349,858 | B1 | 3/2008 | McGrady et al. |
| 7,447,563 | B2 | 11/2008 | Dobos |
| 7,467,093 | B1 | 12/2008 | Newton et al. |
| 7,469,820 | B2 | 12/2008 | Rosenblum |
| 7,493,190 | B1 | 2/2009 | Tomassi |
| 7,502,666 | B2 | 3/2009 | Siegel et al. |
| 7,588,165 | B2 | 9/2009 | Prichard et al. |
| 7,630,788 | B1 | 12/2009 | Reese |
| 7,630,790 | B2 | 12/2009 | Handfield et al. |
| 7,630,791 | B2 | 12/2009 | Nguyen et al. |
| 7,676,299 | B2 | 3/2010 | Clarke et al. |
| 7,689,316 | B1 * | 3/2010 | Frederick ............ G06F 19/327 700/231 |
| 7,689,317 | B2 | 3/2010 | McGrady et al. |
| 7,698,019 | B2 | 4/2010 | Moncrief et al. |
| 7,719,420 | B2 | 5/2010 | Christie et al. |
| 7,735,680 | B2 | 6/2010 | Godlewski |
| 7,735,683 | B2 | 6/2010 | Handfield et al. |
| 7,747,347 | B2 | 6/2010 | Park, IV |
| 7,751,932 | B1 | 7/2010 | Fedor et al. |
| 7,840,307 | B2 | 11/2010 | Mauger et al. |
| 7,860,603 | B2 | 12/2010 | Handfield et al. |
| 7,860,605 | B2 | 12/2010 | Frankel |
| 7,861,495 | B2 | 1/2011 | Yuyama et al. |
| 7,865,263 | B2 | 1/2011 | Spano, Jr. et al. |
| 7,886,931 | B2 | 2/2011 | Handfield et al. |
| 7,889,330 | B2 | 2/2011 | Newcomb |
| 7,912,578 | B1 | 3/2011 | Frankel |
| 7,925,375 | B2 | 4/2011 | Schininger et al. |
| 7,949,426 | B2 | 5/2011 | Handfield et al. |
| 7,991,507 | B2 | 8/2011 | Liff et al. |
| 7,996,105 | B2 | 8/2011 | Handfield et al. |
| 8,025,228 | B2 | 9/2011 | Dearing et al. |
| 8,068,934 | B2 | 11/2011 | Saltsov |
| 8,090,471 | B2 | 1/2012 | Shows et al. |
| 8,090,472 | B2 | 1/2012 | Schifman et al. |
| 8,145,351 | B2 | 3/2012 | Schininger et al. |
| 8,180,484 | B2 | 5/2012 | Baker et al. |
| 8,380,535 | B2 | 2/2013 | Fellows et al. |
| 8,442,676 | B2 * | 5/2013 | Kobayashi ............ A47F 3/0404 221/119 |
| 9,117,016 | B2 * | 8/2015 | Carson ................ G06F 19/3462 |
| 2003/0146233 | A1 | 8/2003 | Chirnomas |
| 2004/0210341 | A1 | 10/2004 | Wallace et al. |
| 2005/0023286 | A1 * | 2/2005 | Pinney ................ G06F 19/3462 221/123 |
| 2005/0113969 | A1 * | 5/2005 | Spano, Jr. ............ G06F 19/3462 700/237 |
| 2005/0216120 | A1 * | 9/2005 | Rosenberg ............ G07F 11/54 700/244 |
| 2006/0079994 | A1 | 4/2006 | Chu et al. |
| 2006/0102646 | A1 * | 5/2006 | Godlewski ........... A47B 49/004 221/76 |
| 2007/0043469 | A1 * | 2/2007 | Draper ................ G06F 19/3462 700/231 |
| 2007/0088461 | A1 | 4/2007 | Haitin et al. |
| 2008/0029601 | A1 * | 2/2008 | Clarke .................... G07F 11/54 235/462.01 |
| 2009/0014458 | A1 | 1/2009 | Heffron |
| 2010/0004782 | A1 | 1/2010 | Siegel et al. |
| 2010/0017296 | A1 | 1/2010 | Spignesi, Jr. et al. |
| 2010/0042437 | A1 | 2/2010 | Levy et al. |
| 2012/0012606 | A1 | 1/2012 | Longley et al. |
| 2012/0116579 | A1 | 5/2012 | Shows et al. |

OTHER PUBLICATIONS

D1, RoboCrib, pp. 1-6, Sep. 2006.†

\* cited by examiner
† cited by third party

FIG. 17E

RESIDENT: [▼] 1 of 12

RESIDENT: PATIENT1, TEST
NUMBER: 111111
ROOM: CA 001 A FAT TEST
PHYSICIAN: DOCTOR1, TEST

VERIFY RESIDENT
INFORMATION HERE

DATE: DECEMBER 20, 2012 20:12
USER: USER, ADMIN
SEX: M
DOB: 19120101
SSN: 111111111
ALLERGIES:

PRESS THIS BUTTON TO DISPLAY ITEMS

[CLOSE] [CANCEL] [MAINT] [FAX] [DETAILS] [ENTER]

| Y/N | QTY | QOH | SCHED | | PRODUCT NAME | STRENGTH | FORM |
|---|---|---|---|---|---|---|---|
| ☐ | 0 | 1 | NP | 2 | BRANDNAME1 | 10 MG | GEL |
| ☐ | 0 | 4 | NP | 2 | BRANDNAME1 | 10 MG | GEL |
| ☐ | 0 | 1 | NP | 2 | BRANDNAME1 | 10 MG | GEL |
| ☐ | 0 | 9 | NP | 3 | DEA TESTDRUG1 BNAME 1G TAB | 1 G | TAB |
| ☐ | 0 | 8 | NP | 3 | DEA TESTDRUG1 BNAME 10MG TAB | 10 G | TAB |
| ☐ | 0 | 10 | NP | 3 | DEA TESTDRUG1 BNAME 2MG TAB | 2 G | TAB |
| ☐ | 0 | 10 | NP | 3 | DEA TESTDRUG1 BNAME 3MG TAB | 3 G | TAB |
| ☐ | 0 | 10 | NP | 3 | DEA TESTDRUG1 BNAME 4MG TAB | 4 G | TAB |
| ☐ | 0 | 7 | NP | 3 | DEA TESTDRUG1 BNAME 5MG TAB | 5 G | TAB |

Tabs: PROFILED / NON PROFILED | BRAND / GENERIC | REVIEW | ISSUE

Buttons: CLOSE | CANCEL | MAINT | FAX | DETAILS | ENTER

FIG. 17H

| Y/N | QTY | QOH | SCHED | PRODUCT NAME | STRENGTH | FORM |
|---|---|---|---|---|---|---|
| ☐ | 0 | 1 | NP 2 | BRANDNAME1 | 10 MG | GEL |
| ☐ | 0 | 4 | NP 2 | BRANDNAME1 | 10 MG | GEL |
| ☐ | 0 | 1 | NP 2 | BRANDNAME1 | 10 MG | GEL |
| ☐ | 0 | 9 | NP 3 | DEA TESTDRUG1 BNAME 1G TAB | 1 G | TAB |
| ☐ | 0 | 8 | NP 3 | DEA TESTDRUG1 BNAME 10MG TAB | 10 G | TAB |
| ☐ | 0 | 10 | NP 3 | DEA TESTDRUG1 BNAME 2MG TAB | 2 G | TAB |
| ☐ | 0 | 10 | NP 3 | DEA TESTDRUG1 BNAME 3MG TAB | 3 G | TAB |
| ☐ | 0 | 10 | NP 3 | DEA TESTDRUG1 BNAME 4MG TAB | 4 G | TAB |
| ☐ | 0 | 7 | NP 3 | DEA TESTDRUG1 BNAME 5MG TAB | 5 G | TAB |

Buttons: PROFILED/ NON PROFILED | BRAND/ GENERIC | REVIEW | ISSUE
CLOSE | CANCEL | MAINT | FAX | DETAILS | ENTER

FIG. 17I

| Y/N | QTY | QOH | SCHED | PRODUCT NAME | STRENGTH | FORM |
|---|---|---|---|---|---|---|
| ☐ | 0 | 1 | NP 2 | TIMETEST | 10 MG | GEL |
| ☐ | 0 | 4 | NP 2 | TIMETEST2 | 10 MG | GEL |
| ☐ | 0 | 1 | NP 2 | TIMETEST3 | 10 MG | GEL |
| ☐ | 0 | 9 | NP 3 | DEA TESTDRUG1 BNAME 1G TAB | 1 G | TAB |
| ☐ | 0 | 8 | NP 3 | DEA TESTDRUG1 BNAME 10MG TAB | 10 G | TAB |
| ☐ | 0 | 10 | NP 3 | DEA TESTDRUG1 BNAME 2MG TAB | 2 G | TAB |
| ☐ | 0 | 10 | NP 3 | DEA TESTDRUG1 BNAME 3MG TAB | 3 G | TAB |
| ☐ | 0 | 10 | NP 3 | DEA TESTDRUG1 BNAME 4MG TAB | 4 G | TAB |
| ☐ | 0 | 7 | NP 3 | DEA TESTDRUG1 BNAME 5MG TAB | 5 G | TAB |

Buttons: PROFILED/ NON PROFILED | BRAND/ GENERIC | REVIEW | ISSUE
CLOSE | CANCEL | MAINT | FAX | DETAILS | ENTER

METHOD AND APPARATUS FOR ONSITE DISTRIBUTION OF MEDICATIONS AND MEDICAL SUPPLIES

CROSS-REFERENCE TO RELATED APPLICATIONS

This application claims the benefit of U.S. Provisional Application No. 61/615,711, filed Mar. 26, 2012, the disclosure of which is hereby incorporated by reference herein in its entirety.

BACKGROUND

The invention relates generally to a distribution machine and associated methods, and more particularly, to a distribution machine for distributing medical supplies and medications (e.g., "medical items"), including controlled substances, at a remote location such as a healthcare facility where the patient or recipient is located, a community center of a residential complex, and similar direct or indirect distribution locations.

Medication supply companies have commonly provided Automated Dispensing Cabinets (ADC's) at hospitals and other healthcare facilities to extend the inventory of non-prescription medications to locations proximate to the patients that may require such medications. These Automated Dispensing Cabinets enable a nurse or another authorized user to request medications on demand for rapid delivery to a patient. One known type of Automated Dispensing Cabinet includes a plurality of lockable drawers with a plurality of lockable bins in each drawer. In this drawer-type of Automated Dispensing Cabinet, an authorized user selects a particular medication and then a corresponding drawer and bin containing that medication are unlocked so that the user can retrieve the medication and remove it from the ADC. These conventional Automated Dispensing Cabinets have improved the ready access of medication and medical supply inventory in hospitals and other facilities.

Depending on the relative sizes of the bins and the drawers, a drawer-type Automated Dispensing Cabinet generally includes up to 300-400 bins for holding doses of medication. In order to maximize the inventory available onsite, many of the bins typically receive multiple doses of a medication. As a result, any time a nurse or other authorized user accesses a particular bin, that user has access to a plurality of doses of the requested medication. These Automated Dispensing Cabinets therefore provide additional inventory that can range into the thousands of unit doses of up to 300-400 different types of medication. One continuing problem with these cabinets is the retrieval of multiple doses from the bin when only a single dose has been requested. A user may take extra doses from the cabinet by accident or for a plurality of malicious reasons, including unauthorized distribution or sale to other persons. This diversion of inventory affects the management of the available inventory and may significantly delay the delivery of a needed medication or medical supply to a patient when the loss is discovered. Furthermore, with multiple users accessing the cabinet regularly, it can be difficult to determine which authorized user diverted the inventory to hold that user accountable for the loss of inventory. When a controlled substance is diverted, the facility is subject to an intense investigation with a high burden of paperwork to determine the offending party and correct the problems with the dispensing of inventory. These problems have caused a lack of confidence in these Automated Dispensing Cabinets in state and federal agencies that would normally approve such devices for use in many settings.

More recently, medication supply companies have extended the use of Automated Dispensing Cabinets to long-term care facilities, which may be located in a remote area that is a significant distance from the closest pharmacy or hospital. In these remote areas, the accurate monitoring and control of inventory is even more critical. In addition, these long-term care facilities generally require the distribution of a higher number of different medications because these facilities manage both the various prescriptions that patients are taking as well as non-prescription medications such as pain medication for on demand use and medical supplies. To this end, a long-term care facility may actually require up to 1400-1500 different medications or groups of medications (e.g., in patient-specific blister packages or pouches) or more compared to the 300-400 medications that are desirable to have on demand in a traditional hospital or other healthcare setting. Conventional Automated Dispensing Cabinets simply do not have enough bins or compartments, within an acceptable or allowable footprint, to accommodate these potential needs regarding the breadth of inventory necessary in a long-term care facility. Moreover, the higher number of medications needed by a long-term care facility is likely to include a number of controlled substances, which must be carefully regulated and monitored to comply with federal and state regulations. In addition, the Automated Dispensing Cabinets have not included monitoring or sensing systems that can accurately detect the diversion of additional or incorrect medications from a bin of a drawer containing multiple doses or medications. In sum, known Automated Dispensing Cabinets are not suitable for the provision of the high number of medications needed while also ensuring acceptable levels of regulation and monitoring of controlled substances.

Additionally, several known Automated Dispensing Cabinets include complex drive mechanisms and/or sensors for controlling an automated dispensing of medications from the cabinet. These complex systems add significant cost and time to the manufacturing of the Automated Dispensing Cabinet and also provide significantly more elements that can fail and stop proper operation of the Automated Dispensing Cabinet. These additional failure modes increase the rate of maintenance and repairs necessary to keep the Automated Dispensing Cabinet in operation, thereby increasing the likelihood that the cabinet will not be available to dispense medications when needed by patients.

Consequently, it would be desirable to provide an apparatus and method for onsite distribution of medications and medical supplies that addresses one or more of these concerns with conventional Automated Dispensing Cabinets.

SUMMARY OF THE INVENTION

According to one embodiment, a method is provided for selectively distributing a plurality of medical items stored in a secure access distribution machine. The distribution machine includes a housing enclosing a plurality of bins behind at least one access door and also includes a controller with a processor and a memory. An input device receives first identification data associated with a user, second identification data associated with a patient, and item selection data that identifies at least one medical item that is selected for distribution to the user and administration to the patient. The processor compares the first identification data to information stored in memory to confirm that the user is authorized to distribute medical items from the distribution machine. In response to receiving the second identification data, the processor also actuates the display of a patient record stored in the memory and associated with the patient on a display. The patient record includes a list of medical items that are previously prescribed or approved for distribution to the patient. The item selection data identifies at least one medical item from this list of pre-approved or prescribed medical items. In response to receiving the item selection data, the distribution machine rotates a bin holding a first medical item to a position behind a corresponding one of the access doors and unlocks the corresponding access door so that the access door opens. This opening of the access door provides access for the user to reach into the bin to manually retrieve the first medical item from the bin. The processor then verifies that the user received the first medical item (e.g., the correct medical item that should have been retrieved) after it has been manually retrieved from the bin. The process of distributing and verifying repeats for each other medical item identified in the item selection data, thereby limiting the user to access to the medical items individually on an bin-by-bin basis. The patient record is then updated to assign to the patient the at least one medical item that has been distributed to the user for administration to the patient.

The distribution machine may also include a plurality of access doors stacked on top of each other in the housing. In such embodiments, the housing and access doors block access to all bins within the housing except for the bin holding the first medical item when the distribution of the first medical item is to occur. In this regard, the other access doors remain locked and closed to limit the user to manual retrieval of only the first medical item. At least some of the access doors also include stationary blocking baffles rigidly mounted to the housing adjacent to the access doors, the blocking baffles preventing access to adjacent bins next to the bin holding the first medical item.

In another aspect, the verification of the user receiving the first medical item includes prompting the user to scan a machine readable indicia associated with the retrieved medical item using a scanner located at the housing. The processor receives the scanner input from the scanner and determines whether the retrieved medical item that has been scanned is the first medical item. If the retrieved medical item is incorrect (e.g., is not the first medical item), then the error is reconciled by prompting the user to insert the retrieved medical item into a return receptacle mounted on the housing. The return receptacle includes a one-way door providing access to insert, but not remove, rejected medical items. After verifying that the correct first medical item has been removed and scanned, the processor may update the patient record to reflect distribution of the first medical item to the patient. In embodiments where the access door includes a latching mechanism with an engagement drum and a locking device, the locking device is disengaged from the engagement drum using an automated drive actuator when the access door is to be unlocked and opened for distribution of a first medical item. The locking device is re-engaged with the engagement drum only after receiving the scanner input to verify the correct first medical item was removed, therefore preventing closing and locking of the access door until the verification process is completed. This process limits the number of total medical items that may be removed without verification to one.

In another aspect, the access door also includes a camera. In such embodiments, verifying that the user received the first medical item also includes capturing image data using the camera and analyzing the image data with the processor to confirm whether the first medical item has been removed from the bin. This analysis may include retrieving a previously-stored pixilated digital image of the bin from memory and then pixilating the captured image data to compare the two images. The comparison determines whether enough pixels have changed to verify the removal of the first medical item from the bin. It will be understood that a plurality of the bins within the housing may be positioned next to the camera so that the camera can capture digital images of each bin to store these images for use later in the comparison described above. Thus, the provision of a camera on the access door enables another method of double checking that the first medical item has been removed from the housing.

Prior to distributing the first medical item to the user, a plurality of additional steps are required if the processor determines that the first medical item is a controlled substance. To this end, the user record associated with the user is analyzed to determine whether the user is authorized to receive a controlled substance. If the user is authorized, then a prompt is given for a witness to enter witness identification data, and the user record associated with the witness is received and analyzed to make certain that the witness is authorized to witness distributions of controlled substances. If both the user and the witness are authorized, then the distribution of first medical item is allowed. However, the controlled substances are not presented for removal if either of these persons fails to be authorized. In addition to the controlled substances context, there are a plurality of conditions that can lead to a prompting for a witness to input witness identification data. These conditions include when the first medical item exceeds a threshold schedule level stored in the patient record, when the first medical item is not on the patient's profile, and when a distribution is canceled during retrieval of the first medical item.

A restocking process may also be used with the distribution machine. During this restocking process, the processor receives a scan of a machine readable indicia on a purchase or shipping order that is associated with a plurality of medical items to be stocked inside the housing. The processor then prompts the user to provide a verification scan of the machine readable indicia on a first item to be stocked. A first available bin is identified and rotated to a position adjacent an access door, and this access door is unlocked and opened to provide access into the first bin. Once the user has placed the first item in the first bin, the access door is locked following closing of the door by the user. An image of the first bin with the first item is captured to verify that the manual placement of the first item has occurred. The process of receiving the verification scan, rotating, opening, locking, and scanning is repeated for each other item associated with the purchase or shipping order. Consequently, the restocking process works similarly to the distribution process in that the medical items and items are individually scanned in and out with only access to one bin or medical item at a time.

In another aspect, in response to receiving the scan of the purchase or shipping order, the processor may automatically update an inventory record stored in memory to include various information about each of the plurality of medical items to be stocked, including a lot number, an expiration date, a National Drug Code, and a UPC, thereby not requiring separate manual entry of these items of information for each of the plurality of medical items to be stocked. This simplifies the process of restocking the distribution machine. Whenever multiples of a medical item are stored in a single bin, the method further includes updating a bin record stored in memory for the bin holding the first medical item to decrement a "bin quantity on hand" variable stored in the memory by one.

If a plurality of medical items is selected by the user for distribution, then the distributing and verifying steps are repeated individually for each of the plurality of medical items needed by the patient. The plurality of bins may be mounted on a plurality of carousels on carousel drive axles collectively centered at a central drive axle in the interior of the housing. Distributing the first medical item in these embodiments further includes rotating all of the plurality of carousels around the central drive axle with a first motor, and rotating each of the plurality of carousels simultaneously around their carousel drive axles with a second motor. As a result, the carousel carrying the bin with the first medical item is moved near the access door and then the specific bin is rotated into position behind the corresponding access door. An outer camera may be mounted on the housing so that still or moving images of the user at the distribution machine can be taken during the distributing and verifying steps described above. The captured still or moving images are stored in memory with a transaction record so that this information can be reviewed later if necessary.

In a further aspect, the distribution machine includes a document scanner at the housing. When a prescription document for a patient comes into the facility, the processor may receive a scanned image of the prescription document from the document scanner. This scanned image is then sent to a remote location for approval by a pharmacist, and if approved, the medical item(s) is added to the list of scheduled or prescribed medical items on a patient record. In addition, the patient records stored in memory and displayed on the display are those approved for distribution to the patient already. That simplifies the process of selecting medical items to distribute to a number of patients that may be located in the same facility serviced by a common distribution machine. In addition, the document scanner may also be used to scan in other documents that need verified or reviewed offsite, such as a new patient admission document when a new patient is admitted to the facility. In such a circumstance, offsite pharmacy personnel can review and approve the new patient and a new patient record may be created in memory automatically after this approval.

In another embodiment of the invention, a secure access distribution machine is provided for distributing a plurality of medical items. The distribution machine includes a housing enclosing an interior and including at least one access door and an input device. A plurality of carousels is located within the interior, and each carousel includes a plurality of bins for storing the plurality of medical items. A drive mechanism is configured to rotate each of the plurality of carousels such that each of the plurality of bins may be positioned adjacent to the at least one access door. The distribution machine also includes a controller having a processor and a memory, the controller operatively coupled to the access door, the input device, and the drive mechanism. The controller is configured to perform a series of operations to distribute medical items from the housing. This series of operations includes (i) determining that a user is an authorized user permitted to distribute medical items, (ii) identifying a bin holding a first medical item selected for distribution from a list of pre-approved or prescribed medical items from a patient record, (iii) actuating the drive mechanism to move the bin holding the first medical item to a position behind a corresponding access door, (iv) unlocking and opening the corresponding access door to enable the user to reach into the housing and manually retrieve the first medical item, (v) verifying that the first medical item was removed by the user, and (vi) updating the patient record to assign to the patient the first medical item.

In one aspect, the housing may include a plurality of access doors stacked on top of each other so that access to all other bins within the housing is blocked when the corresponding access door is unlocked and opened. Each of these access doors may also include a camera that may be used to capture still images of bins within the housing to verify removal of the first medical item after a distribution. Stationary blocking baffles may also be rigidly coupled behind at least some of the plurality of access doors. The stationary blocking baffles prevent access to bins adjacent to the bin holding the first medical item when the corresponding access door is unlocked and opened. In addition, each of the access doors includes a latching mechanism for selectively locking the access door in a closed position. The latching mechanism has an engagement drum manually rotated by opening or closing the access door and a locking member moved by an automated drive actuator.

In another aspect, a scanner is located at the housing for reading machine readable indicia on medical items to be placed within one of the plurality of bins or distributed from one of the plurality of bins. The distribution machine also includes a digital outer camera mounted on the housing and configured to record still images or moving images of an user at various times during access and use of the distribution machine. A return receptacle may also be positioned on the housing with a one-way door enabling insertion, but not removal, or rejected or incorrect medical items from the housing. The drive mechanism may be limited to a first motor that rotates all of the plurality of carousels around a shared central drive axle and a second motor that simultaneously rotates each of the carousels around corresponding carousel drive axles. Therefore, the drive mechanism is simplified compared to conventional designs.

Various additional features and advantages of the invention will become more apparent to those of ordinary skill in the art upon review of the following detailed description of the illustrative embodiments taken in conjunction with the accompanying drawings.

BRIEF DESCRIPTION OF THE SEVERAL VIEWS OF THE DRAWINGS

The accompanying drawings, which are incorporated in and constitute a part of this specification, illustrate various embodiments of the invention and, together with a general description of the invention given above and the detailed description of the embodiments given below, serve to explain the embodiments of the invention.

DETAILED DESCRIPTION

With reference to FIGS. 1 through 13C, an exemplary embodiment of a medication distribution machine 10 is illustrated. Although the term "medication distribution machine" (hereinafter "distribution machine") is used throughout the following description, it will be understood that the distribution machine 10 is operable to distribute medications, medical supplies, and other related items (also referred to collectively as "medical items") needed in a remote facility (hereinafter "healthcare facility"). The distribution machine 10 operates to extend inventory supplies closer to the location of one or more patients, such as in the long-term care facility setting. Advantageously, the distribution machine 10 contains about 1,050 to 4,000 bins or compartments (e.g., storage locations) for holding medications and other items, each bin being separately and individually accessible to control the distribution of medications (including controlled substances) to authorized users. It will be understood that multiple distribution machines 10 may be linked together by a single control module to further extend or reconfigure the available number of bins or compartments available to a healthcare facility, thereby providing any level of inventory breadth required for a particular facility. As a result, the likelihood of an accidental or malicious diversion of medications is reduced compared to conventional Automated Dispensing Cabinets. Furthermore, as detailed below with reference to FIGS. 15 through 17T, the work flow experienced by users when operating the distribution machine 10 enables quick and convenient identification of available medications and accurate selection of those medications for distribution to the user.

Figure 1:
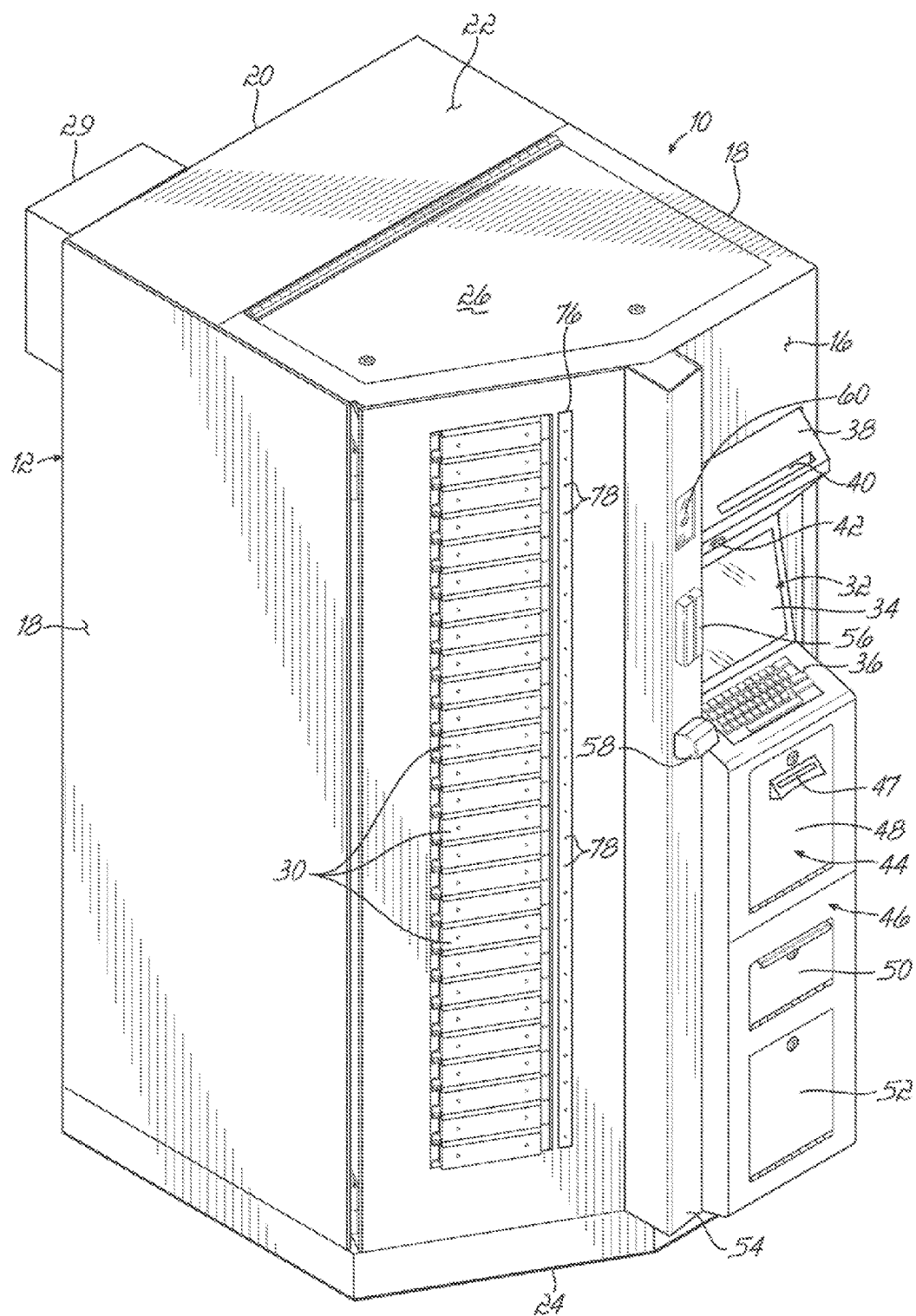
FIG. 1 is a perspective view of one embodiment of a medication distribution machine in accordance with the present invention, showing external features of the distribution machine.

With particular reference to FIG. 1, the distribution machine 10 includes an outer housing 12 defining a closed interior 14 for storing the plurality of medications and other items. The housing 12 includes a front wall 16 configured to face a user, side walls 18 extending from the front wall 16, a rear wall 20 opposite the front wall 16, and top and bottom walls 22, 24 connected to each of the front, side, and rear walls 16, 18, 20. The top wall 22 of this embodiment includes a service panel 26 hingedly coupled to the top wall 22. This service panel 26 is locked in a closed position during normal operation and cannot be opened by anyone other than authorized service personnel. To this end, any medications or controlled substances contained within the closed interior 14 are not accessible by thieves or unauthorized persons without cutting through the housing 12. In the illustrated embodiment, the housing 12 defines a generally rectangular footprint of about 36 inches by 39 inches (0.914 meters by 0.991 meters). It will be understood that the housing 12 may define any other shape or size that is convenient to the desired healthcare facility setting without departing from the scope of the present invention. It will also be understood that the size of storage locations (bins or compartments) may be sized and shaped in various different configurations that are convenient to the storage of medications and other items as required by the particular healthcare facility. Regardless of the particular shape and size of the housing 12 and the storage locations, the distribution machine 10 of the current invention advantageously maximizes the density of storage locations available within the chosen footprint as described in further detail below.

In some embodiments, the distribution machine 10 may be used to store medications and other items that may require storage at a cool or cold ambient temperature (e.g., insulin). In these embodiments, the distribution machine 10 may include an insulated housing 12, seals at any access location or door, and a conventional refrigeration unit 29 connected to the housing 12. In the illustrated embodiment of FIG. 1, the refrigeration unit 29 is shown schematically as a box on the rear wall 20 of the housing 12, although it will be understood that a coil-type or similar conventional refrigeration unit 29 may be positioned along any wall of the housing 12. The refrigeration unit 29 is monitored by a thermocouple (not shown) and/or other sensors connected to the controller of the distribution machine 10 such that the closed interior 14 may be maintained at a desirable temperature and possibly also at a desirable humidity relative to the external environment. Further explanation of the conventional refrigeration unit 29 and its operation are not provided as these units are well understood in the art of vending machines.

The front wall 16 of the housing 12 contains a plurality of input/output devices configured to interact with a user and a plurality of stacked access doors 30 located adjacent the plurality of input/output devices. In this regard, the housing includes a user interface 32 located on the front wall 16 adjacent to the right hand side wall 18. The user interface 32 includes a graphical display screen 34 for delivering information visually to a user and a keyboard 36 located immediately below the display screen 34 for receiving manual input from the user. The graphical display screen 34 includes a touch screen interface that enables users to manipulate the operation of the distribution machine 10 either with touch commands or with keyboard commands, when applicable. For example, the graphical display screen 34 may provide a digital numerical entry pad when a quantity of medications needs to be entered during the workflow described below. A document scanner 38 is located above the display screen 34 and includes an input slot 40 for receiving documents to be scanned such as prescriptions received from physicians. The document scanner 38 projects slightly outwardly from the housing 12 above the display screen 34.

A one-touch call button 42 is positioned on the lower half of the document scanner 38. The call button 42 may be used to initiate an immediate conversation with one or more pharmacists working in a centralized location. These centralized pharmacists review, verify, and approve new prescriptions submitted at the distribution machine 10 and are available via the one-touch call button 42 to answer any questions a user might have about distributing a particular medication for a particular patient. It will be understood that the housing 12 also contains a microphone and speaker (not shown) for conducting these calls with the centralized pharmacists, as well as providing audible feedback during normal operation of the distribution machine 10.

The front wall 16 of the housing 12 further carries a receipt printer 44 located adjacent to the keyboard 36. The receipt printer 44 is operable to provide a printed record of medications and supplies removed for a patient from the distribution machine 10. The keyboard 36 and receipt printer 44 are each mounted above of a return receptacle 46, also referred to as a reject bin. To this end, the receipt printer 44 includes a printer outlet 47 located on a printer access door 48. The hardware (not shown) of the receipt printer 44 is located along an inner surface (not shown) of the printer access door 48, which may be opened by an authorized user or by maintenance personnel to replace ink cartridges or a paper roll when necessary. If any medications are accidentally retrieved from the closed interior 14 or are not used by a patient, these medications can be collected in the return receptacle 46 for later removal by authorized service personnel. More particularly, the return receptacle 46 includes a moveable inlet flap door 50 configured to receive any rejected medications from a user. The inlet flap door 50 is sized and oriented to open inwardly to receive only medications or items being returned by a user, and this opening movement does not enable unauthorized entry of a user's hand into the return receptacle 46. The return receptacle 46 also includes a lockable outlet door 52 adjacent a bottom of the return receptacle 46. Each of the inlet flap door 50 and the outlet door 52 are in a closed position during normal operation and the outlet door 52 cannot be opened by anyone other than authorized service personnel (because the inlet flap door 50 is sized and oriented to prevent unauthorized access into the return receptacle 46 by a user's hands). Accordingly, any returned or rejected medications, including but not limited to controlled substances, are securely stored and cannot be removed by thieves or unauthorized personnel without cutting through the housing 12 at the return receptacle 46.

The front wall 16 of the housing 12 also includes an outwardly-projecting ridge 54 located between the plurality of access doors 30 and the previously-described input/output devices. The ridge 54 provides one or more receptacles for receiving additional input/output devices as selected for the particular healthcare facility. In the illustrated embodiment, these devices include an identification card swipe reader 56 and a barcode reader 58. The card swipe reader 56 is configured to provide one identification of a user during the authorization process before any medications may be removed from the distribution machine 10. It will be understood that additional or alternative identification sensors may be positioned along the ridge 54 in other embodiments of the present invention, including but not limited to biometrics scanners (e.g., fingerprint readers), a radio frequency identification (RFID) detector, an HID access control reader for use with tags, key fobs, or cards, and other known sensor devices. It will also be understood that the barcode reader 58 may be replaced by any scanner that is used to read machine readable indicia of all types, including, but not limited to, barcodes, images, 2-D barcodes, and other known indicia. The barcode reader 58 is configured to detect machine readable indicia placed on various items, including the packaging of every medication held within the distribution machine 10. As explained in further detail below, the barcode reader 58 is used to verify the removal of the appropriate medication from a particular bin during normal operation. It will be understood that the barcode reader 58 may also be used to identify a user during the authorization process if the user is authorized using personal identification badges with barcodes, for example. The ridge 54 also contains a digital camera 60 configured to record the images of a user standing at the user interface 32 of the distribution machine 10. Thus, an image record of each user who removes medications from the distribution machine 10 is retained for later review should such a review become necessary (i.e., during the investigation of a medication diversion). It will be appreciated that the digital camera 60 may be operable to record still images or video recordings (live action images or streaming images) for retention in the records of the distribution machine 10 and for use during live communication with a pharmacist initiated by the one-touch call button 42. The digital camera 60 may be triggered by actions of a user at the machine 10 or remotely by an offsite pharmacist or other pharmacy personnel.

Figure 2:
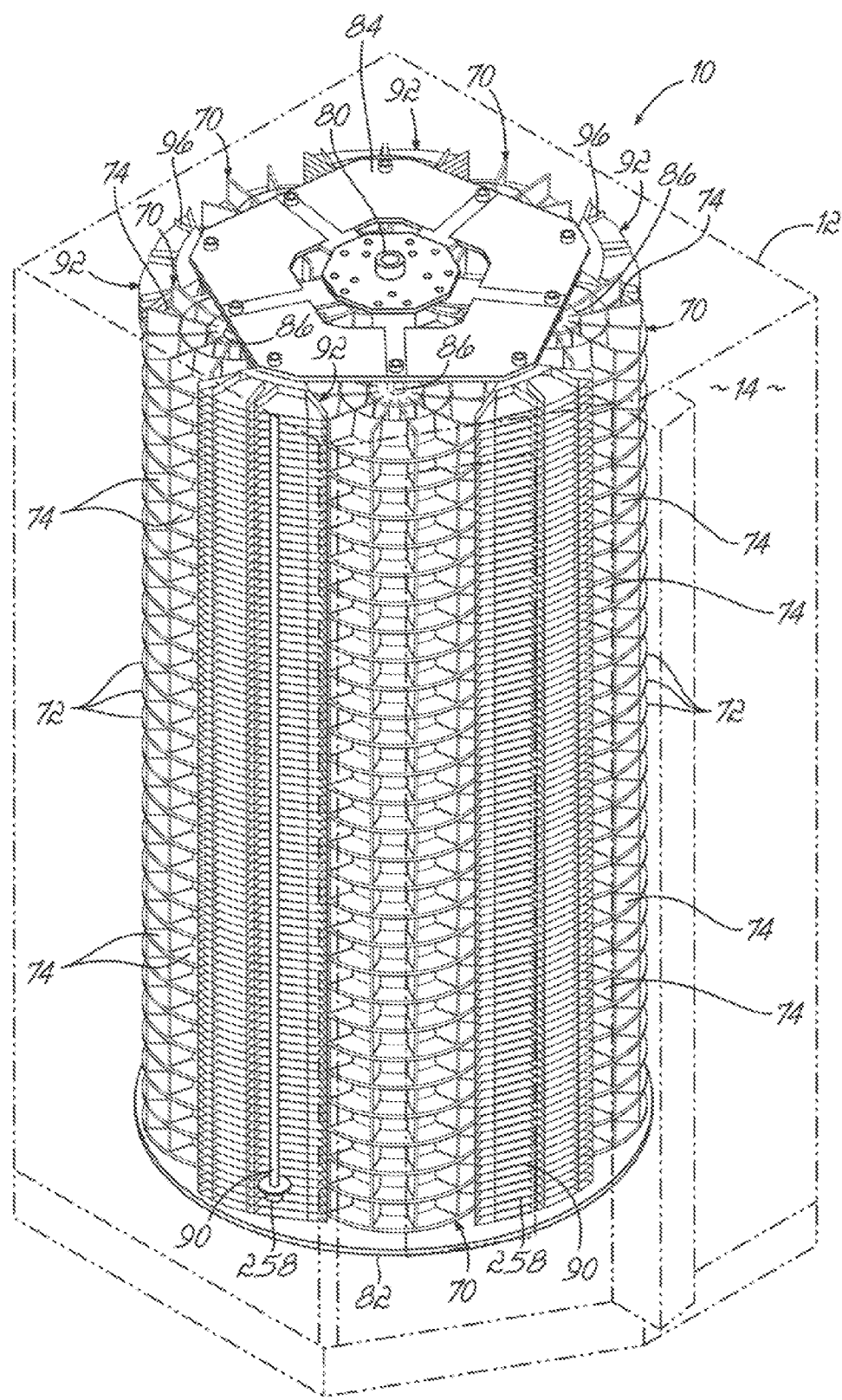
FIG. 2 is a perspective view of the distribution machine of FIG. 1, with the housing and external features shown in phantom so that a plurality of stacked layers of carousels including platforms for holding medical items and medications is shown.

The plurality of access doors 30 are arranged in a stack as shown in FIG. 1 such that each access door 30 is adjacent to the next access door 30 in the stack. This arrangement of access doors 30 enables a plurality of carousels 70 to be accessed from the exterior, each carousel 70 including a series of stacked platters 72 defining bins 74 within the closed interior 14 as shown in FIG. 2. Each of the access doors 30 is sized to permit access to a bin 74 in only one of the carousels 70, thereby protecting the remainder of the carousels 70 within the housing 12 from unauthorized access. Each access door 30 is hingedly coupled to the front wall 16 and is locked in the closed position by a latching mechanism described in further detail with reference to FIGS. 11A through 11D below. It will be understood that the plurality of access doors 30 may be replaced by a moving access door mounted on an endless belt or a similar device in other embodiments consistent with the scope of the current invention but not shown in the Figures.

Returning to FIG. 1, the front wall 16 also includes an indicator panel 76 with an indicator light 78 located adjacent to each access door 30. The indicator lights 78 are illuminated to indicate when the nearest access door 30 is unlocked. Thus, a user can readily determine whether an access door 30 is locked or unlocked by reviewing which indicator lights 78 are illuminated on the indicator panel 76. The access doors 30 and the housing 12 are generally opaque such that none of the carousels 70 or medications held within the closed interior 14 is visible outside the housing 12. The detailed operation of the access doors 30 and associated latching mechanisms and door cameras is described in further detail below.

With reference to FIG. 2, the closed interior 14 and the plurality of carousels 70 located within the housing 12 of the distribution machine 10 are shown. It will be understood that a carousel-type layered storage system has been previously used in vending machines and in tool dispensing systems for use on jobsites. For example, one carousel-type layered storage system is disclosed within U.S. Pat. No. 5,337,920 to Clausen, the disclosure of which is hereby incorporated by reference in its entirety. In another example, a carousel-type layered storage system is disclosed within U.S. Pat. No. 7,086,558 to Pixley et al., the disclosure of which is hereby incorporated by reference in its entirety. Although each of these carousel-type storage systems includes a plurality of bins individually accessible by using a drive mechanism, the drive mechanism of the current invention (described in further detail with reference to FIGS. 13A through 13C below) simplifies and reduces the number of elements necessary to reliably move each bin 74 into position adjacent one of the access doors 30. Furthermore, the carousels 70 and platters 72 of the current invention have been modified to maximize the use of the closed interior 14 and maximize the number of available bins 74 for storing unit doses of medication or other medical supplies. As briefly discussed above, each of the bins 74 may be reconfigured to define a desirable shape and size for particular medications and other supplies needed at the healthcare facility in which the distribution machine 10 is to be used. It is believed that such a carousel-type storage system has not been previously applied to the Automated Dispensing Cabinet field, and thus represents an advantageous improvement over conventional Automated Dispensing Cabinets. The distribution machine 10 permits the bins 74 to be densely packed as inventory locations in a comparatively compact space and then be moved and presented for user access at a particular access door 30.

Returning to FIG. 2, the plurality of carousels 70 includes five carousels 70 located in close proximity with each other about a central drive axle 80. It will be appreciated that the size, shape, and number of carousels 70 may be decreased or increased in other embodiments without departing from the current invention. The central drive axle 80 and each of the carousels 70 extend along substantially the entire height of the closed interior between a bottom support turntable 82 and a top connection plate 84. To this end, each carousel 70 includes a plurality of closely-stacked platters 72 corresponding in number and location to the stack of access doors 30 in the front wall 16 (i.e., about thirty layers as shown in the illustrated embodiment). The top connection plate 84 is formed from a unitary planar piece of material or a plurality of links coupled together, as shown in FIG. 2. A carousel drive axle 86 extends through each of the platters 72 of a carousel 70 and is secured in position at the top connection plate 84. Each of the carousel drive axles 86 is secured so as to be free to rotate in position with respect to the top connection plate 84 such that the various bins 74 on the platters 72 can rotate with respect to the corresponding access doors 30. The central drive axle 80 and the carousel drive axles 86 also extend through the bottom support turntable 82 to engage with components of the drive mechanism described with reference to FIGS. 13A through 13C below. In general, the central drive axle 80 operates to rotate the plurality of carousels 70 collectively in combination with rotation of the bottom support turntable 82 and the top connection plate 84, while the carousel drive axles 86 operate to rotate the carousels 70 individually in position. As clearly shown in FIG. 2, the arrangement of carousels 70 about the central drive axle 80 enables a maximum number (e.g., up to 2,100 or more in the exemplary embodiment) of bins 74 to be located within the closed interior 14.

Also shown in FIG. 2, a plurality of stationary support rods 90 extends between the top connection plate 84 and the bottom support turntable 82 and is positioned in the spaces between adjacent carousels 70 on the outboard or outer radial portion of the bottom support turntable 82. These support rods 90 provide additional rigidity to the plurality of carousels 70 to thereby assist with maintaining alignment of the top connection plate 84 and the bottom support turntable 82 without applying significant bending stresses on the carousel drive axles 86. To this end, each of the support rods 90 is rigidly secured to both the bottom support turntable 82 and to the top connection plate 84. In addition, each of these stationary support rods 90 supports a stationary partial carousel 92 having a plurality of layers of storage locations or bins 94 substantially similar to the previously described storage bins 74 on the moveable carousels 70. By the terms "stationary" and "moveable", it is understood that this refers to the relation of the carousels 70 or partial carousels 92 with respect to the bottom support turntable 82. Each of the partial carousels 92 on the stationary support rods 90 does not need to rotate because such rotation would interfere with adjacent carousels 70 and because the bins 94 on those partial carousels 92 already is directed radially outwardly from the plurality of carousels 70. The bins 94 on the stationary partial carousels 92 may be resized by moving divider plates 96 similar to the process described below for resizing bins 74 of the rotatable carousels 70. In the illustrated embodiment, each stationary partial carousel 92 defines about ⅙ to ⅓ of a complete annular carousel with 30 layers of two bins 94 that further maximize the use of the closed interior 14 for storage locations. It will be understood that the particular positioning, size, shape, and/or number of support rods 90, stationary partial carousels 92, and the bins 94 on those partial carousels 92 may be different in other embodiments consistent with the scope of the current invention.

Figure 3:
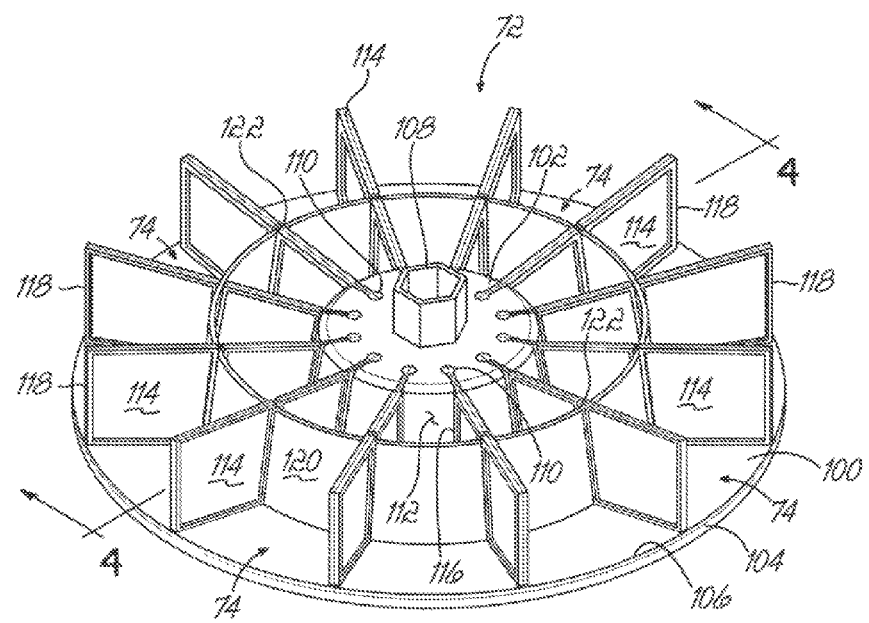
FIG. 3 is a perspective view of one of the platforms of the carousels shown in FIG. 2, the platform including a plurality of dividers and an intermediate annular wall for defining a plurality of storage bins on the platform.
Figure 4:
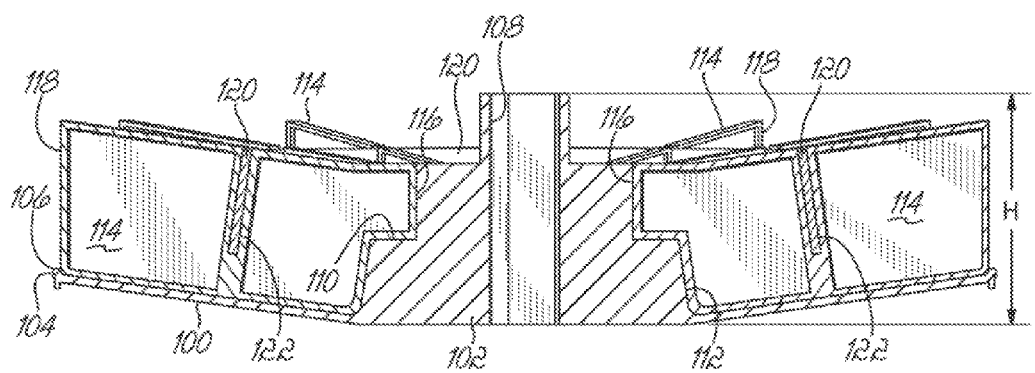
FIG. 4 is a cross-sectional side view of the platform of FIG. 3, taken along line 4-4.

With reference to FIGS. 3 and 4, one of the platters 72 used with the plurality of carousels 70 shown in FIG. 2 is illustrated in further detail. In this regard, the platter 72 includes a bottom plate 100 extending from a central hub 102 to an annular outer periphery 104. The bottom plate 100 is angled slightly downward from the outer periphery 104 to the central hub 102 such that the bottom plate 100 defines a generally conical profile, which assists with the retention of medications and other items. Also to this end, the outer periphery 104 includes a small projecting lip 106 extending upwardly from the bottom plate 100 to assist with retention of medications and other items. More specifically, as the platter 72 rotates during operation to move a particular bin 74 into position adjacent an access door 30, centripetal forces are applied to any medications or other items located in the bins 74. By angling the bottom plate 100 inwardly and providing the projecting lip 106 at the outer periphery 104, these medications and other items are encouraged to resist the centripetal force that could otherwise cause these items to fall out of the bins 74. Consequently, unintentional dropping of medications and other items within the closed interior 14 of the distribution machine 10 are minimized if not eliminated altogether by this arrangement of the platter 72.

As shown in FIGS. 3 and 4, the central hub 102 projects upwardly from the bottom plate 100 and defines a total height H of the platter 72. This height H generally corresponds to a height of the corresponding access doors 30. Alternatively, the height H may be different than the height of the access door 30, and in such circumstances spacers and/or pins located between the central hubs 102 of adjacent platters 72 may be used to correct for any tolerance-based differences in the height of the platters 72. The central hub 102 includes a central aperture 108 extending through the entire height H of the platter 72. The central aperture 108 is sized and shaped to receive the carousel drive axle 86. Thus, in the exemplary embodiment shown in these figures, the central aperture 108 defines a hexagonal cross section configured to receive the hexagonal cross section of the carousel drive axle 86. These non-circular cross sections reliably transmit both rotational and translational movement of the carousel drive axle 86 to the platter 72 without additional coupling required between the carousel drive axle 86 and the platter 72.

The central hub 102 also includes a plurality of radial slots 110 extending from a location proximate to the central aperture 108 to a hub periphery 112 of the central hub 102. These radial slots 110 are configured to receive the inner ends 116 of divider plates 114 as shown most clearly in FIG. 3. The radial slots 110 only extend through a portion of the height of the central hub 102 at the hub periphery 112, although the height of the radial slots 110 may be modified in accordance with other embodiments of the current invention. The divider plates 114 are configured to extend in a generally radial direction from the inner end 116 at one of the radial slots 110 to an outer end 118 located at the outer periphery 104 of the bottom plate 100 to thereby divide the storage space above the bottom plate 100 into a plurality of bins 74. Twelve divider plates 114 are engaged with the twelve radial slots 110 in the central hub 102 of the platter 72 to cut the storage space into twelve generally pie-shaped segments referred to throughout as bins 74.

The platter 72 of this example also includes an annular limiting wall 120 which engages corresponding intermediate slots 122 in the divider plates 114. The annular limiting wall 120 effectively reduces the size of the bins 74 by moving the inner boundary of the bins 74 from the hub periphery 112 radially outwardly to the annular limiting wall 120. Especially for smaller items such as unit doses of medication, this shrinking of the bins 74 is advantageous for numerous reasons. For example, the smaller items are more likely to be positioned in a consistent location within the smaller bin size, which enables more accurate detection as described below, and the smaller bins 74 also limit how far a user has to reach through the relatively small access door 30 to obtain the desired item. The intermediate slots 122 are shown as extending through more than half of the height of each divider plate 114, although the depth of these intermediate slots 122 and the corresponding height of the annular limiting wall 120 at those slots may be adjusted without departing from the current invention. It will be understood that the annular limiting wall 120 is selectively removed from the platter 72 by lifting the limiting wall 120 out of the intermediate slots 122, and further that more than one intermediate slot 122 may be provided in the divider plates 114 to enable different configurations of the platters 72 as needed. However, these reconfigurations of the platters 72 must be performed by authorized service personnel and are not available during regular operation of the distribution machine 10.

Figure 5:
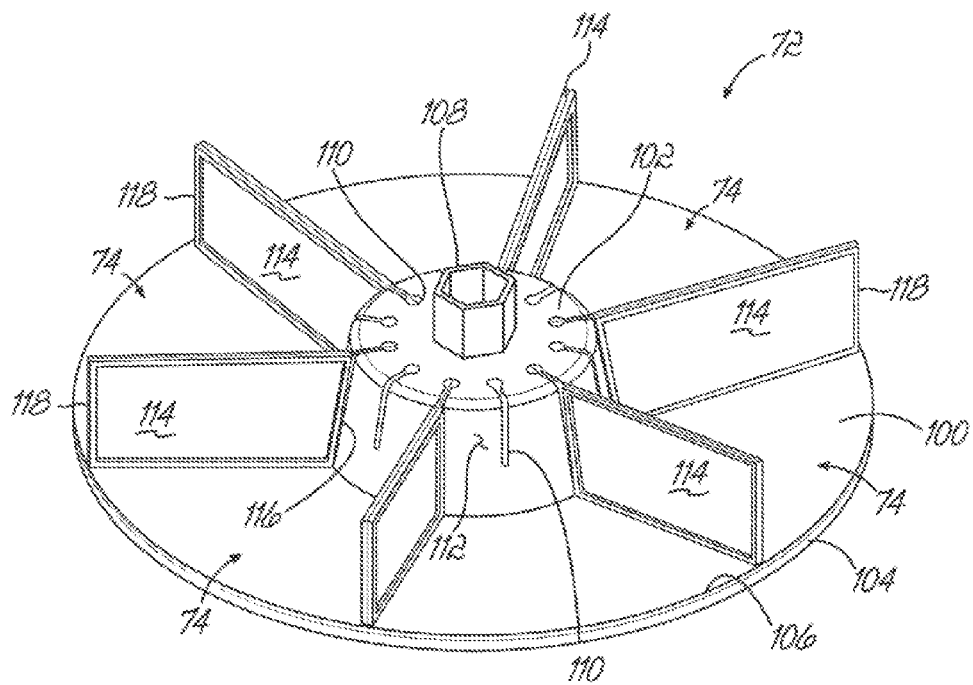
FIG. 5 is a perspective view of the platform of FIG. 3, with a number of the dividers and the intermediate annular wall removed to modify the bin configuration.
Figure 6:
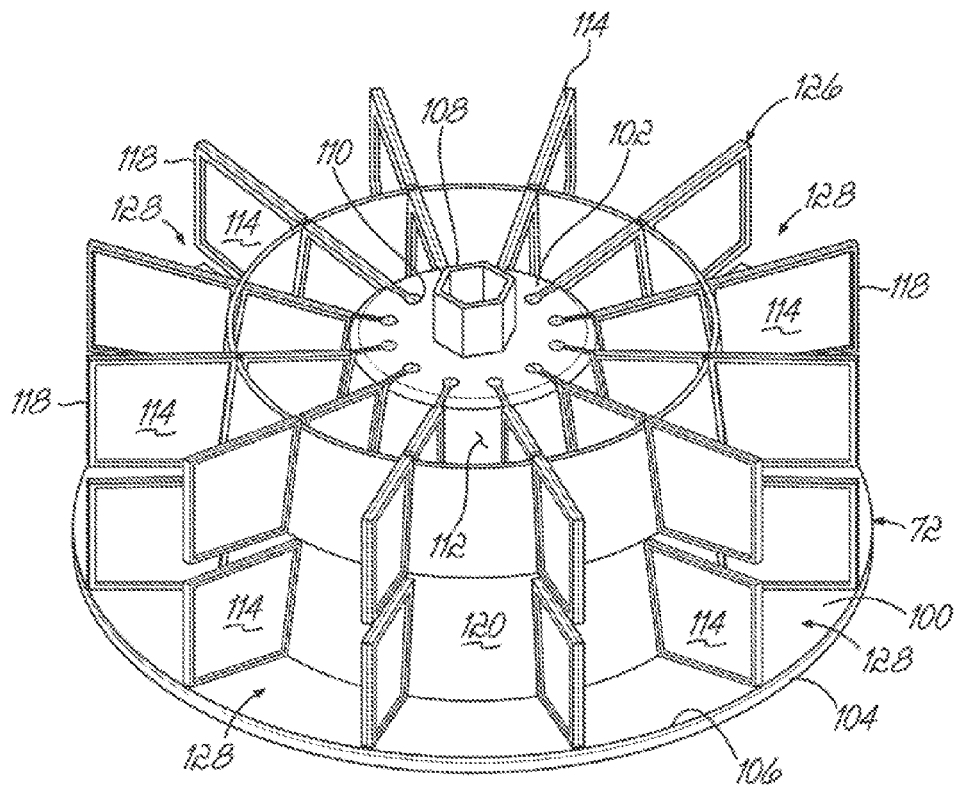
FIG. 6 is a perspective view of two of the platforms of the carousels in FIG. 2, with one of the platforms omitting a bottom wall to enable communication between the bins of the two platforms.

Other examples of reconfigured platters 72 for use in the closed interior 14 of the distribution machine 10 are shown in FIGS. 5 and 6. In FIG. 5, the platter 72 includes substantially the same basic structure of the platter 72 in FIGS. 3 and 4, including the slightly conical bottom plate 100 and central hub 102. In this reconfiguration, only six divider plates 114 are positioned in the radial slots 110 of the central hub 102 such that the storage space is divided into six bins 74 that are about twice as large as the bins 74 in FIG. 3. Furthermore, the annular limiting wall 120 and the intermediate slots 122 in the divider plates 114 have been omitted in this configuration to utilize more storage space for larger medications or items to be stored. It will be understood that any number of divider plates 114 (e.g., as few as two or as many as twelve in the illustrated embodiment) may be inserted into the radial slots 110 of the central hub 102 depending on the types of items and number of items that are required to be stored for a particular healthcare facility. In other words, the platter 72 may be divided into as few as two bins 74 or as many as twelve bins 74 in this exemplary embodiment.

With reference to FIG. 6, multiple platters 72, 126 in a given carousel 70 might also be used in conjunction to define a plurality of taller combined bins 128. To this end, a first platter 72 includes an identical structure as the platter 72 described above with reference to FIG. 3 (including the bottom plate 100, the central hub 102, twelve divider plates 114, and an annular limiting wall 120. The second platter 126 is configured to be positioned on the carousel drive axle 86 adjacent to and immediately above the first platter 72. The second platter 126 includes each of the same elements as the first platter 72 (these elements are marked with the same reference numbers) except for the bottom plate 100. As a result, the storage space of the two platters 72, 126 is not divided by a bottom plate 100 of the second platter 126 and therefore combines to define the taller combined bins 128 located between adjacent sets of divider plates 114. Such a configuration enables relatively elongate items that would not have normally fit into the bins 74 of the previous embodiments to be stored within the closed interior 14. As with the single platter arrangements, these configurations of multiple platters 72, 126 may be reconfigured by removing the corresponding annular limiting walls 120 as well as removing several of the divider plates 114 as required by the particular item to be stored. In addition, more than two second platters 126 may be stacked on top of a first platter 72 in other configurations within the distribution machine 10. Thus, the only limitation on the size of items that may be positioned within the distribution machine 10 is the limitation imposed by requiring all items to be inserted and removed through one or more open access doors 30, as explained in further detail below. For example, the opening formed by two access doors 30 that open at the same time enables larger sized items to be inserted and removed from the distribution machine 10 as described in reference to FIG. 10 below.

Figure 7:
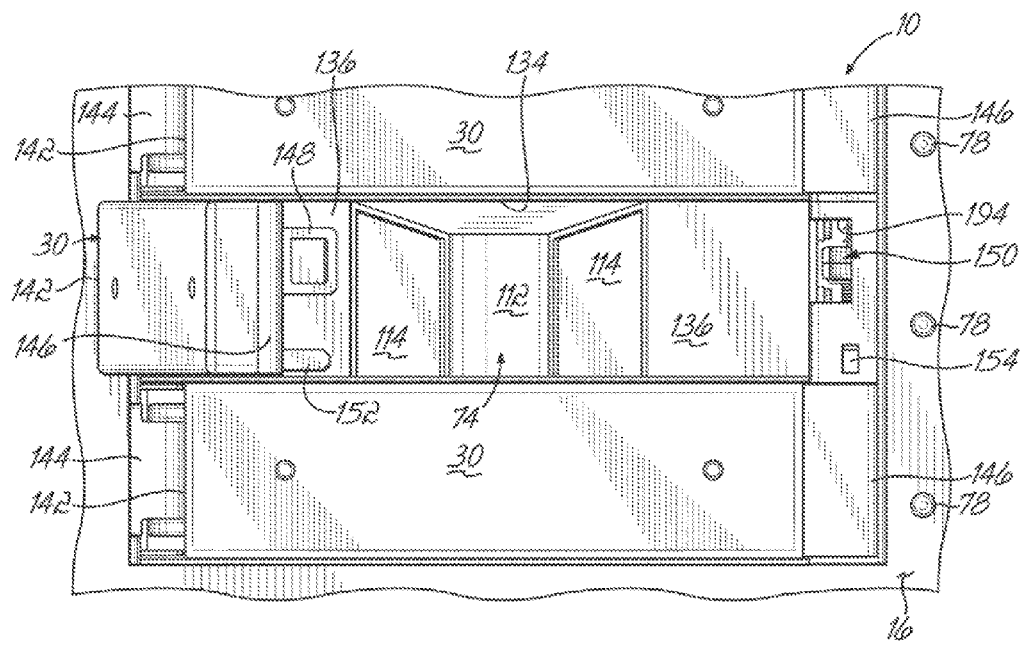
FIG. 7 is a front view of the distribution machine of FIG. 1 at a first access door, with the first access door opened to reveal a bin and first baffle plates blocking access to adjacent bins.
Figure 8:
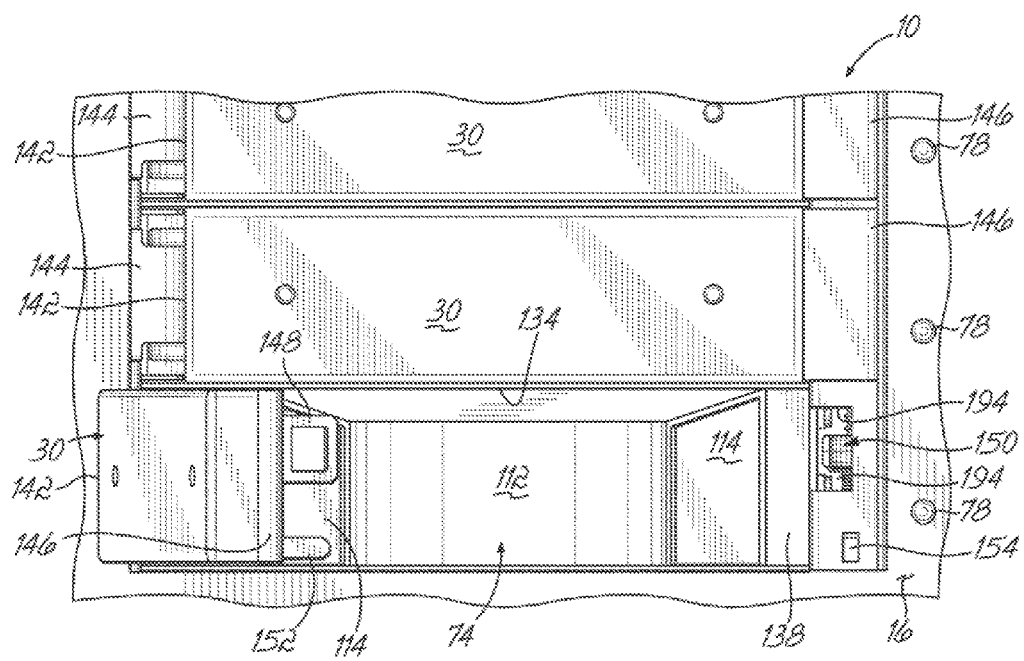
FIG. 8 is a front view of the distribution machine of FIG. 7 at a second access door, with the second access door opened to reveal another bin and second baffle plates blocking access to adjacent bins.

With reference to FIGS. 7 through 10, the operation of the access doors 30 and additional features of the distribution machine 10 are shown. More specifically, FIGS. 7 and 8 illustrate two different access doors 30 associated with different sizes of bins 74 that may be formed by the platters 72 as previously described. Each of the access doors 30 is similarly sized and provides access when opened to the closed interior 14 through an opening 134 in the housing 12. When smaller sized bins 74 such as those shown in FIGS. 3 and 7 are used on a particular platter 72, the size of the opening 134 revealed by moving the access door 30 to the open position is larger than the size of the bins 74. In order to block unauthorized access into adjacent bins 74 that face at least partially towards the opening 134, a pair of solid blocking baffles 136 is positioned on opposite ends of the opening 134. The blocking baffles 136 are located immediately adjacent to the outer ends 118 of the divider plates 114 on either side of the bin 74 to be accessed, thereby preventing a user from reaching into adjacent bins 74 to divert additional medications or supplies from the platter 72. The blocking baffles 136 are rigidly coupled to the front wall 16 of the housing 12 to prevent displacement of the blocking baffles 136 by a user. Consequently, each of the platters 72 located on a particular level of the plurality of carousels 70 should be configured with similarly sized bins 74 such that the appropriate amount of access is granted through the opening 134 for all of the bins 74 located on that level.

As shown in FIG. 8, different access doors 30 may require openings 134 fitted with smaller blocking baffles 138. The smaller blocking baffles 138 of FIG. 8 are again rigidly coupled to the front wall 16 of the housing 12 to prevent unauthorized access from the opening 134 to bins 74 adjacent to the bin 74 holding the item or medication that has been authorized for removal. The bin 74 of this embodiment is a larger bin 74, such as the one shown and described in connection with FIG. 5 above. Thus, for layers of the plurality of carousels 70 with larger bins 74, the smaller blocking baffles 138 may be used to provide a complete opening through which the items in the larger bins 74 may be retrieved. For even larger bin sizes, it will be understood that the blocking baffles 136, 138 may be omitted entirely from the corresponding openings 134. The installation of the blocking baffles 136, 138 and the reconfiguration of platters 72 and bins 74 within the carousels 70 is consequently a joint operation conducted by authorized service personnel before the distribution machine 10 is placed into operation at a healthcare facility. As a result, the available portion of the opening 134 is set to be analogous to the size of the bins 74 on that particular level of the carousels 70, increasing the secured nature of all the other bins 74 within the closed interior 14.

FIGS. 7 through 10 also illustrate additional features of the access doors 30. As shown in the open position of these figures, each access door 30 includes a first end 142 pivotally coupled to the front wall 16 at a hinge 144 and a second end 146 opposite the first end 142. The second end 146 includes a door latch 148 configured to engage a latching mechanism 150 (partially visible in FIGS. 7 and 8 and described in further detail with reference to FIGS. 11A through 11D below) to retain the access door 30 in the closed position. The second end 146 may also include a sensor tine 152 configured to extend through a door sensor opening 154 for reasons set forth in further detail below. Each access door 30 is biased towards the open position by a biasing member such as a spring (not shown). This spring may be located at the hinge 144 for example. Each access door 30 also includes an exterior side 156 and an interior side 158 extending between the first and second ends 142, 146. An enclosure 160 projects from the interior side 158 of the access door 30 and encloses a digital camera 162 that faces inwardly towards the bin 74 adjacent to the access door 30 when the access door 30 is in the closed position. The field of vision of the camera 162 is schematically shown in phantom at reference number 164 in FIG. 9, although it will be understood from the following description that the camera 162 is not active when the access door 30 is in the open position. The camera 162 and its operation to detect whether any items are positioned within a particular bin 74 are described in further detail with reference to FIGS. 12A and 12B below.

Figure 9:
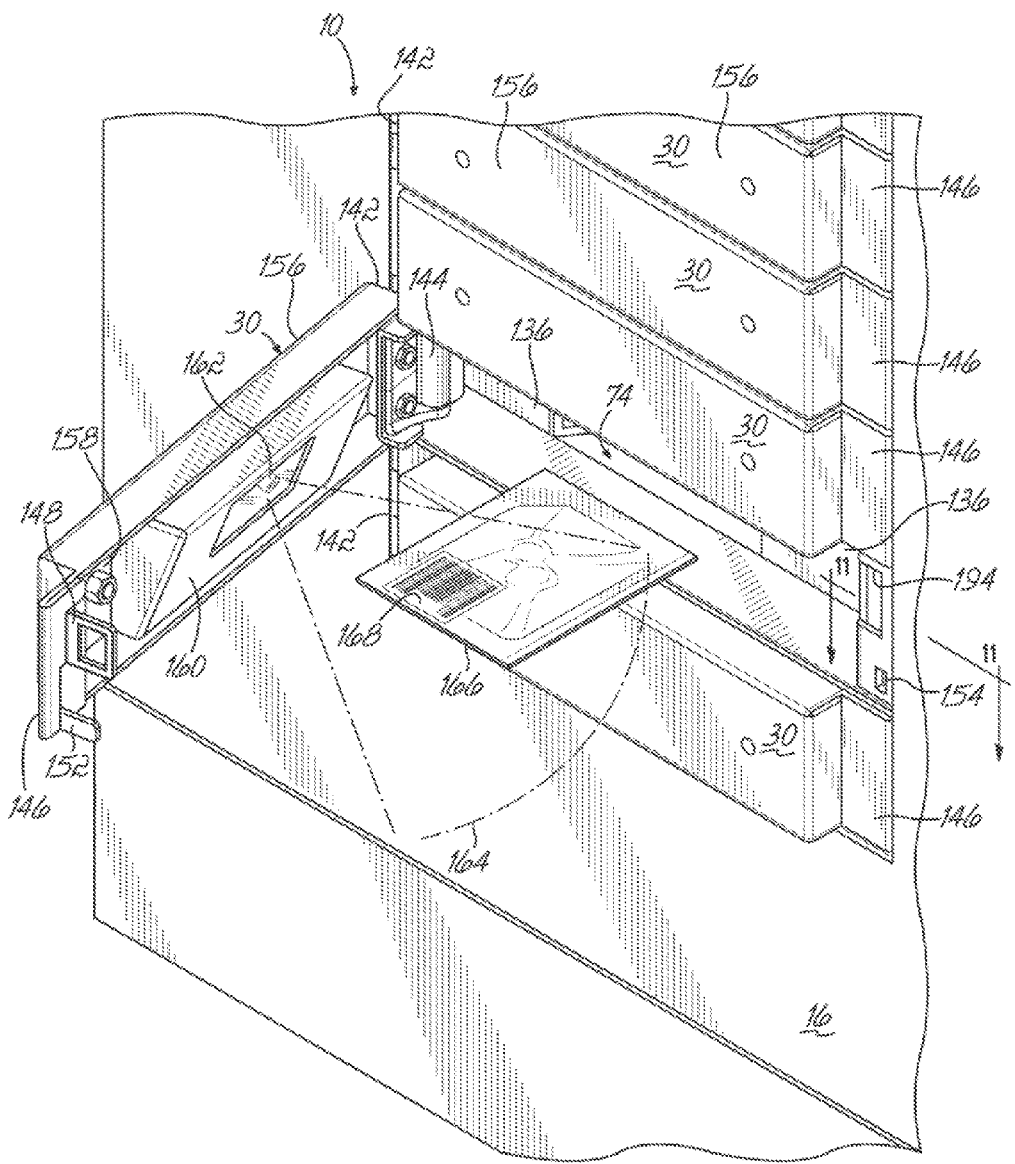
FIG. 9 is a perspective view of the distribution machine of FIG. 1, with an access door opened and a medication being removed from a bin adjacent the open access door.
Figure 10:
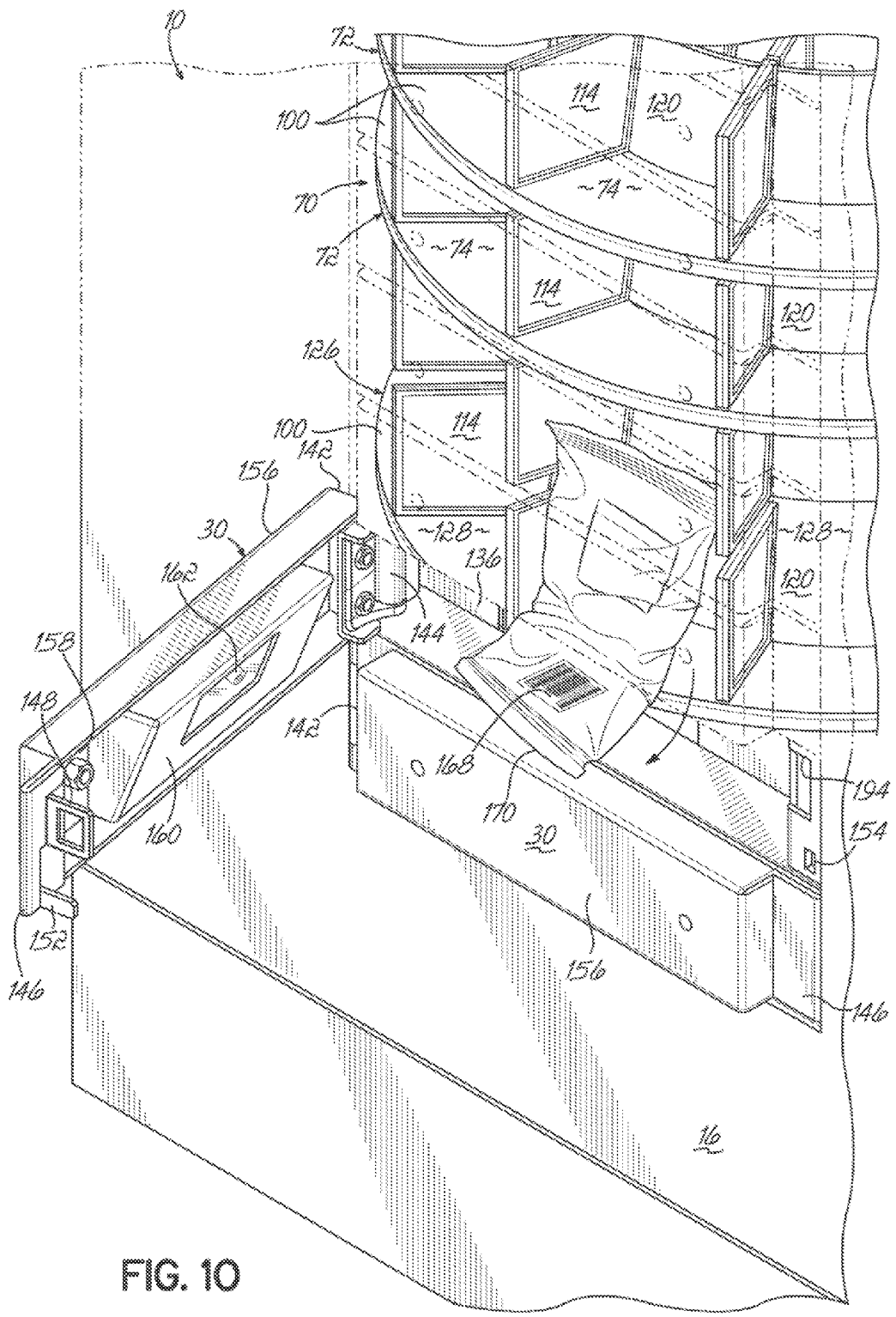
FIG. 10 is a perspective view of the distribution machine of FIG. 9, with a portion of the external structure shown in phantom to reveal a taller bin defined by two adjacent platforms on two adjacent carousels and configured to hold a larger item as shown.

Once the access door 30 has been opened as shown in FIGS. 9 and 10, the medication or item stored within the bin 74 adjacent to the opening 134 may be retrieved from the bin 74. It will be understood that once the access door 30 is opened, the retrieval and movement of an item is performed by the user with no active machine operation or intervention, such as would be present in dispensing mechanisms. With particular reference to FIG. 9, the item is a medication blister 166 containing a unit dose of a particular medication. The medication blister 166 is relatively small and thus can be positioned in a smaller bin 74, such as those described above with reference to FIG. 3. The medication blister 166 also includes machine readable indicia 168 such as a barcode 168 that can be detected by the barcode reader 58 shown in FIG. 1 on the exterior of the housing 12. Consequently, when a user removes the medication blister 166 from the bin 74, the removal of the correct medication blister 166 can be confirmed by scanning the machine readable indicia 168 prior to reclosing the access door 30. As described in further detail below, the latching mechanism 150 may be configured to prevent latching of the access door 30 until such a verification takes place.

Turning to FIG. 10, the item is a product bag 170 large enough in size to require placement in a taller combined bin 128 formed by first and second platters 72, 126 as previously described with reference to FIG. 6. The product bag 170 also carries machine readable indicia 168 such as a barcode 168 for detection by the barcode reader 58 following removal from the combined bin 128. As shown in FIG. 10, only the access door 30 adjacent the access door 30 adjacent the lowest of the platters 72 is opened and the product bag 170 must be pulled out through the corresponding opening 134 at the bottom of the combined bin 128. This door opening and retrieval process may be repeated for all of the medications and other items that are to be issued by the distribution machine 10 to a particular authorized user. Alternatively, it will be understood that the access door 30 adjacent the top platter 126 may be opened instead of the access door 30 adjacent the bottom platter 72 to provide access into the combined bin 128 for pulling the product bag 170 from the distribution machine 10.

It will also be understood that in additional embodiments, the access doors 30 adjacent both of the platters 72, 126 open simultaneously to provide a larger opening for retrieving the product bag 170. In such an embodiment, at least one of the access doors 30 that is configured to open simultaneously includes an extension (not shown) that replaces the relatively small piece of framing of the housing 12 normally present between adjacent access doors 30. This extension prevents unauthorized access to a bin immediately above or below the other access door 30 when that other access door 30 is opened independently (such as, for example, if the carousel 70 that moves to a location adjacent the access doors 30 now divides the combined bin 128 into two regular sized bins 74 as previously described. This extension serves a similar purpose as the stationary blocking baffles 136, 138 previously described in that this extension prevents unauthorized access to adjacent bins 74 that are not the bin 74 to be accessed by the user. Any number of the access doors 30 may be provided with these extension(s) when the distribution machine 10 is configured to have combined bins 128 at some location requiring more than one access door 30 to open simultaneously.

The machine readable indicia 168 on the medication blister 166 or product bag 170 may represent or include the National Drug Code (NDC) or a manufacturer's or repackager's NDC, UPC, or stock keeping unit (SKU) representing medication type, strength, tablet count, etc. Other information, coding methods, and unique medical item identifiers may also be used in other embodiments without departing from the scope of the invention, and these may be additional items of information automatically uploaded to memory during a restocking process described in detail below. Drug SKUs are assigned and serialized for inventory management at the source of medication blister 166 or product bag 170. One or more of the medication blisters 166 or product bags 170 stores in the bins 128 may have a common SKU.

Turning to FIGS. 11A through 11D, the operation and elements of the latching mechanism 150 are shown in further detail. As described above, the access door 30 is spring biased towards the open position and is selectively locked into the closed position by the latching mechanism 150. The latching mechanism 150 includes an engagement drum 174 rotatably supported about a pivot 176. The engagement drum 174 includes a periphery 178 defining at least one engagement notch 180 configured to receive the leading portion of the door latch 148 and a locking notch 182 configured to selectively engage a locking member 184 as described in further detail below. The engagement drum 174 is biased towards the unlocked position shown in FIG. 11A by a spring, which is illustrated in this embodiment as a torsion spring 186. Similarly, the locking member 184 is pivotally engaged with a lock bolt 188 that is normally spring biased towards the engagement drum 174 by a compression spring 190. This biasing of the compression spring 190 is selectively counteracted by a drive actuator 192 operatively connected to the lock bolt 188. In this regard, the drive actuator 192 includes a linear actuator or some other similar motor that operates with withdraw the lock bolt 188 and the locking member 184 away from the engagement drum 174 against the bias of the compression spring 190. The latching mechanism 150 also includes a latch aperture 194 located adjacent the engagement drum 174 and configured to receive the door latch 148 when the access door 30 is moved to the closed position. The latching mechanism 150 is therefore isolated substantially from a user even when the access door 30 is opened, thereby reducing the likelihood of tampering leading to unauthorized thefts or diversions.

Figure 11A:
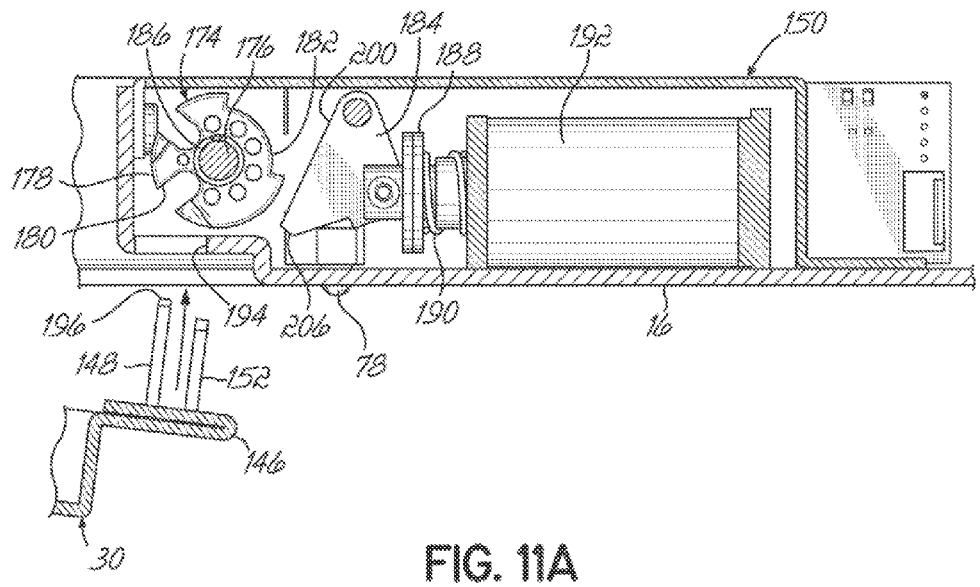
FIG. 11A is a cross-sectional top view of a door latching mechanism used with the access door of the distribution machine of FIG. 9, taken along line 11-11 with the access door in an opened position.
Figure 11B:
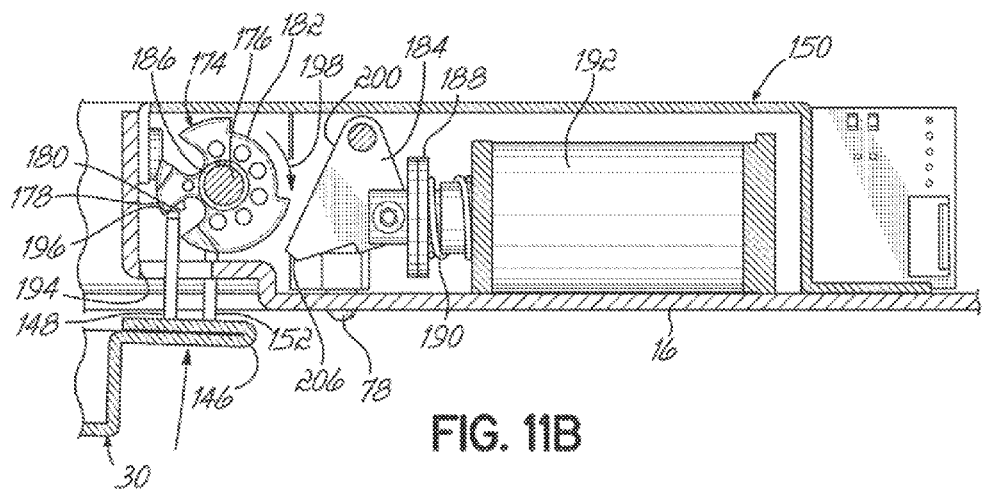
FIG. 11B is a cross-sectional top view of the door latching mechanism of FIG. 11A, with the access door closing without engagement of a lock member of the door latching mechanism.

When the access door 30 is in an unlocked and open position, the latching mechanism 150 is kept in the position shown in FIG. 11A. More particularly, the engagement drum 174 is rotated to the unlocked position by the torsion spring 186, in which one of the engagement notches 180 opens at least partially towards the latch aperture 194. Furthermore, the drive actuator 192 is actuated to hold the lock bolt 188 and therefore the locking member 184 away from the engagement drum 174 against the bias of the compression spring 190. During the normal course of operation for the distribution machine 10, the access door 30 is unlocked when a bin 74 containing an item to be retrieved is located adjacent the access door 30. The user must then manually retrieve the item from the bin 74 and scan the machine readable indicia 168 on the item with the barcode reader 58 to confirm removal of the correct item from the distribution machine 10. This process of item retrieval and scanning is user-driven and involves no active movement or dispensing operations of the machine 10. Until this verification scanning of the machine readable indicia 168 is performed, the drive actuator 192 continues to hold the locking member 184 out of engagement with the engagement drum 174. Consequently, if the user attempts to shut the access door 130 to actuate the latching mechanism 150 without verifying removal of the appropriate item, the access door 30 will not stay closed by virtue of the spring biases applied to the engagement drum 174 as well as the access door 30. This operation is shown in FIG. 11B, where a leading edge 196 of the door latch 148 is engaged with the engagement notch 180 in order to force the engagement drum 174 to rotate as indicated by arrow 198. Although the locking notch 182 on the periphery 178 of the engagement drum 174 will move past the locking member 184, the locking member 184 is prevented from engagement with the locking notch 182 by the drive actuator 192 in this state. The unsuccessful attempts to lock the access door 30 in the closed position will serve as a reminder cue to the user to scan the machine readable indicia 168 on the item.

Once that scan has been conducted by the barcode reader 58, a control signal is sent to the drive actuator 192 to release the withdrawing force applied to the lock bolt 188. As a result, the compression spring 190 forces the lock bolt 188 and the locking member 184 to move towards the engagement drum 174, thereby causing engagement of a leading edge 200 of the locking member 184 with the periphery 178 of the engagement drum 174 as shown by arrows 202 in FIG. 11C. In this state, the user again closes the access door 30 to insert the door latch 148 through the latch aperture 194, engage the leading edge 196 of the door latch 148, and force the engagement drum 174 to rotate as shown by arrow 204 in FIG. 11C. As long as the user closes the access door 30 with enough force, the engagement drum 174 will be forced to rotate away from the unlocked position enough to cause a shoulder 206 formed on the leading edge 200 of the locking member 184 to snap into engagement with the locking notch 182 on the engagement drum 174. The locking member 184 may rotate slightly as a result of this snap engagement as shown by arrow 208 in FIG. 11D, thereby producing a relatively flush and secure engagement of the shoulder 206 and the locking notch 182. The position shown in 11D is the locked and latched position of the latching mechanism 150 because the shoulder 206 of the locking member 184 forms a rigid block to rotation of the engagement drum 174 back towards the unlocked position, and the door latch 148 is hooked into engagement with the engagement notch 180 to prevent opening of the access door 30. When another authorized access event occurs and the access door 30 is to be opened, a control signal is sent to the drive actuator 192 to withdraw the lock bolt 188 and the locking member 184 from engagement with the engagement drum 174, which enables the spring biases on the engagement drum 174 and on the access door 30 to push the access door 30 to an opened position once again.

Figure 11C:
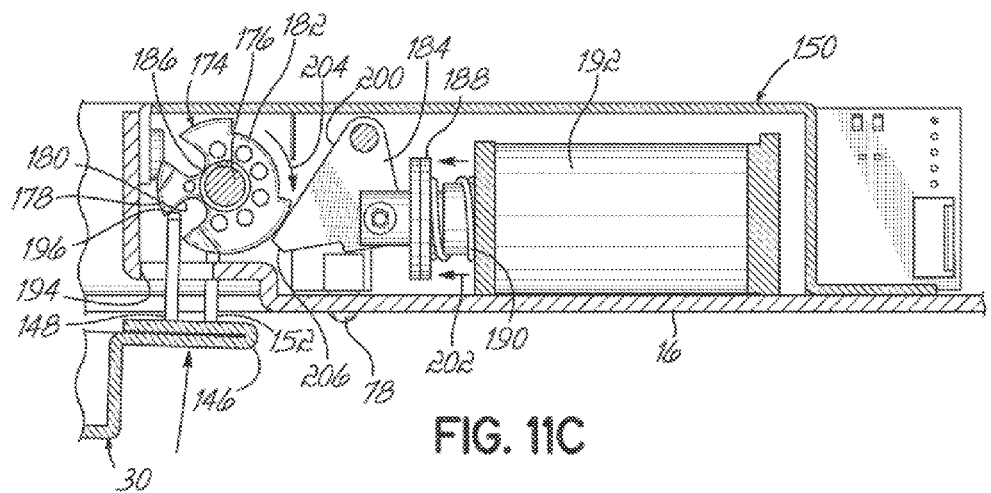
FIG. 11C is a cross-sectional top view of the door latching mechanism of FIG. 11B, with the access door closing during engagement of the lock member.
Figure 11D:
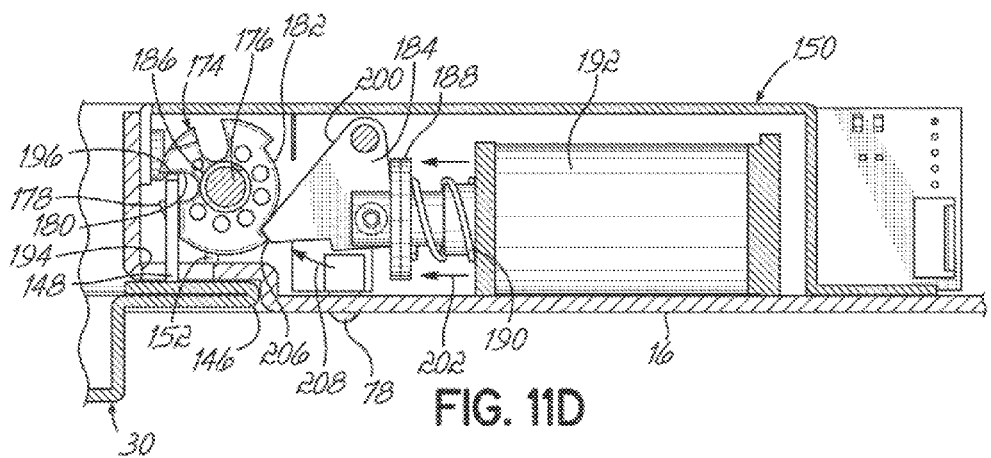
FIG. 11D is a cross-sectional top view of the door latching mechanism of FIG. 11C, with the access door in a closed and locked position by the door latching mechanism.

As previously described, the front wall 16 of the housing may include indicator lights 78 for actuation when the latching mechanism 150 is unlocked. The indicator light 78 for the latching mechanism 150 is positioned proximate to the locking member 184 within the latching mechanism 150 as shown in FIGS. 11A through 11D. The indicator light 78 may include a known light emitting diode or another conventional light source. FIGS. 11B through 11D further illustrate the entry of the sensor tine 152 on the access door 30 through the corresponding door sensor opening 154 in the latching mechanism 150. Although the sensor for detecting the entry of the sensor tine 152 is not shown in these figures, it will be understood that an optical interference sensor or some other similar sensor may be used to detect when the sensor tine 152 has entered the latching mechanism 150, which indicates that the access door 30 has been moved to the closed position. Feedback from this sensor as well as the drive actuator 192 enables a controller of the distribution machine 10 to reliably detect the open or closed status of each access door 30 at all times. Furthermore, this feedback can assist the controller in determining when to operate the digital camera 162 within the access door 30 as described in further detail below. Accordingly, the latching mechanism 150 cooperates with the controller of the distribution machine 10 to open and close the access doors 30 as required by the authorized access operational workflow described in detail below.

Figure 12A:
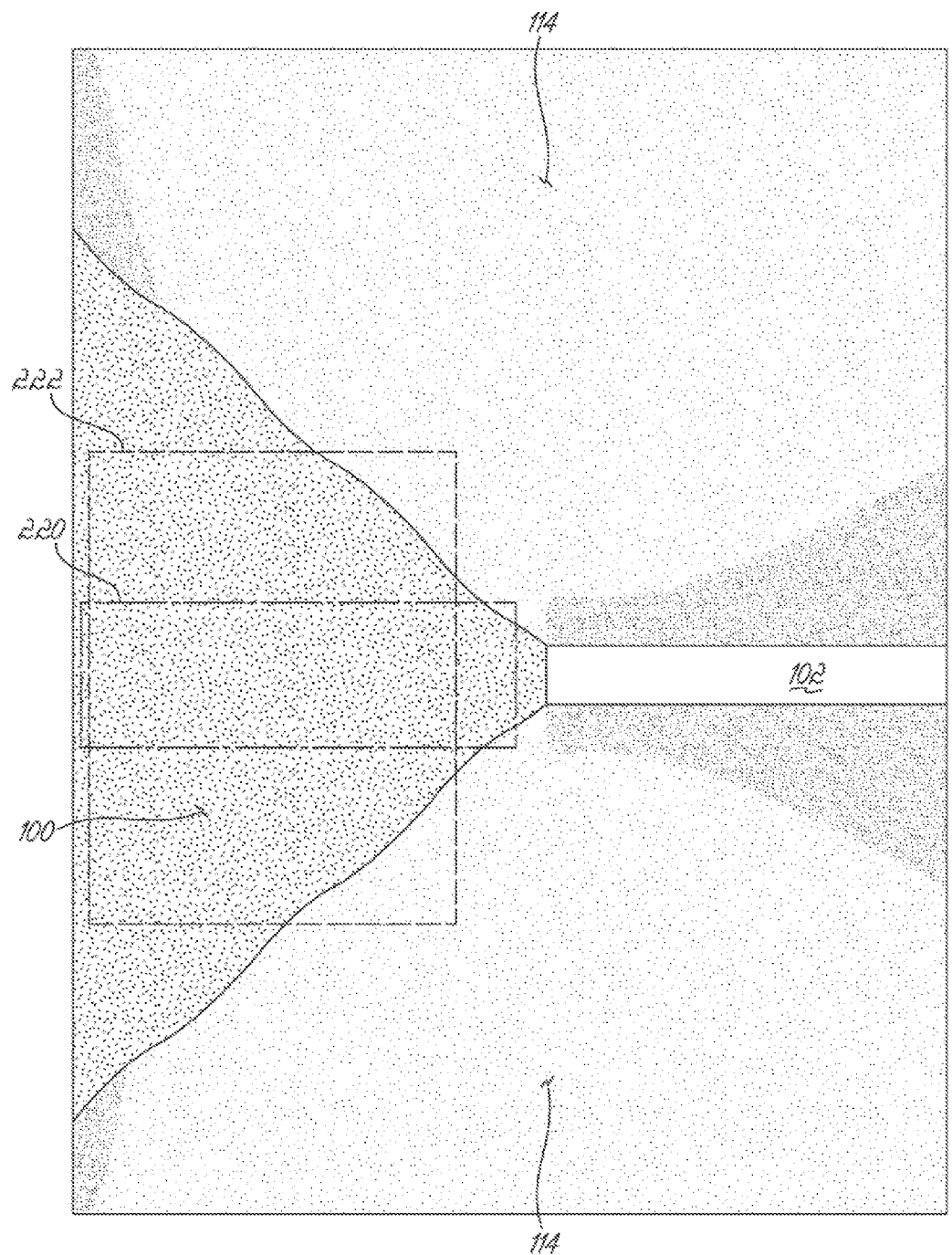
FIG. 12A is a schematic view of a first image detected by a camera located in one of the access doors of FIGS. 9 and 10, the first image revealing an empty bin.
Figure 12B:
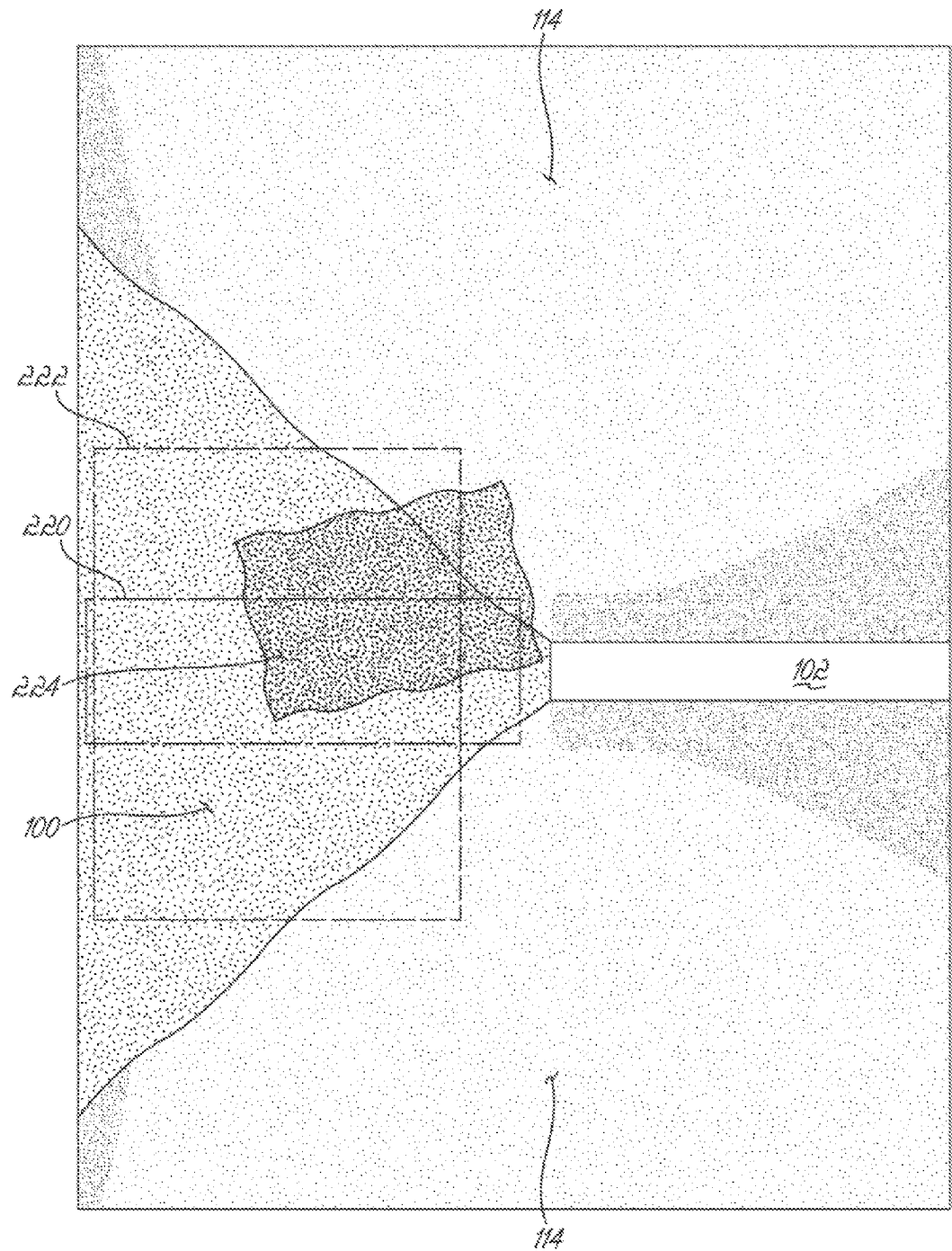
FIG. 12B is a schematic view of a second image detected by the camera of FIG. 12A, the second image revealing a bin with a medication or another item in the bin.

With reference to FIGS. 12A and 12B, the operation of the digital cameras 162 within the access doors 30 is further illustrated. More particularly, FIGS. 12A and 12B illustrate schematic representations of one exemplary output sensed by one of the digital cameras 162 when a corresponding bin 74 is empty (FIG. 12A) and when that bin 74 contains an item (FIG. 12B). Beginning with FIG. 12A, the camera 162 is operable to sense color differences in a field of pixels representing a digital image of the bin 74. For example, the bottom plate 100 of the platter 72 may be painted a different color (shown by different shading in FIG. 12A) than the remainder of the bin 74, which is defined by divider plates 114 and the hub periphery 112.

During an initial setup and calibration of the camera 162, an area of interest or AOI 220, 222 is selected that will be used to determine whether an item is present within the bin 74 or absent from the bin 74. One example of an AOI 220 shown in FIG. 12A is a longer narrower rectangle while the other example AOI 222 shown in FIG. 12A is a shorter broader rectangle. No matter what size and shape the desired AOI 220, 222 takes, the AOI 220, 222 should enclose a substantial portion of the bottom plate 100 because that is where the item will necessarily be located within the bin 74. The AOI 220, 222 may be calibrated and processed individually for each particular bin 74 or may be processed collectively for groups of similar bins 74. In addition, multiple smaller AOI's 220, 222 may be used in one particular image for a bin 74 to maximize the area pixilated and analyzed by the controller. The camera 162 is calibrated while the bin 74 is empty to provide the baseline color determination within the AOI 220, 222, as shown in FIG. 12A.

Turning to FIG. 12B, an item 224 is detectable within the bin 74 because the digital image taken by the camera 162 reveals a differently colored group of pixels at the location of the item 224. Once again, this different coloration is indicated by different shading in the figure. The chosen AOI 220, 222 is programmed with a set threshold (e.g., 10%), and this percent of the pixels within the AOI 220, 222 must change color from the baseline representation to indicate that an item 224 is located within the bin 74. As schematically shown in FIG. 12B, more than 10% of the AOI 220, 222 has changed color from FIG. 12A to FIG. 12B, and thus the output from the camera 162 will be conclusive that the item 224 remains within the bin 74. If multiple AOI 220, 222 are used within the same bin 74 as described above, each AOI 220, 222 is checked to determine if a threshold amount of color change in the pixels has occurred in any AOI 220, 222. Once the item 224 is removed, the detected image should once again return to a view substantially similar to FIG. 12A, which will enable the distribution machine 10 to detect that no items 224 remain within the bin 74. It will be understood that when multiple items are placed or stacked within a particular bin 74, the output received from the digital camera 162 is ignored by the controller until the bin 74 should be empty (i.e., when the last item was supposed to be removed by a user) because this exemplary output is only indicative of whether anything is located in the bin 74, not how many items or which items are in the bin 74. It will further be understood that while the schematic representations shown in FIGS. 12A and 12B show one possible set of exemplary outputs from the camera 162, the actual output may appear entirely different in other embodiments consistent with the current invention based on the programmed settings and characteristics of the particular camera 162 used.

In addition, it will be understood that the digital cameras 162 are also operable to take still or moving actual images of the bin 74 both before and after retrieval of an item. This output is in addition to the pixilated output described above, and these actual images/photographs are stored in the record of distribution of the medication along with other information such as the user, the intended patient, photographs of the user, and other information collected by the distribution machine 10. These additional images may also be analyzed to determine physical product characteristics of the items in the bin 74, including but not limited to color, shape, size, and any human readable print on the packaging of the medication. However, the camera 162 is generally not scanning any machine readable indicia such as a barcode either on the items themselves or on the bins 74, should those indicia be present. Thus, in one example, the digital camera 162 is actuated to take a still photograph of the bin 74 with the medication when the bin 74 initially arrives adjacent the access door 30, then actuated again to take an image that will be pixilated and analyzed as well as another still photograph of the bin 74 following retrieval of the medication and closing of the access door 30. It will be understood that the operation of the digital camera 162 following closing of the access doors 30 may be delayed until after each of the medications desired for one particular user have been retrieved, so that the process of retrieving the medications is streamlined (however, the machine must then rotate each of these bins 74 back to the doors 30 and associated digital cameras 162 to perform the imaging and analysis).

Figure 13A:
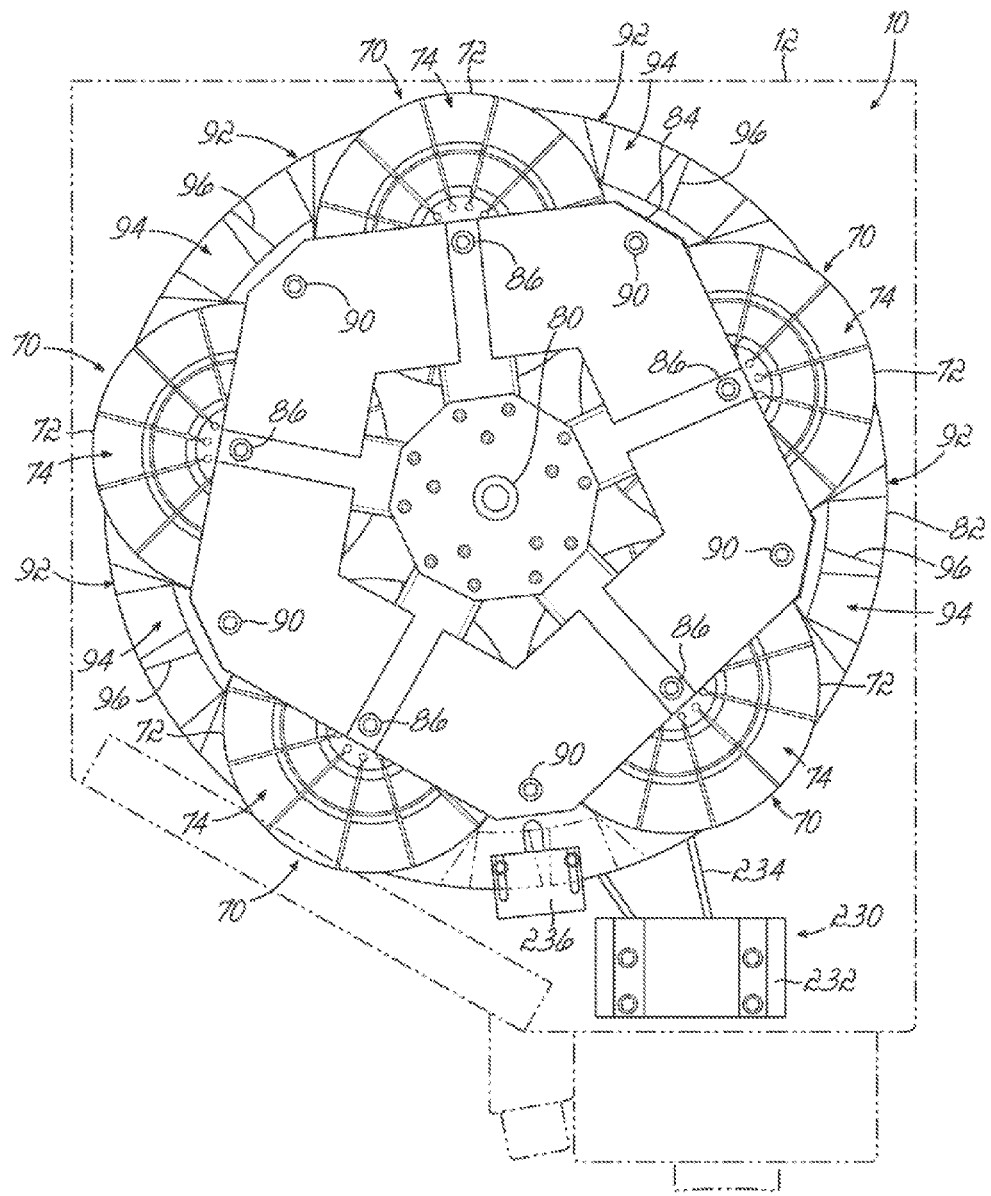
FIG. 13A is a top view of the distribution machine of FIG. 1, with the housing shown in phantom to illustrate portions of a drive mechanism used to move the carousels and the platforms.
Figure 13B:
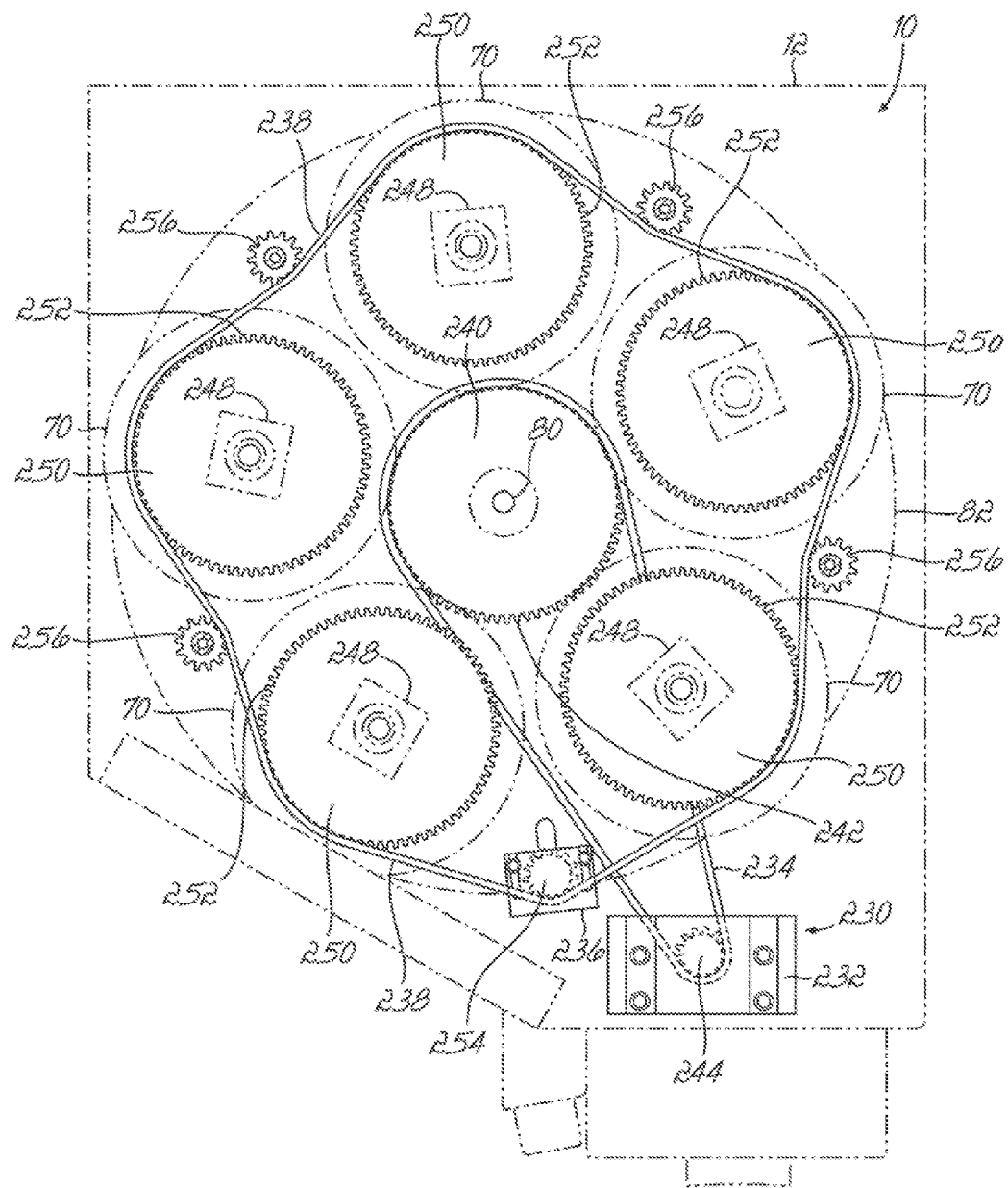
FIG. 13B is a cross-sectional top view of the distribution machine of FIG. 13A, with further portions of the carousels and a bottom support plate shown in phantom to illustrate a serpentine belt drive used with the drive mechanism.
Figure 13C:
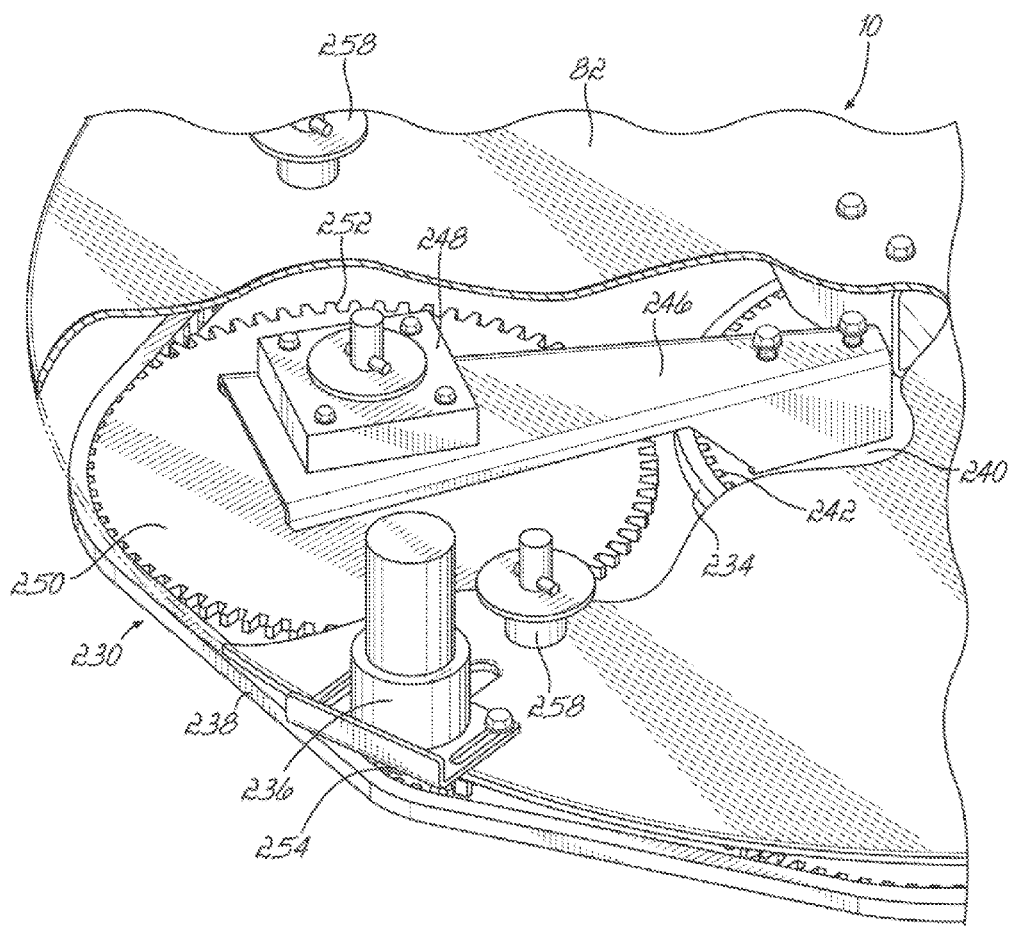
FIG. 13C is a detailed perspective view of the distribution machine of FIG. 13B, with a portion of the bottom support plate shown in phantom to illustrate support features of the bottom support plate and a drive motor used with the serpentine belt drive.

With reference to FIGS. 13A through 13C, the drive mechanism 230 associated with the exemplary embodiment of the distribution machine 10 is shown. The drive mechanism 230 is located adjacent the bottom support turntable 82 of the plurality of carousels 70 and is operable to rotate the plurality about the central drive axle 80 as well as the individual carousels 70 about the respective carousel drive axles 86. Positioning the drive mechanism 230 mostly beneath the bottom support turntable 82 substantially prevents any accidentally dropped items from interfering with continued operation of the plurality of carousels 70.

FIG. 13A illustrates a top view of the plurality of carousels 70, once again showing the relative locations of the central drive axle 80, the carousel drive axles 86, and the support rods 90 that extend from the top connection plate 84 to the bottom support turntable 82. Also shown in FIG. 13A, the drive mechanism 230 includes a first drive motor 232 configured to move a first serpentine belt 234 and a second drive motor 236 configured to move a second serpentine belt 238 (not shown in FIG. 13A). The first drive motor 232 actuates movement about the central drive axle 80, while the second drive motor 236 actuates movement about the carousel drive axles 86.

With reference to FIG. 13B, the carousels 70 and the bottom support turntable 82 have been removed and shown in phantom, respectively, in order to reveal the drive components located underneath the bottom support turntable 82. FIG. 13C illustrates several of these same elements in a perspective view for further clarity. To this end, the central drive axle 80 extends through the bottom support turntable 82 and is coupled to a central drive gear 240 located beneath and spaced from the bottom support turntable 82. The central drive gear 240 includes a toothed periphery 242 that engages with the first serpentine belt 234. The first drive motor 232, which is mounted at a fixed location within the closed interior 14 and spaced from the plurality of carousels 70, further includes a first output gear 244 that also engages with the first serpentine belt 234 as shown in FIG. 13B. Thus, as the first drive motor 232 rotates the first output gear 244, that rotation is transmitted via the first serpentine belt 234 to the central drive gear 240 and to the central drive axle 80. In addition to the previously-described connection between the central drive axle 80 and the top connection plate 84, the rotation of the central drive gear 240 is transmitted to the plurality of carousels 70 by a series of radially extending supports 246 extending outwardly from the central drive gear 240 and coupled to the central drive gear 240 and the bottom support turntable 82. These supports 246 are shown in FIG. 13C and are located directly underneath the bottom support turntable 82. Consequently, the first drive motor 232 actuates rotation of the entire plurality of carousels 70 via the first serpentine belt 234, the central drive gear 240, and the central drive axle 80.

Also shown in FIG. 13C, each of the carousels 70 is supported by a generally rectangular bearing box 248 positioned on top of the bottom support turntable 82. The carousel drive axle 86 (not shown in FIG. 13C) extends through an aperture in the bearing box 248 and in the bottom support turntable 82 to be coupled to a carousel drive gear 250 located underneath the bottom support turntable 82. Each of the carousel drive gears 250 has a toothed periphery 252 that engages with the shared second serpentine belt 238. Between one of the pairs of adjacent carousels 70, the second drive motor 236 is mounted on the bottom support turntable 82. The second drive motor 236 is connected to a second output gear 254 also engaged with the second serpentine belt 238. Thus, as the second drive motor 236 rotates the second output gear 254, this rotation is transmitted to movement of the second serpentine belt 238 and corresponding individual rotations of each of the carousel drive gears 250 and carousels 70. To this end, each of the carousels 70 is rotated about the corresponding carousel drive axle 86 simultaneously whenever one of the carousels 70 requires rotation to align a bin 74 with a particular access door 30. Each of these components associated with the rotation of each carousel 70 rotates with the bottom support turntable 82 whenever the first drive motor 232 rotates the plurality of carousels 70 collectively. Furthermore, it is clear from FIG. 13C that each of the radially extending supports 246 is thicker adjacent the central drive gear 240 than near the carousels 70 such that each of these drive components (second serpentine belt 238, carousel drive gears 250, second output gear 254 are located higher in elevation than the first serpentine belt 234, thereby enabling clearance of these elements when the entire plurality of carousels 70 rotates about the central drive axle 80.

Between each pair of adjacent carousels 70 other than where the second drive motor 236 is located, an idler gear 256 is mounted beneath the bottom support turntable 82 for maintaining tension and positioning of the second serpentine belt 238 around each of the carousel drive gears 250. FIG. 13C also illustrates that each of the support rods 90 connects to the bottom support turntable 82 via a support base 258 (for supporting the support rods 90 and the partial carousels 92) located just radially inwardly from the idler gears 256 or the second drive motor 236. In sum, the drive mechanism 230 accomplishes the rotation of each carousel 70 about both the central drive axle 80 and about the corresponding carousel drive axle 86 with only two stationary mounted drive motors 232, 236 and two serpentine belts 234, 238. This drive mechanism 230 advantageously reduces the number of moving drive elements that could become worn or broken, thereby limiting the amount of time that the distribution machine 10 is inactive for maintenance or repairs.

Figure 14:
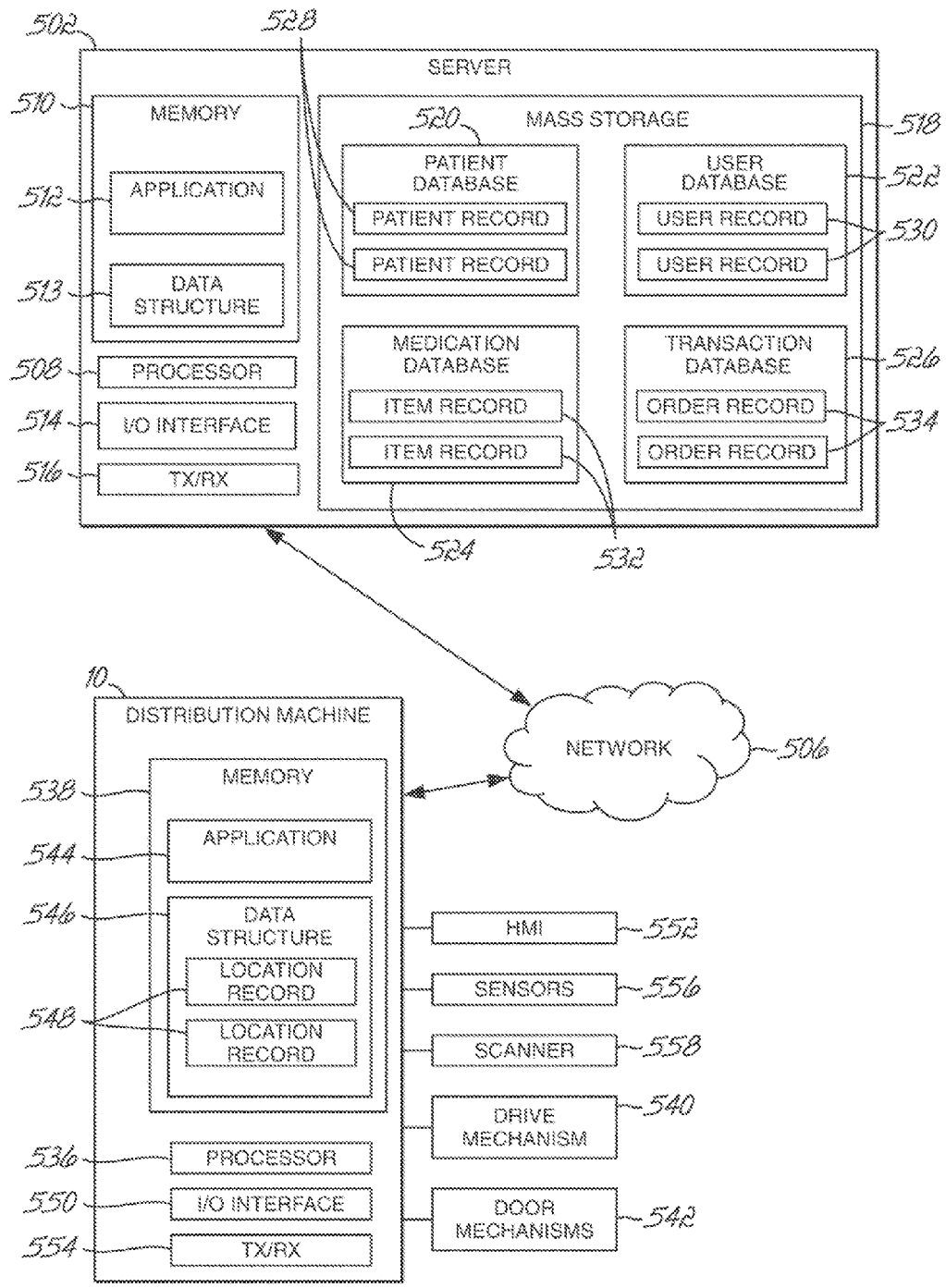
FIG. 14 is an exemplary block diagram of a system including the distribution machine of FIG. 1 and a server consistent with some embodiments of the invention.

Referring now to FIG. 14, this figure provides a block diagram illustrating a system including a medical information server 502 and the distribution machine 10. As shown, the medical information server 502 may be in communication with the distribution machine 10 over a communication network 506. The communication network 506 may be a wide area network (WAN), a local area network (LAN) and/or other such types of communication networks, including for example, a cellular communication network. Furthermore, the medical information server 502 and the distribution machine 10 may communicate over the communication network 506 using a wired and/or wireless connection.

Consistent with embodiments of the invention, the medical information server 502 may generally comprise one or more interconnected computing systems, where the server 502 generally includes at least one processor 508 and at least one memory 510. The memory 510 generally includes at least one application 512 stored thereon, where the application 512 generally comprises one or more instructions stored as program code that may be read from the memory 510 by the processor 508 and which may cause the processor 508 to perform one or more operations when executed by the processor 508 to thereby perform the steps necessary to execute steps, elements, and/or blocks embodying the various aspects of the invention. As such, the routines and/or instructions which may be executed by the processor 508 to implement embodiments of the invention, whether implemented as part of an operating system or a specific application, component, program, object, module, or sequence of operations executed by the at least one processor 508 will be referred to herein as "computer program code" or simply "program code."

In addition, the medical information server 502 may include an input/output (I/O) interface 514, where the I/O interface 514 may be configured to receive data from input sources and output data to output sources. For example, the I/O interface 514 may receive input data from a user input device such as a keyboard, mouse, microphone, touch screen, and other such user input devices, and the I/O interface 514 may output data to one or more user output devices such as a computer monitor, a touch screen, speakers, and/or other such output devices that may be used to output data in a format understandable to a user. As such, in some embodiments of the invention, user input data may be communicated to the processor 508 of the medical information server 502 using a user input device such as a keyboard or touch screen utilizing the I/O interface 514. The medical information server 502 may include at least one transceiver (Tx/Rx) 516, where the processor 508 may cause data to be transmitted and/or received over the communication network 506 using the transceiver 516.

Consistent with embodiments of the invention, the medical information server 502 may include a mass storage memory device 518. While in FIG. 14, the memory 510 and mass storage memory device 518 are illustrated as separate memory devices, the invention is not so limited. For example, the memory 510 and the mass storage memory device 518 may comprise one storage device and/or a plurality of storage devices. The memory 510 and the mass storage memory device 518 may represent random access memory (RAM) comprising the main storage of a computer, as well as any supplemental levels of memory, e.g., cache memories, non-volatile or backup memories (e.g., programmable or flash memories), read-only memories, etc. In addition, a memory may be considered to include memory storage physically located elsewhere, e.g., cache memory in a processor of any computing system of the medical information server 502, as well as any storage device on any computing system in communication with the medical information server 502 (e.g., a remote storage database, a memory device of a remote computing device, etc.).

In addition, the mass storage memory device 518 may include one or more databases 520-526, where the databases 520-526 may store data records corresponding to information utilized by the medical information server 502 and/or distribution machine 10 consistent with some embodiments of the invention. For example, the mass storage memory device may store a patient database 520, where the patient database may include one or more patient records 528. Each patient record may include data corresponding to a particular patient, including for example, a unique identifier associated with the patient, the patient's name, date of birth, social security number, gender, allergies, room number at a health care facility, attending physician, prescribed medications, prescription schedule, medical item distribution information (e.g., each medical item distributed to the patient, the time of the distribution, the user who ordered the distribution) and/or other such information.

The mass storage memory device 518 may also include a user database 522, where the user database 522 may store one or more user records 530. Each user record 530 may include data corresponding to a particular user of the distribution machine 10 such as a nurse, physician, and/or pharmacist at a healthcare facility where the distribution machine 10 is located. In some embodiments of the invention, each user record includes information for the particular user, including for example, a unique identifier associated with the particular user, a class associated with the particular user, the particular user's name, the particular user's job title, a unique security code for the particular user, one or more identifying characteristics corresponding to the particular user (e.g., a biometric feature of the particular user such as a fingerprint scan, retina scan, palm scan, voice sample recording, and/or other such identifying characteristics), a key code for the particular user, medical item distribution information (e.g., each medical item distributed to the particular user, the time of the distribution, the patient for which the distribution was requested, medications the particular user is authorized to receive) and/or other such information.

The mass storage memory device 518 may also include a medication database 524, where the medication database 522 may store one or more item records 532. Each item record 532 may include data corresponding to a particular medical item that may be stocked in the distribution machine 10. For example, an item record may correspond to a particular type of medication that may be stored in the distribution machine 10, and the item record may include information related to the particular medication such as the name of the medication, the vendor of the particular medication and purchasing information, other medications known to react with the particular medication, an image of the particular medication, recommended doses of the particular medication and/or other such information.

The mass storage memory device 518 may also include a transaction database 526, where the transaction database 526 may store one or more order records 534. Each order record may include data corresponding to a particular medical item order for the distribution machine 10. For example, an amount of a particular medical item may be ordered by a healthcare facility at which the distribution machine 10 is located, and a record of the transaction may be stored in the transaction database 526. An order record 534 may include the types and quantities of medication purchased, the healthcare facility for which the order was placed, the distribution machine 10 for which the order was placed and/or other such information.

As shown in FIG. 14, the distribution machine 10 includes at least one processor 536 and at least one memory 538. As discussed herein, the distribution machine 10 is configured to distribute medical items stored in secure storage locations to a user. Consistent with embodiments of the invention, the distribution machine includes a drive mechanism 230, which may rotate one or more platters 72 having a plurality of storage bins 74 to a desired position for access by a user (as described above), such that the user may retrieve a medical item stored in a particular storage bin 74. Furthermore, to secure access to the storage bins 74, the distribution machine 10 includes a plurality of lockable access doors 30 where access may be controlled by a plurality of latching mechanisms 150. In embodiments consistent with the invention, the processor 536 may control the drive mechanism 230 and the latching mechanisms 150 such that access to desired medical items may be controlled through the processor 536.

The memory 538 of the distribution machine 10 generally includes at least one application 544, where application 544 includes instructions stored as program code that may be executed by the processor 538 to perform one or more operations consistent with some embodiments of the invention. As shown, the memory 538 may include a data structure 546 which stores location records 548 which include information corresponding to the plurality of storage locations (e.g., bins 74) of the distribution machine 10. Each location record 548 may include the type of medical item stored at the particular storage location, the quantity stored at the particular location, the dosage of the medical item, the expiration date of the medical item, the lot number of the medical item and/or other such information corresponding to the medical item.

Consistent with some embodiments, the distribution machine 10 may include an I/O interface 550 for interfacing with user input and output devices such that the processor 536 may receive data from one or more user input devices and output data to one or more user output devices. As shown in the block diagram, the distribution machine 10 may include a human/machine interface (HMI) 552, where the HMI 552 generally refers to a user input device and a user output device. One exemplary HMI 552 was described above in connection with FIG. 1 (e.g., the user interface 32, the display screen 34, the keyboard 36, the barcode reader 58, etc.). In another example, the HMI 552 may comprise a touch screen where a user may input data to the distribution machine 10 by touching the screen and the user may receive output data from the distribution machine 10 via images rendered on the touch screen. In some embodiments, the HMI 552 may comprise a keyboard or other such user input device and a monitor or other such user output device. Consistent with some embodiments of the invention, the HMI 552 may include one or more user input devices which allow a user to input data corresponding to one or more identifying characteristics. For example, the HMI 552 may include a fingerprint scanner such that the user may input a fingerprint scan to the distribution machine 10 using the fingerprint scanner. Other such examples of devices for inputting biometric data include a retina scanner, a hand scanner, a microphone for capturing a voice sample, a camera for inputting a still and/or live image of the user and/or other such devices.

The processor 536 may receive input data from the HMI 552 through the I/O interface 550, and likewise the processor 536 may output data to the HMI 552 through the I/O interface 550. A user may thereby interact with the medical device 10 and more specifically with the application 544 executing on the processor 536 to thereby cause the distribution machine to allow access to one or more storage locations in response to data input by the user using the HMI 552. A user may thereby interact with the distribution machine 10, input various identifying data, and receive feedback responsive to the interaction via the I/O interface 550, the HMI 552 and the processor 536.

In one embodiment, the user may need to provide several different types of identifying data to the processor 536 via the HMI 552 in order to gain access to the storage locations. For example, the user may need to enter a non-confidential user identifier (ID) and a confidential personal identification number (PIN) as user identification data. The PIN represents a security code in the form of a secret numeric password shared between the user and distribution machine 10, and can be used to authenticate the user to the distribution machine 10. Upon receiving the user identification data, the processor 536 verifies that the user ID corresponds to a particular user records, and looks up the PIN based upon the user ID and compares the looked-up PIN with the received PIN. The user is granted access to the distribution machine 10 only when the number entered matches with the number stored in the user record. The user may need to enter additional input data from a tertiary device, such as a fingerprint scanner, or answer a secret question using a keyboard in order to be authenticated.

The distribution machine 10 may also include a transceiver (Tx/Rx) 554. The transceiver may be utilized by the processor 536 to communicate data over the communication network 506. Hence, in some embodiments of the invention, a user may interact with the distribution machine 10 via the HMI 552, and the processor 536 may send and receive data to and from the medical information server 502 to determine whether to allow access to the distribution machine in general and/or to a particular medical item stored in the distribution machine 10. For example, a user may input identification data through the HMI 552, and the application 544 executing on the processor 536 may cause the processor to communicate with the medical information server 502 over the communication network 506 using the transceiver 554 to determine whether the user identification data corresponds to a user record 530 and also to determine whether to allow access to a particular medical item stored in the distribution machine based on the input identification data and/or a user record 530.

In some embodiments consistent with the invention, the distribution machine 10 may include one or more sensors 556. The sensors 556 may be positioned in the distribution machine such that the sensors 556 may detect whether a medical item is in a storage location positioned for access or whether the medical item has been removed from the storage location. For example, a sensor 556 may comprise a digital camera (i.e., camera 162) positioned such that it may capture an image of a storage location positioned proximate an access door 30 of the distribution machine 10 for access to a medical item stored in the particular storage location. In this example, the application 544 executing on the processor 536 may cause the processor 536 to use the camera to capture an image of the storage location in response to an access door 30 being opened and closed. The image data may be stored in the user database, the patient database and/or the transaction database, where the image data may be included in a record associated with the distribution of a medical item from a storage location by the user. In addition, the image may be analyzed by the processor 536 to determine whether the medical item was removed from the storage location by a user and/or whether any quantity of medical items is remaining in the storage location, such as when multiple items are stored in a single storage location. Furthermore, a camera may be positioned on the distribution machine 10 to capture image data of a user of the distribution machine while the user is interacting with the distribution machine 10 to receive one or more medical items. The image data of the user may be stored in the user database, the patient database, and/or the transaction database, where the image data may be included in a record associated with the distribution of one or more medical items to the user. While the sensors 556 have been described as being cameras, the invention is not so limited. Other types of sensors such as laser, radio frequency and/or other types may be utilized in the distribution machine 10.

The distribution machine 10 may also include a scanner 558. The scanner 558 may be positioned on the distribution machine 10 such that a user may scan a machine readable indicia using the scanner 558 to confirm removal of an item, confirm the type of medical item (e.g., scanning the machine readable indicia may confirm that the correct medication was distributed), input a unique code associated with a user (e.g., a unique key card with machine readable indicia may be scanned with the scanner), and/or other such purposes. The barcode reader 58 associated with the exemplary embodiment shown in FIG. 1 is one example of such a scanner 558. For example, a user may scan machine readable indicia associated with a removed medical item using the scanner 558 to confirm removal of the medical item by the user. In this example, after making a medical item in a particular storage location accessible to the user, the application 544 executing on the processor 536 may cause the processor to prompt the user to scan the medical item using the HMI 552. In response to the user scanning the medical item, the user may be informed via the HMI 552 that the medical item is the correct type requested by the user and data indicating that the user removed the medical item from the particular storage location may be stored in the data structure 546 of the distribution machine 10 and/or one or more databases 520-526 of the medical information server 502.

Figure 15:
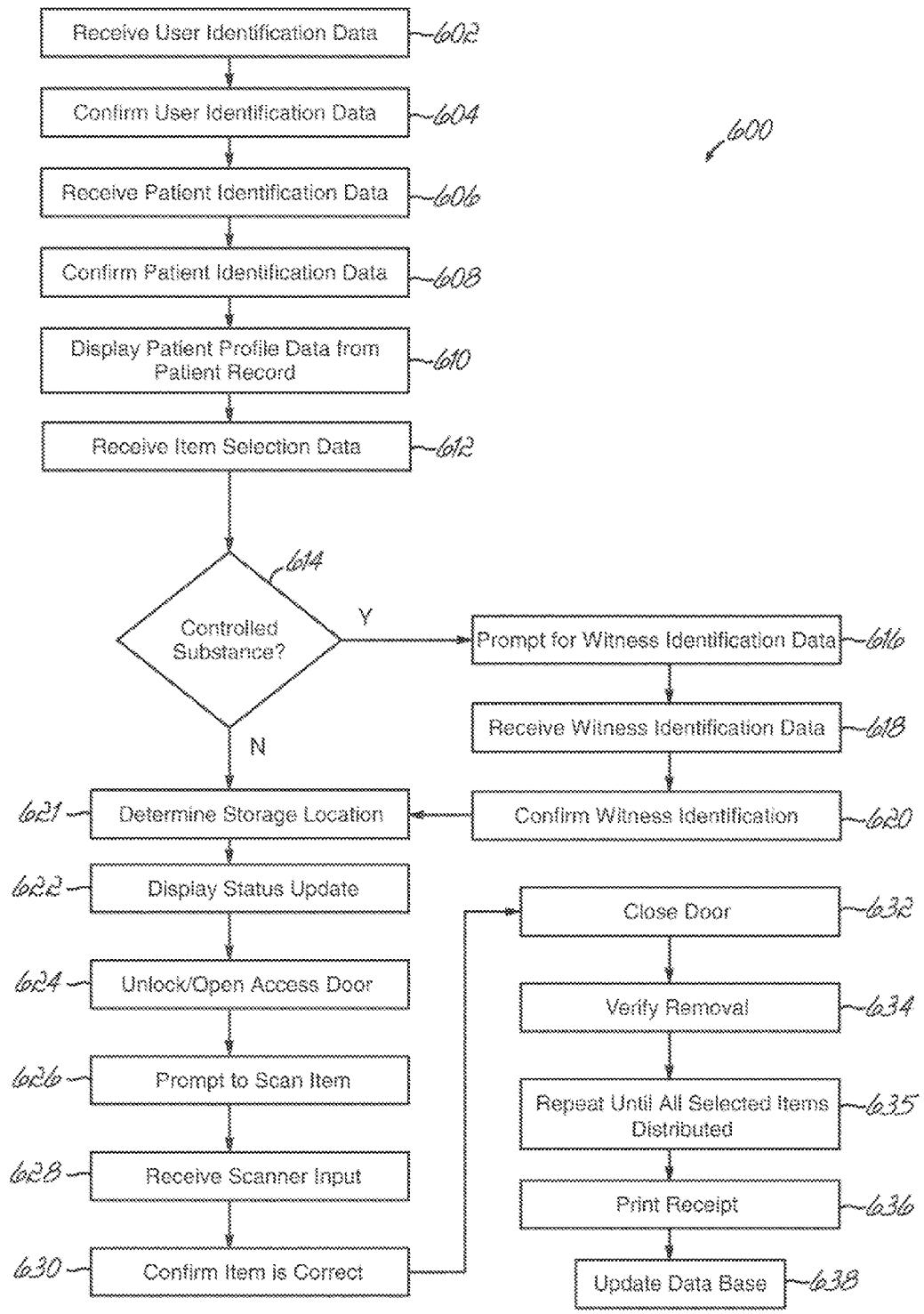
FIG. 15 is a flowchart illustrating a sequence of operations that may be performed by the distribution machine of FIG. 1 to distribute one or more medical items.

Referring now to FIG. 15, a flowchart 600 is provided which illustrates a sequence of operations that may be performed by a distribution machine consistent with embodiments of the invention to selectively distribute one or more medical items from the distribution machine to users for use with patients. A user may log in to the distribution machine by inputting identification data associated with the user, and a processor of the distribution machine may receive the user identification data (block 602). In some embodiments, the distribution machine may include user input and output devices which may present the user with a graphical user interface to facilitate the input and output of data to the user. The processor determines whether the user identification data corresponds to an authorized user (block 604). As discussed above, with respect to FIG. 14, a user database may include a plurality of user records corresponding to authorized users of the distribution machine. As such, the user identification data received by the processor may be checked against the user database to determine whether the user identification data corresponds to a particular user record, and whether any security codes or identification characteristics input by the user match the expected values stored in a particular user record.

The user may enter patient identification data, and the processor may receive the patient identification data (block 606). As stated above, the distribution machine may include an HMI which presents the user with a graphical user interface. For example, the distribution machine may include a touch screen as a display, and the user may be able to select a patient from a list of patients, search for a patient by last name, search for a patient by room number and/or other such information that may identify a particular patient. The processor may determine whether a patient record corresponds with the patient identification data, and the processor may prompt the user through the HMI to confirm that the located patient record is the correct patient record (block 608). Following confirmation, patient profile data stored in the patient record may be displayed for the user (block 610). Patient profile data may include for example, the patient's name, room number, attending physician, attending nurse(s), prescribed medications, medication dosage schedule, associated medical items allergies and/or other such information.

The user may select a particular medical item associated with the identified patient's profile using the HMI. For example, the user may select one or more medications prescribed to the patient as indicated on the display of the distribution machine. Item selection data is received by the processor (block 612), and the processor determines whether the selected medical item indicated by the item selection data is a controlled substance (block 614). In some embodiments, government regulations may limit the distribution of medications, where these medications may be considered "controlled substances." For example, the United States Drug Enforcement Agency (DEA) issues a controlled substances list. In embodiments of the invention, depending on various government regulations, medications stored in the distribution machine may be considered controlled substances. Whether or not a particular medication is a controlled substance may be stored in a medication record of a medication database connected to the distribution machine, such that a processor of the distribution machine may communicate with the medication database to determine whether a particular medication is a controlled substance.

Furthermore, the medication record may include data indicating a class associated with the medication, where the class may cause the distribution machine to perform one or more particular operations. The class may indicate a schedule class for each medication according to the U.S. DEA controlled substances list, where certain protocols may be required for different medications based on the schedule class, and the medication record may indicate such U.S. DEA scheduled class. Also, a medication record may indicate that a class associated with a medication indicates that the medication is unsafe for handling without safety equipment such as gloves. The processor of the distribution machine may output a warning on the graphical user interface indicating such warning to the user in response to a user selecting the medication for distribution. In another example, a medical record may indicate that a class associated with a medication indicates that the medication is a sensitive therapy medication requiring special dosing instructions or dosing limits, and data may be output by the processor to the graphical user interface to inform the user that the medication is a sensitive therapy medication, inform the user of special dosing instructions, and/or indicate the dosing limits for the medication with respect to a particular patient. As such, a medication record may include data indicating one or more classes for the particular medication corresponding to the medication record, where the class may cause the distribution machine to perform one or more operations in response to a user selecting the particular medication for distribution.

In response to determining that the medical item is a controlled substance ("Y" branch of block 614), the processor may cause the HMI to prompt the user for a witness (i.e., another person to witness the distribution of the medical item) (block 616). The witness may utilize the HMI to input identification data, and the processor may receive the witness identification data (block 618). Similar to the process described above with respect to identifying a user, the witness identification data may be checked against the user records to determine whether the witness is an authorized user and whether the witness is authorized to receive the particular medical item. In some embodiments, each user may have an associated authorization level stored in the corresponding user record, where the authorization level generally relates to different levels of medical items that the user is authorized to receive and/or witness the reception of. As such, the processor may confirm the identity of the witness and confirm that the witness is authorized to witness distribution of the selected medical item (block 620).

In response to determining that the selected medical item is not a controlled substance ("N" branch of block 614), or after confirming that the witness is authorized to serve as a witness (block 620), a storage location storing the selected medical item is determined by analyzing a plurality of location records, where each location record is associated with a particular storage location in the distribution machine (block 621). As described previously, a location record may include the expiration date and the lot number for the stored medical item. As such, embodiments of the invention may determine a particular medical item to distribute based on the expiration date and/or the lot number. For example, if a user selected a first type of medical item for distribution, and the distribution machine stored a plurality of medical items of the first type, determining the particular medical item of the first type to distribute may be based on the expiration dates of each medical item of the first type. In this example, the particular medical item selected for distribution may be the medical item of the plurality having the earliest expiration date indicated by the location record. Similarly, determining the particular medical item of the first type to distribute may be based on the lot numbers of each medical item of the first type, such that a lot number associated with medical items stocked in the machine earlier than other lot numbers would be distributed earlier (i.e., medical items stocked first are distributed first based on the lot numbers associated with the medical items).

The HMI displays a status update to the user indicating that the selected item is being positioned for removal (block 622). The processor of the distribution machine actuates one or more of the drive mechanisms to position the storage location of a carousel behind an access door such that the storage location may be accessed by the user through the access door, and the processor communicates with a door mechanism associated with the access door to unlock and/or open the access door (block 624). The processor outputs a prompt on the HMI to the user to scan machine readable indicia associated with the removed medical item using a scanner of the distribution machine (block 626). In response to the user scanning the machine readable indicia associated with the removed medical item, the processor receives the scanner input (block 628). The processor analyzes the scanner input as well as the item selection data to confirm that the correct item was removed by the user (block 630). The processor prompts the user to close the access door or the processor causes the door mechanism associated with the access door to close and lock the access door (block 632). An example of this is described above in connection with the latching mechanism 150 shown in FIGS. 11A through 11C.

In response to the user scanning the removed item and the access door being closed, the processor analyzes the storage location using a sensor of the distribution machine to verify that the medical item was removed from the storage location by the user (block 634). For example, an image may be captured by a camera 162 on the access door 30 directed towards the bin 74 defining the storage location to verify if an item is still present within the storage location. If the user selected more than one medical item for distribution, the operations described above may be repeated until all selected medical items are successfully distributed to the user (block 635). After distributing and verifying all selected medical items, the processor communicates data to a printer associated with the distribution machine such that a receipt is printed for the user (block 636). One or more records and/or databases may be updated following completion of the distribution (e.g., a transaction database, a user database, and/or corresponding location records) (block 638).

Figure 16:
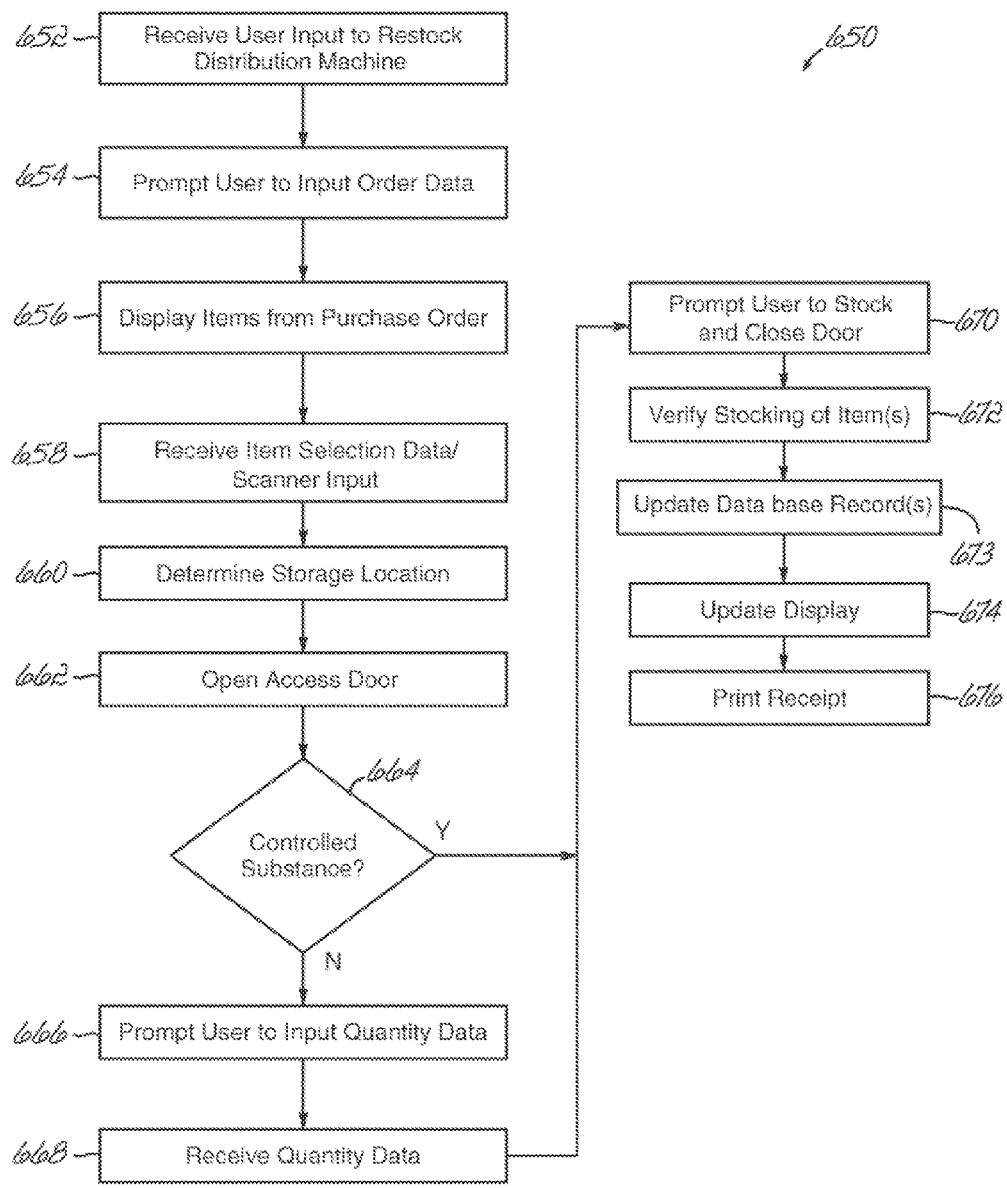
FIG. 16 is a flowchart illustrating a sequence of operations that may be performed by the distribution machine of FIG. 1 to facilitate restocking of the distribution machine.

FIG. 16 provides a flowchart 650 which illustrates a sequence of operations that may be performed by a distribution machine consistent with embodiments of the invention to restock medical items in the distribution machine. A user may log in to the distribution machine by entering user identification data into an HMI of the distribution machine. The user may input data indicating that the distribution machine is to be restocked, which is received by a processor of the distribution machine (block 652). The processor may output a prompt to the user through the HMI instructing the user to select and/or identify a purchase order associated with the restocking operation (block 654). In some embodiments, the user may scan machine readable indicia indicating a unique purchase order number using a scanner associated with the distribution machine. In some embodiments, the user may interact with a graphical user interface provided via the HMI to input a purchase order number or select a purchase order number from a displayed list of possible purchase order numbers, or the user may scan a radio frequency identification (RFID) tag or identification barcode associated with a medication delivery including the medical items of the purchase order using a scanner connected to the distribution machine. As discussed above with respect to FIG. 14, in some embodiments, the distribution machine may be connected to a transaction database storing one or more order records, where the order records may indicate the facility for which an order was placed, types and quantities of medical items purchased, a lot number for each medical item in the order, an expiration data for each medical item in the order and/or other such information. As such, the processor may match the input order data to a particular order record stored in a connected transaction database. The processor may display the medical items of the purchase order using the HMI (block 656) such that the user may select a medical item from the purchase order for stocking in the distribution machine, and the processor may receive the selection data from the HMI or the user may scan a barcode and/or RFID tag associated with a medical item of the purchase order to thereby input item selection data (block 658).

In response to receiving the item selection data for the medical item to be restocked, the processor determines a storage location that may store the type of medical item (block 660), and the processor actuates one or more of the drive mechanisms associated with a carousel including the storage location to position the storage location behind an access door. After positioning the storage location behind the access door, the processor causes a door mechanism associated with the access door to unlock and/or open the access door thereby providing access to the storage location to the user (block 662).

The processor determines whether the medical item to be stocked in the storage location is a controlled substance (block 664). As discussed above with respect to FIG. 15, some medical items may be government regulated, and the processor may access a medication record stored in a medication database to determine whether the medical item the user selected for stocking is a controlled substance. In some embodiments, if the medical item is a controlled substance, only 1 dose of the controlled substance will be stored in a storage location, while more than one other medical item that is not a controlled substance may be stored in a storage location. Therefore, in these embodiments, in response to determining that the selected medical item is not a controlled substance ("N" branch of block 664), the processor may output a prompt to the user through the HMI requesting the user to input a quantity of the medical item placed in the storage location (block 666), and the processor receives the quantity data input by the user via the HMI (block 668).

In response to determining that the medical item is a controlled substance ("Y" branch of block 664) or after receiving the quantity data, the processor prompts the user to place the medical item in the accessible storage location, and in some embodiments, the processor prompts the user to close the access door (block 670). In response to the access door being closed, the processor analyzes the storage location using information received from a sensor proximate the access door to determine whether the medical item was properly stocked in the storage location (block 672). For example, the image capturing, pixilation, and analyzing process described above in connection with FIGS. 12A and 12B could be used to confirm that enough pixels have changed to indicate the medical item has been stocked in the bin. In response to the medical item being stocked in the storage location, a location record stored in an accessible database corresponding to the storage location may be updated to include information from the order record associated with the purchase order (block 673). For example, the location record the location record may be updated to include various information for the medical item stocked in the storage location, including the name of the medical item, the dosage of the medical item, the expiration date of the medical item, the lot number of the medical item, and/or other such information. In response to determining that the item was properly stocked in the storage location, the display of medical items of the purchase order on the HMI may be updated to indicate that the selected medical item and/or quantity of the selected medical item has been stocked (block 674). A user may select another medical item of the purchase order displayed on the HMI and repeat the operations discussed above to restock other medical items of the purchase order. After the user has finished restocking all the medical items of the purchase order, the processor may output data to a printer associated with the distribution machine such that a receipt is printed for the user corresponding to the restocking performed by the user (block 676). It will be understood that the restocking of items in the distribution machine may be manually actuated when necessary or may be automatically initiated by reordering any medication or item that falls beneath a set threshold of doses located within the machine (e.g., automatic reordering when fewer than 3 doses remain).

Figure 17:
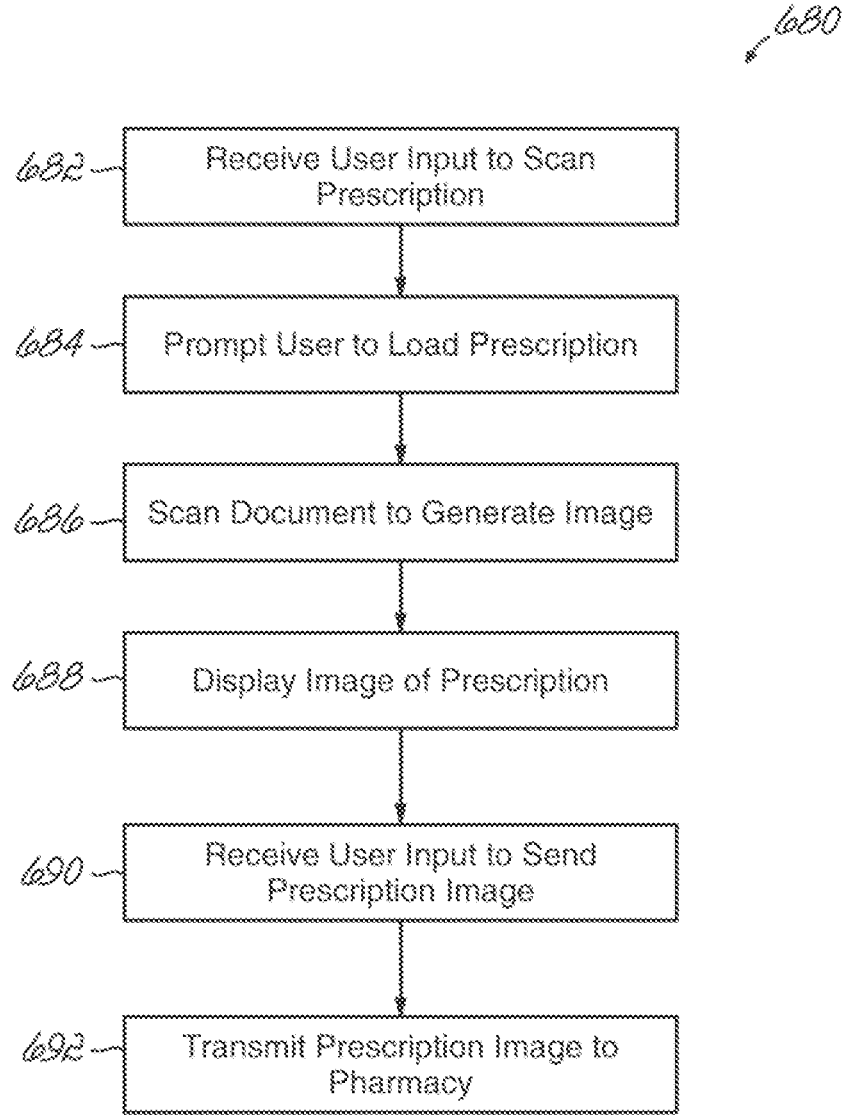
FIG. 17 is a flowchart illustrating a sequence of operations that may be performed by the distribution machine of FIG. 1 to transmit a prescription to an associated pharmacy.

FIG. 17 provides a flowchart 680 which illustrates a sequence of operations that may be performed by a distribution machine consistent with embodiments of the invention to transmit a prescription to an associated pharmacy. A user may interface with an HMI of the distribution machine to input data indicating that the user wishes to scan a prescription using a scanner in communication with the distribution machine (block 682). While in this exemplary embodiment a prescription is described as being scanned, other similar, equivalent, related and/or required documents may be scanned in a similar manner consistent with the invention. Moreover, it is understood that the prescription may be one or more documents and/or pages. Generally, the HMI will present the user with a graphical user interface (e.g., display screen 34), where the user may select an option presented on the graphical user interface to scan a prescription. Upon receiving such input data, a processor of the distribution machine may prompt the user via the graphical user interface to scan load/position the prescription in a proper scanning position for the scanner (e.g., document scanner 38) (block 684). The processor may receive input data from the user indicating that the prescription has been loaded, or the processor may receive an indication from a sensor associated with the scanner indicating that the prescription is loaded, and the processor may cause the scanner to scan the prescription to generate a digital image of the prescription (block 686). As discussed above, if the required documentation is more than one page, embodiments of the invention may generate a plurality of digital images. After scanning the prescription, the processor may cause the digital image of the prescription to be output on the HMI for the user's review (block 688), and the user may input a selection via the HMI confirming that the digital image should be transmitted to the pharmacy (block 690). The processor may transmit the digital image to the pharmacy over a communication network using a transceiver associated with the distribution machine (block 692).

In these embodiments of the invention, the distribution machine may advantageously transmit a digital image of a prescription to a pharmacy for review. In these embodiments, a medical item indicated on the prescription may be added to a patient's profile in a time efficient manner as compared to delivering the printed prescription. Furthermore, due to the expedited communication of the prescription to the associated pharmacy, the prescription may be reviewed quickly, and the pharmacy may update the patient's profile more quickly. Hence, in these embodiments, a user may add a medical item stored at the distribution machine to a patient's profile and thereby be able to distribute at least a dose of such medical item from the distribution machine in less time as compared to the conventional process of delivering the printed prescription to the pharmacy and waiting for the pharmacy to fill the prescription.

Figure 17A:
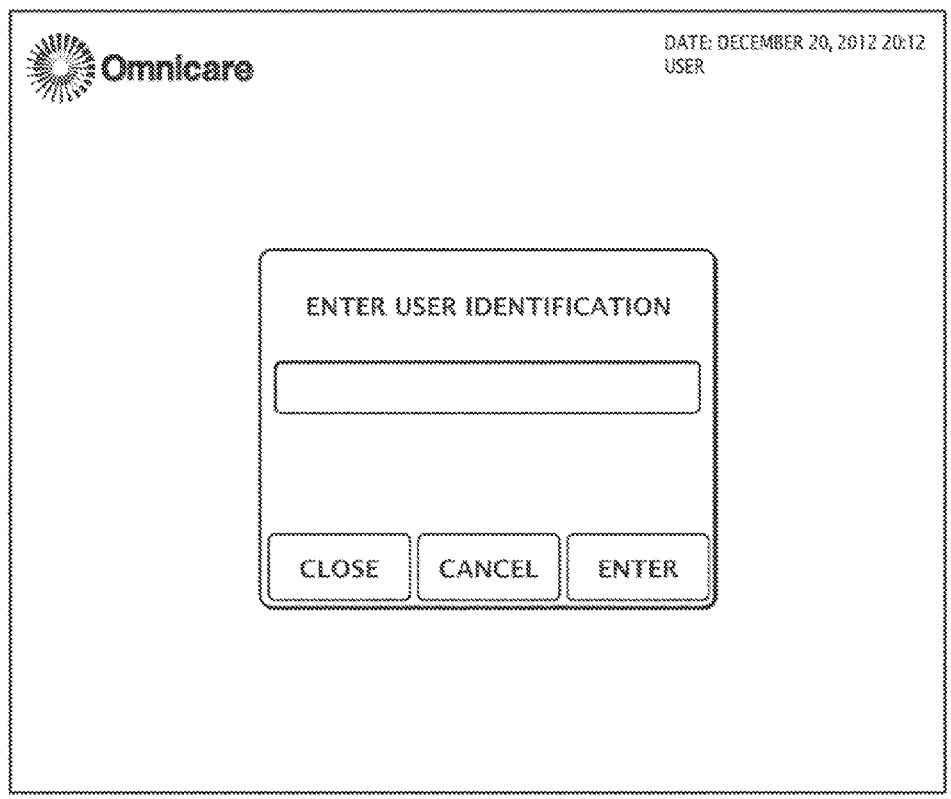
FIGS. 17A through 17T are exemplary output screens of a graphical user interface for the distribution machine of FIG. 1 that may be displayed to a user.
Figure 17B:
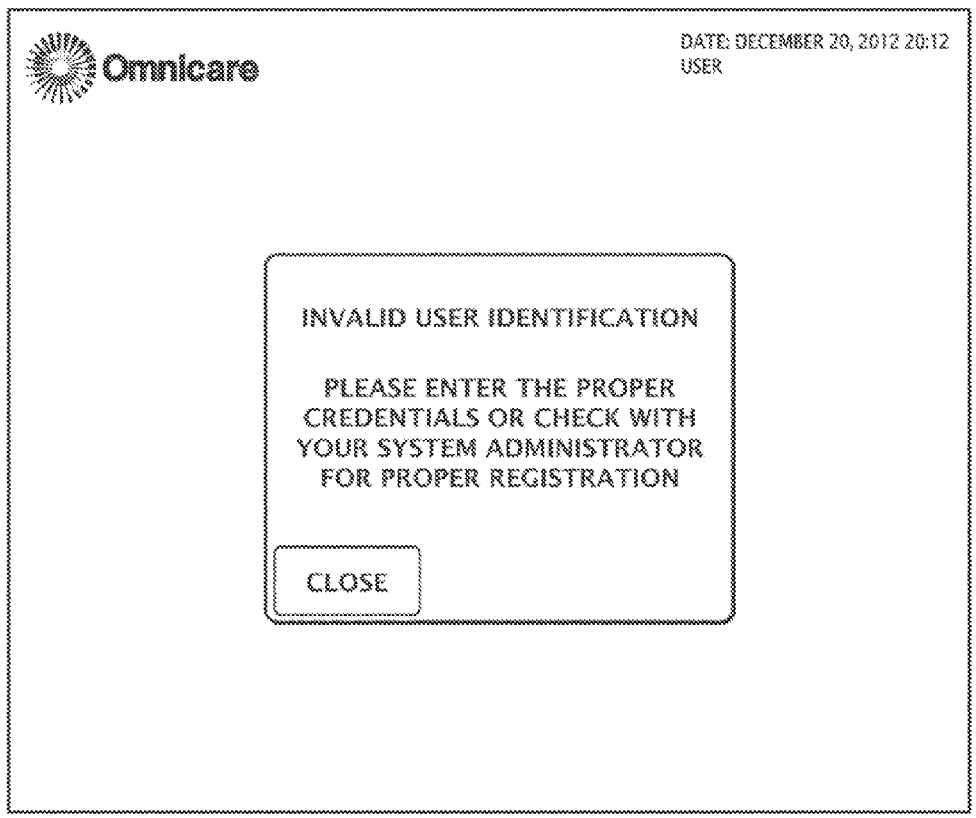
Figure 17C:
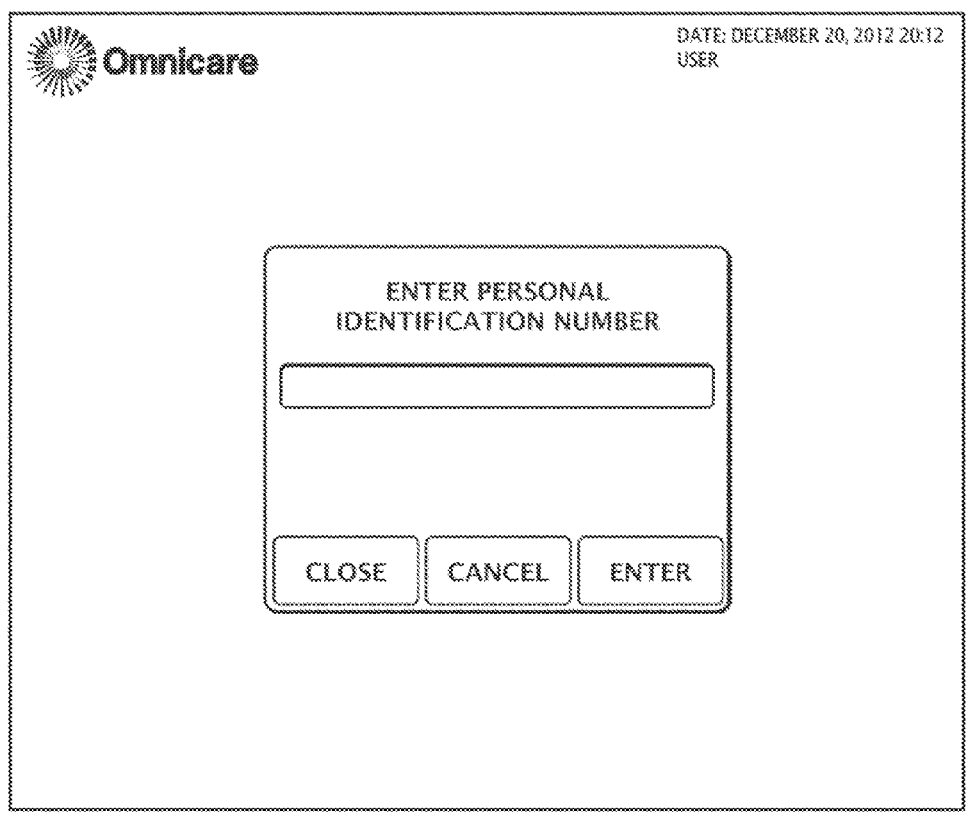
Figure 17D:
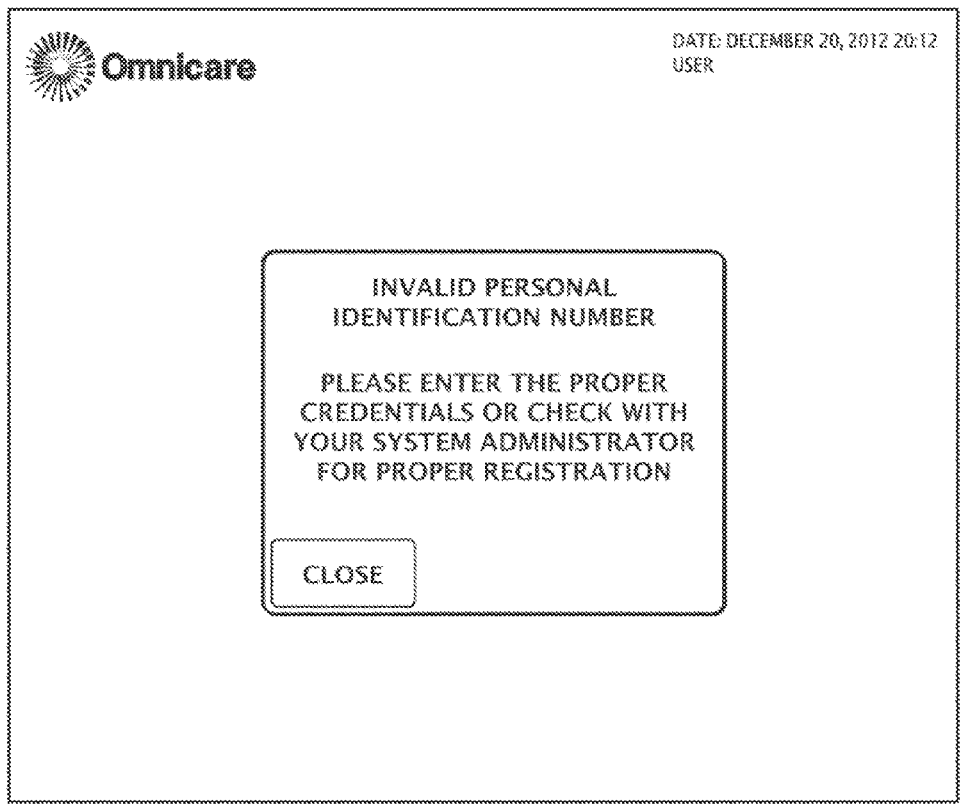
Figure 17E:
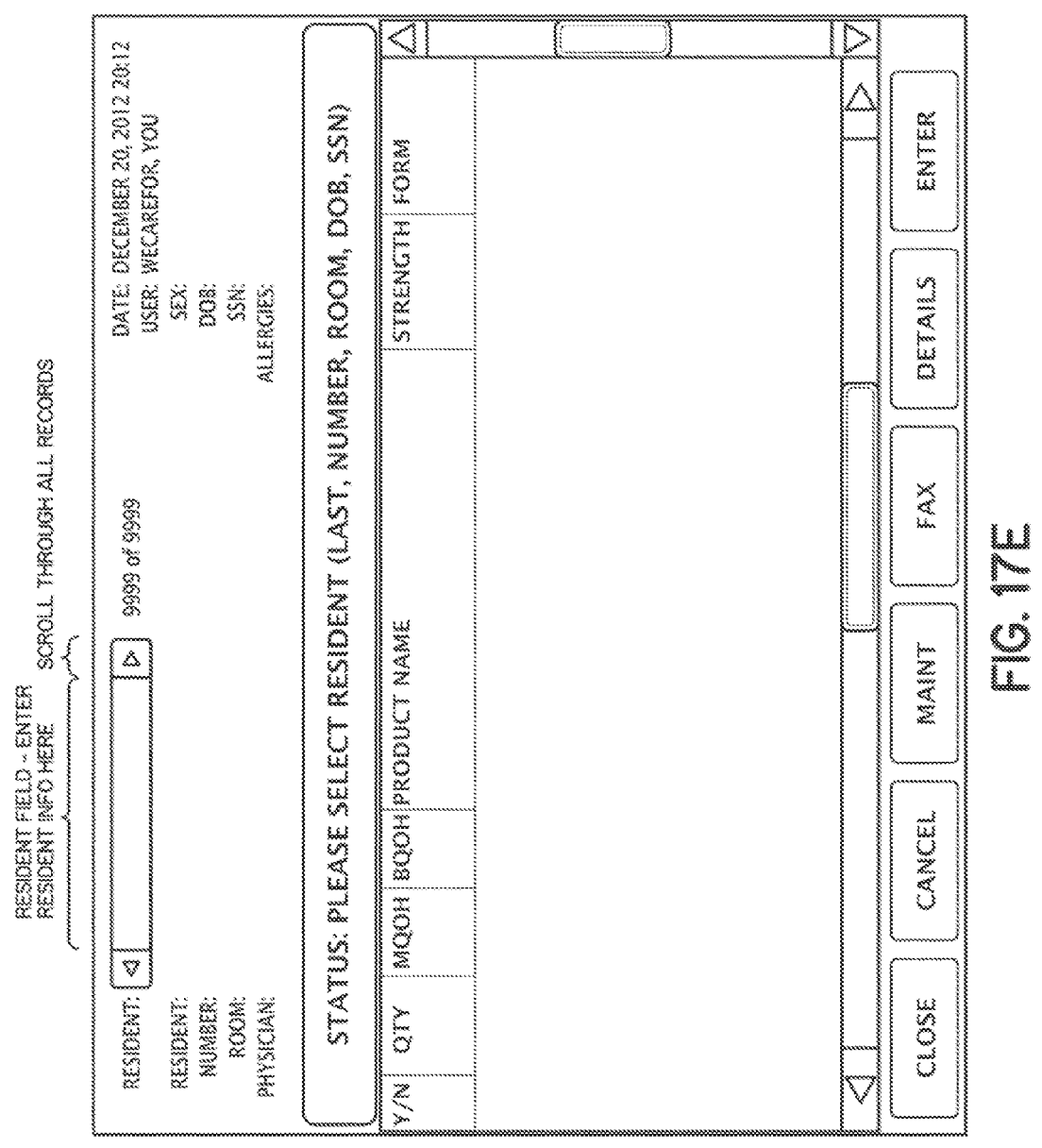
Figure 17G:
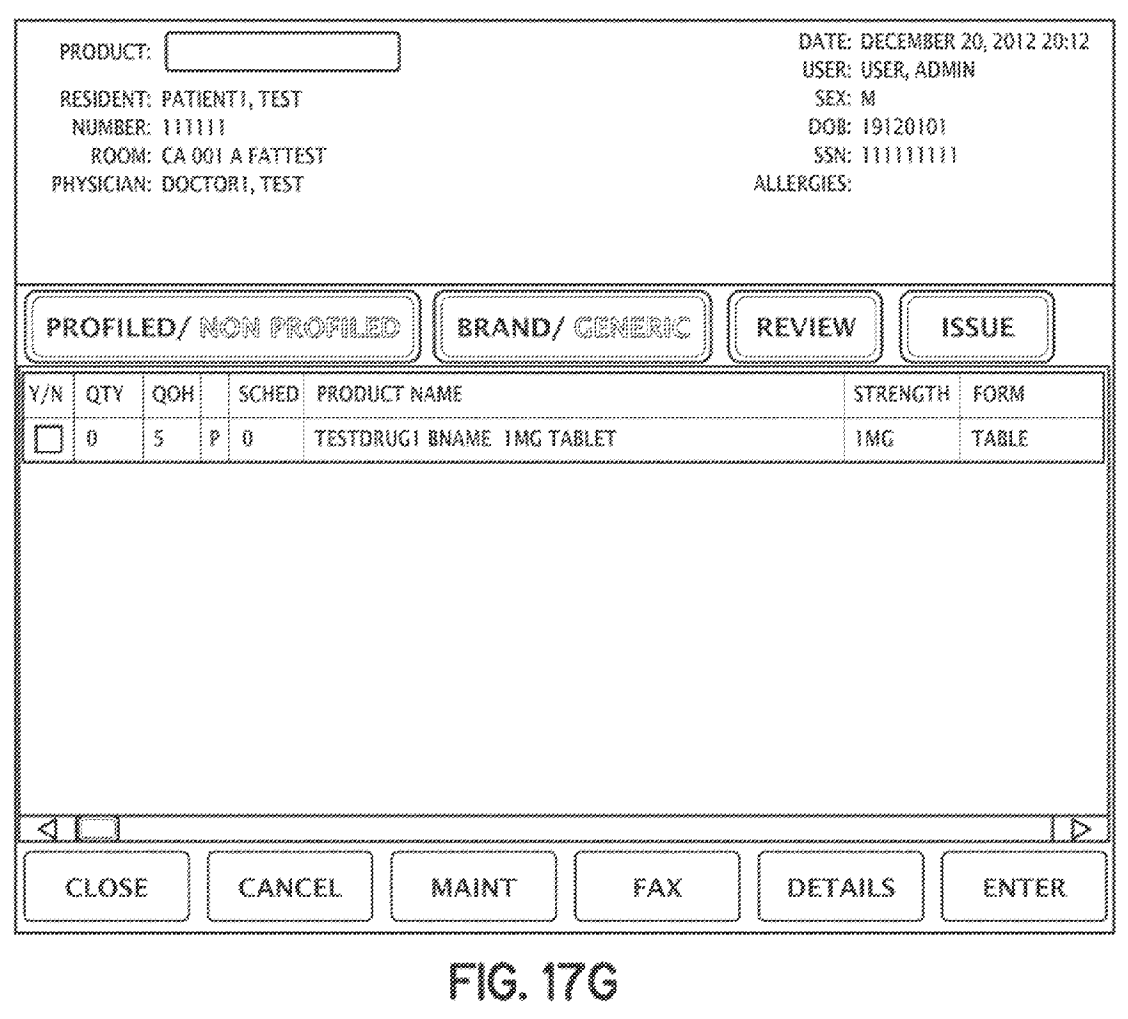
Figures 17K, 17L:
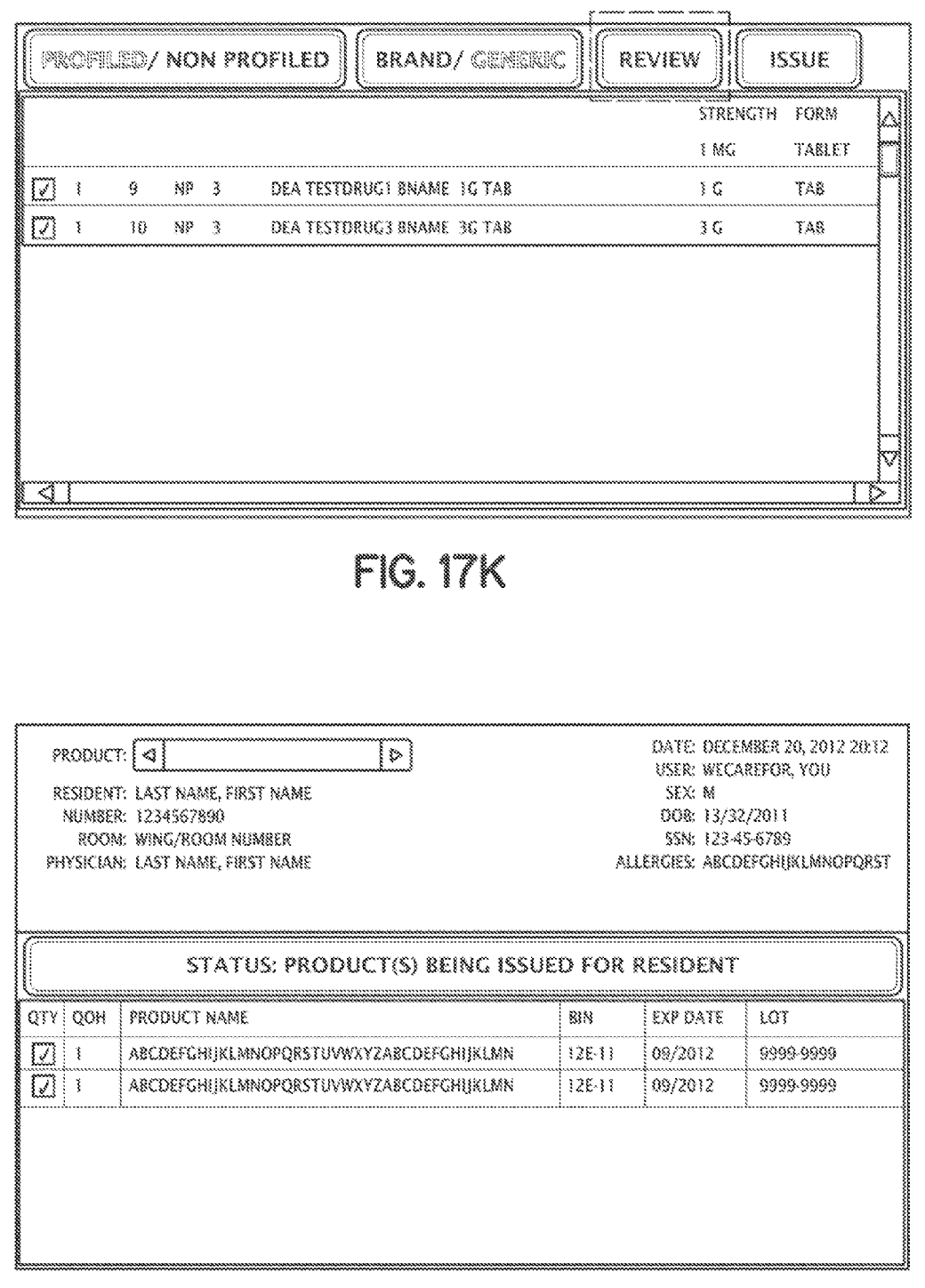
Figures 17M, 17N:
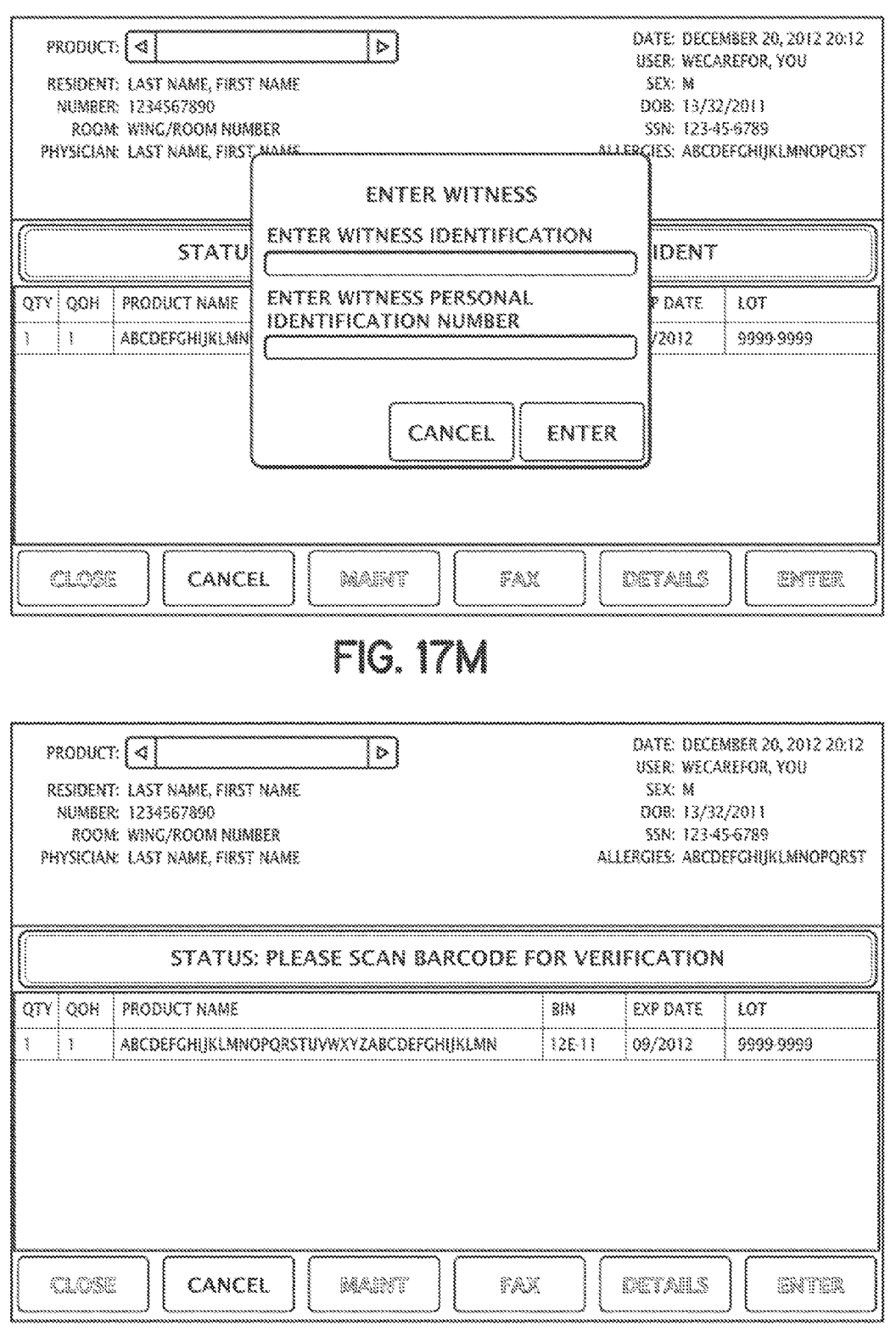

FIGS. 17A through 17T provide exemplary illustrations of information that may be output by a processor and displayed using an HMI of a distribution machine via a graphical user interface (e.g., display screen 34) consistent with embodiments of the invention. In FIG. 17A a log-in screen is provided that may be displayed or presented on the graphical user interface. In this exemplary embodiment, a user may input using the HMI a unique identification credential associated with the user (e.g., a unique code, a fingerprint scan, a retina scan, the last name of the user, etc.). As shown in FIG. 17B, in response to a user entering an incorrect/invalid identification credential (i.e., an identification code not associated with an authorized user), the processor may cause the HMI to output the error screen shown in FIG. 17B which informs the user that the identification credential input by the user is invalid. If a user inputs a valid/correct identification credential, as shown in FIG. 17C, the user may be prompted via the graphical user interface to input a personal identification number (PIN) associated with the user and the input identification credential. In response to the user entering an incorrect PIN, the processor may cause the HMI to display the error screen shown in FIG. 17D.

Following the user log-in shown in FIGS. 17A through 17D, the user may input identification data for a patient. FIG. 17E illustrates a display that may be presented to the user to identify a particular patient corresponding to the user's interaction with the distribution machine, where the user may input a name of the particular patient, a room number of the patient, a unique patient number, a date of birth of the patient, a social security number of the patient and/or any other such identifying characteristic for a particular patient. As shown in this example, the user may input only a portion of an identifying characteristic and a patient database may be searched for patient records matching the input portion. In response to the user inputting identification data for the particular patient, the processor may cause the HMI to output on the graphical user interface any patient records matching the input identification data. For example, FIG. 17F illustrates an output screen indicating a patient name, gender, date of birth, attending physician, room number, allergies, and patient number. As shown in FIG. 17F, if more than one patient record corresponds to the input identification data, the user may scroll through the patient records on the graphical user interface to select the patient record corresponding to the particular patient. In this example, the user may press the 'ENTER' button on the touch screen display shown to select the corresponding patient record.

As shown in FIG. 17G, the selected patient record may be shown, where the graphical user interface may include a list of prescribed medical items, the dosage of each prescribed medical item, the quantity on hand at the distribution machine for each prescribed medical item, the patient name, patient room number, attending physician, gender, date of birth, social security number and/or other such information stored in the patient record corresponding to the particular patient. With respect to the exemplary illustration shown in FIG. 17G, for each prescribed medical item, the graphical user interface may display information corresponding to the prescribed medical item. For example, a Yes/No (Y/N) checkbox may be associated with a prescribed medication, where the checkbox may be checked or un-checked by a user based on whether the prescribed medical item should be distributed. The graphical user interface may display a quantity (QTY) indicating the quantity to be distributed, a quantity on hand (QOH) which generally indicates the quantity available in the distribution machine, a machine quantity on hand (MQOH) indicating the total quantity of a medication in the distribution machine (generally used for controlled substances where only one medical item may be stocked in each bin), a bin quantity on hand (BQOH) (generally used for non-controlled substances where more than one medical item may be stocked in each bin), a profiled/not profiled (P/NP) indicating whether the medical item has been reviewed and placed on to the health record for a particular patient, a drug "class" (SCHED) indicating whether the medical item is a controlled substance and if so, which schedule, a product name, a strength (i.e., dosage), a dosage form (FORM) (e.g., tablet, liquid, etc.), dosing instructions and a unit dose pass time.

In some embodiments of the invention, the user may be able to interact with the graphical user interface to display additional information corresponding to the medical items stored in the distribution machine and/or information corresponding to the patient. For example, the distribution machine may be configured to distribute non-prescribed medical items, and as shown in FIG. 17H, the user has selected the 'NON PROFILED' button on the graphical user interface which displays a list of medical items stored in the distribution machine that are not prescribed to the particular patient. Furthermore, as shown in FIGS. 17I and 17J, the user may switch between the graphical user interface displaying the generic names of each medical item and the brand name of each medical item. The user may select the 'REVIEW' button to review medical items that have been selected for distribution, where the graphical user interface may display a screen such as the example shown in FIG. 17K. Pressing the 'ISSUE' button may initiate the distribution process previously discussed, and the graphical user interface may display a screen such as the example shown in FIG. 17L which generally displays the medical items that will be issued from the distribution machine.

Figure 17O:
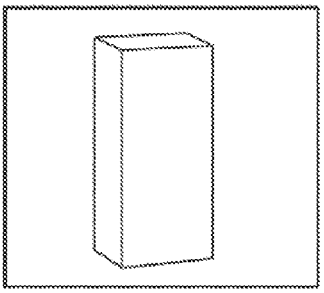

As described previously, in some embodiments, a distribution machine may store one or more controlled substances. In these embodiments, prior to issuing a controlled substance to a user, a witness may be prompted to input identification data. FIG. 17M provides an exemplary display output of an HMI of such distribution machine prompting a witness to enter identification criteria and a PIN. FIG. 17N provides an exemplary illustration of an HMI of a distribution machine prompting a user to scan machine readable indicia associated with a medical item removed from the distribution machine to verify that the correct type of medical item was removed. Referring to FIG. 17G, in some embodiments of the invention, a user may select a medical item from a displayed list of items and press the 'DETAILS' button to view additional details stored in a medication record corresponding to the medical item. FIG. 17O provides an exemplary illustration of an HMI of a distribution machine displaying such additional details, including for example an image of the medical item, the brand name, the generic name, the strength, dose, instructions, dosage times and/or other such information.

Figure 17P:
Figure 17Q:
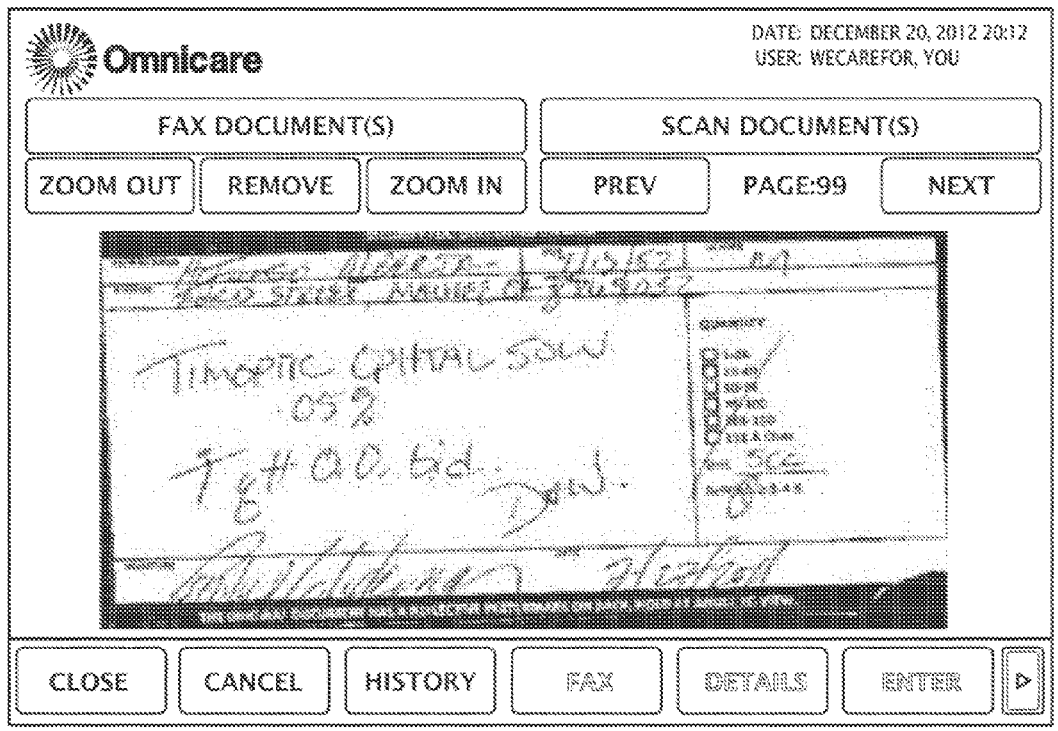

In a healthcare facility that may utilize a distribution machine consistent with some embodiments of the invention, a new patient may be in need of one or more medical items prior to a corresponding patient record being stored in the database. FIG. 17P provides an exemplary illustration of a graphical user interface of the distribution machine allowing a user to input patient information such that a temporary patient record may be used to distribute one or more medical items stored in the distribution machine. However, since the distribution machine may store medications requiring a prescription, if the user needs prescription medications for the patient, the user may be required to scan a prescription (including related and/or additional required paperwork) and transmit the prescription to an associated pharmacy for review prior to the distribution machine issuing such prescription medications. The input patient information comprises a temporary patient record which may be stored as a patient record in a patient database connected to the distribution machine and also communicated with a scanned prescription to the associated pharmacy. When the user is required to scan a prescription, the user may press the 'SCAN' button on the graphical user interface. FIG. 17Q provides an exemplary illustration of a processor of the distribution machine causing the HMI to output on the graphical user interface the scanned prescription.

Figures 17R, 17S:
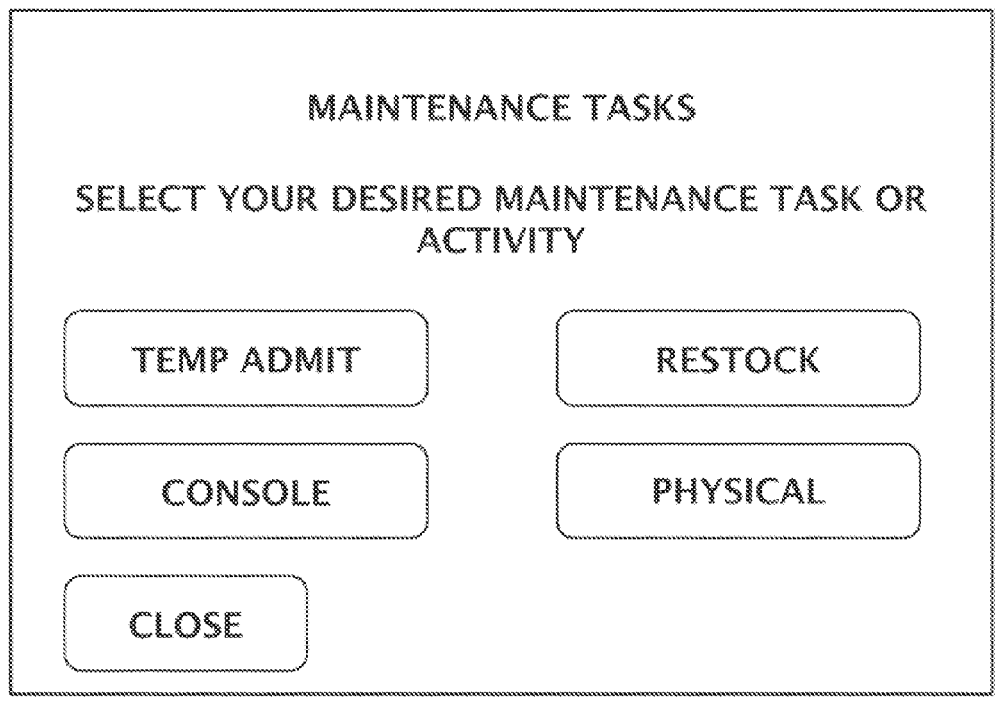
Figure 17T:
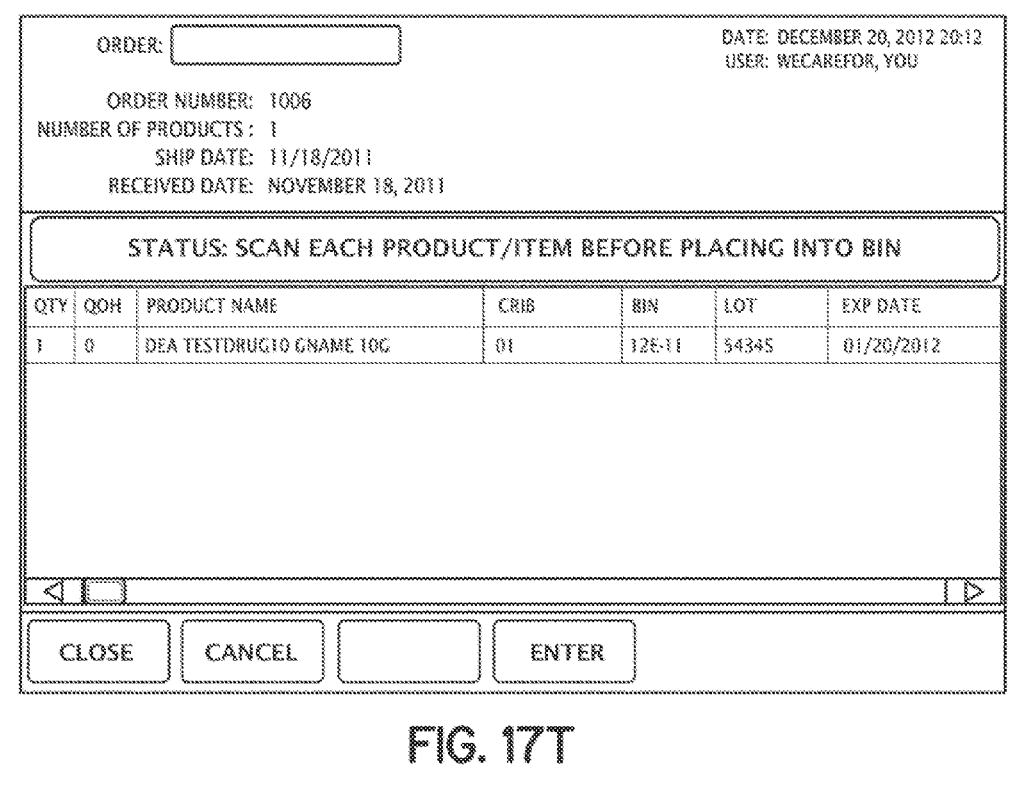

Referring to FIG. 17E, the 'MAINT' button allows a user to enter a maintenance menu of options for the distribution machine such as the exemplary maintenance options shown in FIG. 17R. In response to the user selecting the 'RESTOCK' button of FIG. 17R, the user is prompted to enter information corresponding to the restocking. For example, in FIG. 17S, the user is prompted to enter a shipping bag number associated with the medical items that are to be restocked. After identifying the purchase order associated with the restocking based on the input information the graphical user interface may be updated to display all medical items associated with the purchase order, as shown for example in FIG. 17T. The restocking process is then performed as described in detail above.

The distribution machine 10 and corresponding workflow methodologies described in connection with the current invention advantageously extend inventory supplies to remote healthcare facilities such as long-term care facilities, while still providing the necessary regulation and control of items like controlled substances. The distribution machine 10 can operate as a remote telepharmacy as well as an inventory supply for a first dose, a first day of doses, and/or multiple days of doses of medications that are required for potential new and existing patients. The distribution machine 10 quickly enables an authorized user to find a necessary medication or medical supply item and access that item, while maintaining a clear record including visual images that may be used to correct problems if an accidental or malicious diversion occurs. The ability to store up to 2100 separate unit doses of medication individually within a smaller device footprint (e.g., 36 inches by 39 inches) than conventional Automated Dispensing Cabinets will improve the applications in which the distribution machine 10 is useful.

Figure 18:
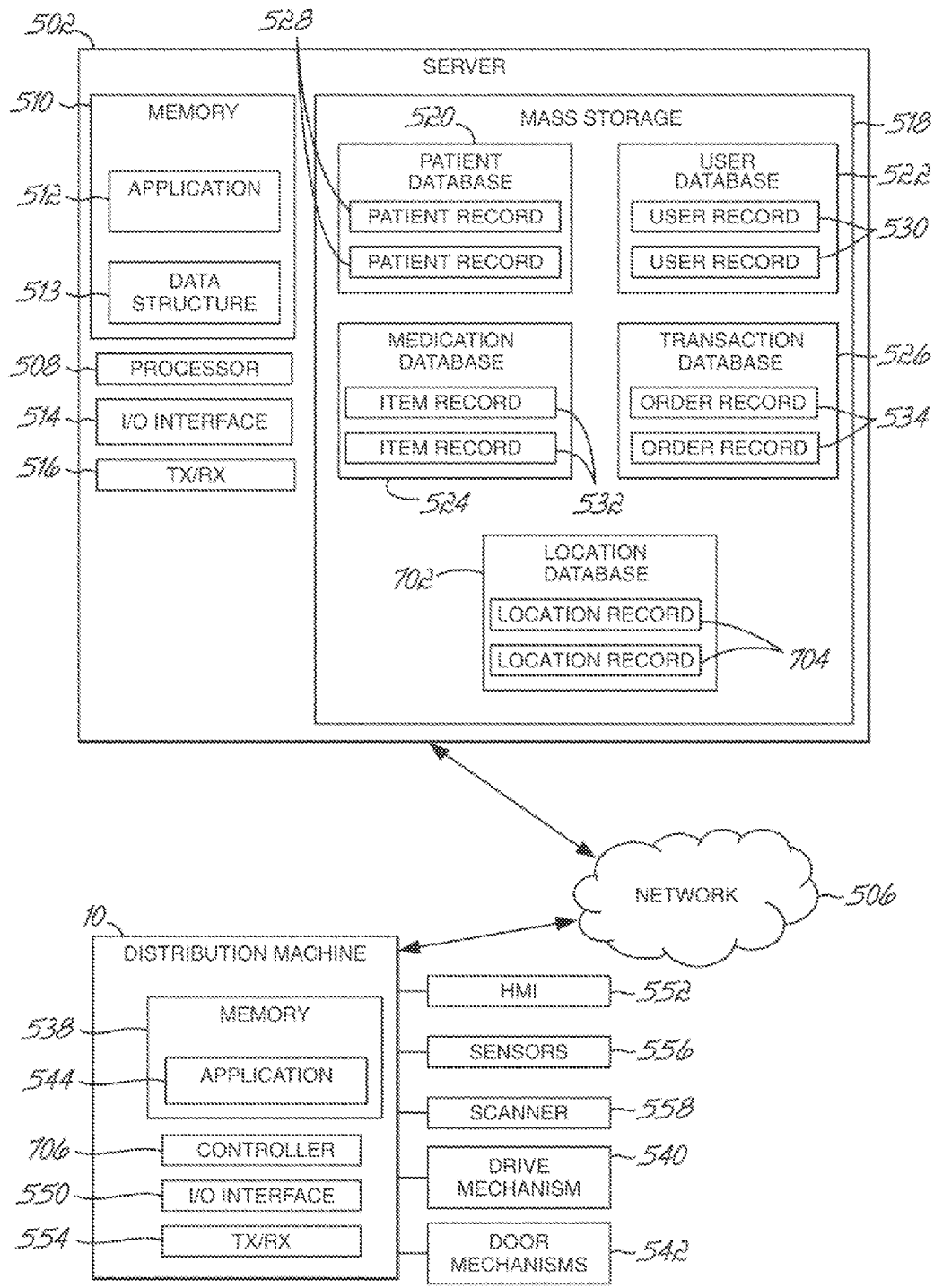
FIG. 18 is an exemplary block diagram of a system including the distribution machine of FIG. 1 and a server consistent with another embodiment of the invention.

FIG. 18 provides a block diagram illustrating a system including the medical information server 502 and the distribution machine 10. As described above with respect to FIG. 14, the medical information server 502 may be in communication with the distribution machine 10 over a communication network 506. While many of the components illustrated in FIG. 18 correspond to the components illustrated in FIG. 14, in this exemplary embodiment, the mass storage 518 of the server 502 includes a location database 702 including one or more location records 704. Each location record 704 includes information pertaining to a particular storage location of the distribution machine 10. Additionally, in this exemplary embodiment, the distribution machine 10 includes a machine controller 706 configured to execute application 544 stored in memory 538.

With respect to the embodiment of the distribution machine shown in FIG. 18, many operations described above with respect to FIGS. 14-17T may be performed at the server 502, where the distribution machine 10 functions as a remote terminal and all data is communicated over the communication network 506 to the server 502 for processing by the processor 508 of the server 502. The controller 706 of the distribution machine 10 executes application 544 to provide a remote interface with the server 502 such that a user may input data via the HMI 552 and the input data may be transmitted to the server 502 for processing by the server 502. The server 502 may communicate data to the distribution machine 10 and the controller 706 may process the data and perform one or more operations in response to processing the data. For example, the controller 706 may interface with the drive mechanism 540 and the door mechanisms 542 to position a storage location behind an access door and unlock an access door for distribution of a stored medical item.

Figure 19:
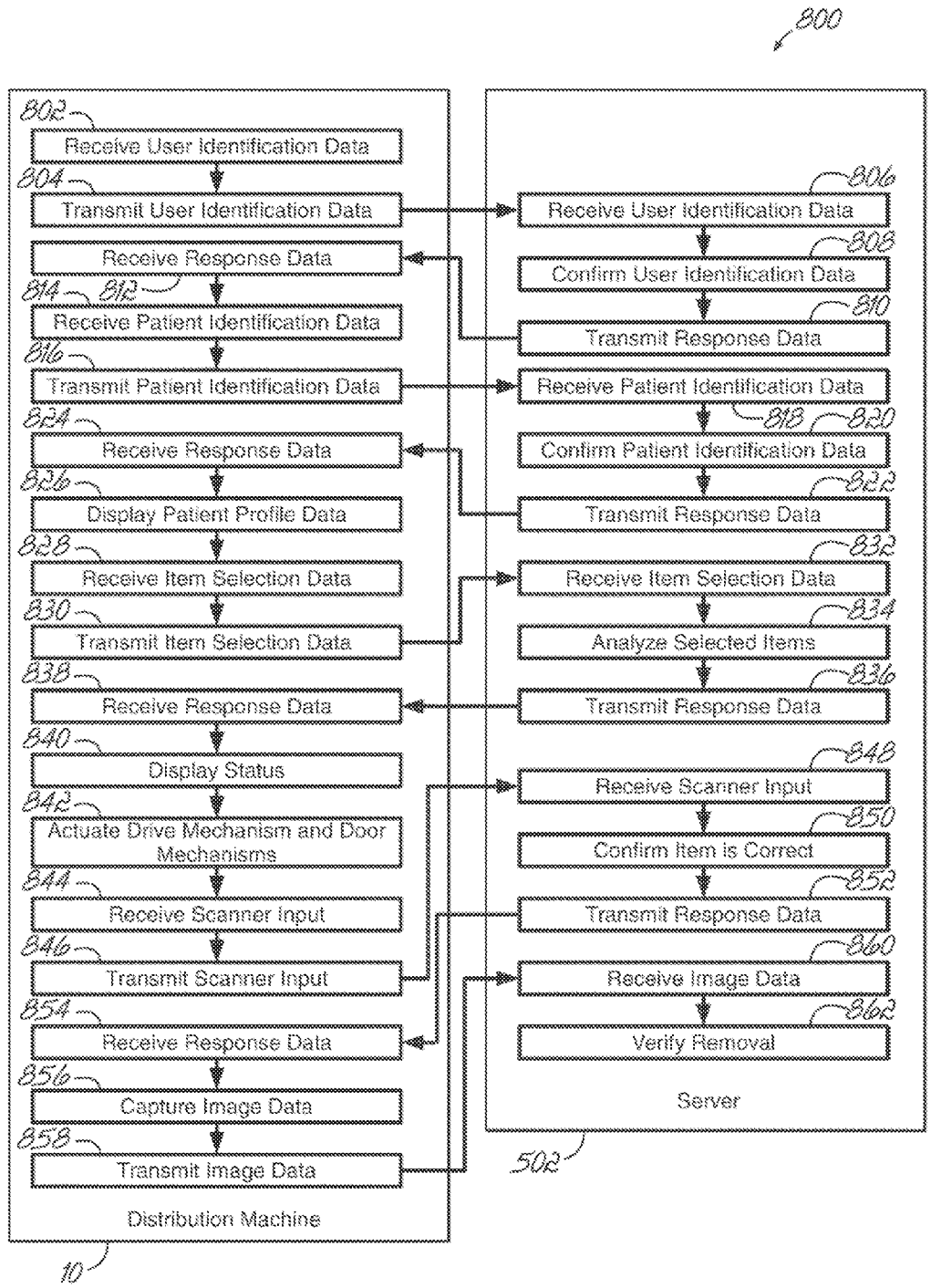
FIG. 19 is a flowchart illustrating a sequence of operations that may be performed by the distribution machine and server of FIG. 18 to distribute one or more medical items.

Turning now to FIG. 19, this figure provides a flowchart 800 illustrating a sequence of operations that may be performed by a distribution machine 10 and a server 502 consistent with some embodiments of the invention to distribute a stored medical item. As discussed above, in some embodiments the distribution machine 10 may serve as a remote interface to a server 502. For example, in some embodiments, the distribution machine 10 may display a secure Internet webpage which is connected to the server 502 such that a user may input information at the distribution machine 10 to the server 502 via the secure Internet webpage displayed by the distribution machine 1. An exemplary protocol that may be used to transfer encrypted data over the Internet is Hypertext Transfer Protocol with Secure Sockets Layer (HTTPS).

As such, a user may input user identification data via an HMI and a controller of the distribution machine 10 may receive the user identification data (block 802). The distribution machine 10 may communicate the user identification data to the server 502 for processing (blocks 804, 806). The server 502 analyzes the user identification data to confirm that the user identification data corresponds to a user record stored in a user database accessible by the server 502 (block 808). The server communicates response data to the distribution machine (blocks 810, 812). As mentioned, in embodiments of the invention where the distribution machine 10 displays a remote interface with the server 502, the response data from the server 502 may include the data loaded and displayed at the distribution machine 10. The user may input patient identification data via the HMI, and the controller of the distribution machine 10 may receive the patient identification data (block 814). The patient identification data is communicated to the server 502 from the distribution machine (blocks 816, 818). The server 502 analyzes the patient identification data to confirm that the patient identification data corresponds to a patient record stored in a patient database accessible to the server 502 (block 820). The server communicates response data to the distribution machine (blocks 822, 824); such that data from the corresponding patient record is displayed on a screen of the distribution machine 10 (block 826).

The user may select one or more medical items to be distributed for the patient, and the controller may receive the selection data from the HMI (block 828). The item selection data is communicated from the distribution machine 10 to the server 502 (blocks 830, 832). The server 502 analyzes the items selected and determines whether the user is authorized to receive the selected items, including for example, determining whether any selected items are controlled substances and whether the user is authorized to receive controlled substances (block 834). Furthermore, the server 502 analyzes the selected items to determine storage locations in the distribution machine storing the selected items by analyzing location records stored in a location database accessible by the server. Based on the selected items, the location records, and the user authorization level, the server 502 communicates response data to the distribution machine 10 (blocks 836, 838).

The response data may cause the machine controller to output display data to the HMI to inform the user of the status of the item selection request (block 840). In response to receiving the response data, the machine controller may actuate a drive mechanism of the distribution machine 10 to position a storage location storing a medical item selected by the user behind an access door for removal, and the machine controller may actuate a door mechanism to unlock and/or open the access door (block 842). The user may scan machine readable indicia associated with the medical item removed from the storage location using a scanner associated with the distribution machine 10, and the machine controller may receive the scanner input (block 844). The scanner input is communicated from the distribution machine 10 to the server 502 (blocks 846, 848).

The server 502 analyzes the scanner input to confirm that the correct medical item was distributed to the user (block 850). The server 502 communicates response data to the distribution machine (blocks 852, 854), where the response data indicates whether the correct medical item was distributed to the user. The distribution machine 10 captures image data corresponding to the storage location from which the medical item was removed using a camera associated with the distribution machine 10 (block 856), and the distribution machine communicates the image data to the server (blocks 858, 860). The server 502 analyzes the image data to determine whether the medical item was removed from the storage location (block 862).

As such, in this exemplary embodiment, the machine controller 706 of the distribution machine 10 executes an application to present the user with a remote interface with the server 502. The user may input data at the distribution machine 10 which may be communicated to the server 502 for processing. The server may transmit response data to the distribution machine which may cause the machine controller 706 of the distribution machine to perform one or more operations, including for example, updating a display, actuating a drive mechanism, actuating one or more door mechanisms, capturing image data with a camera of the distribution machine, and/or other such operations described herein.

Figure 20:
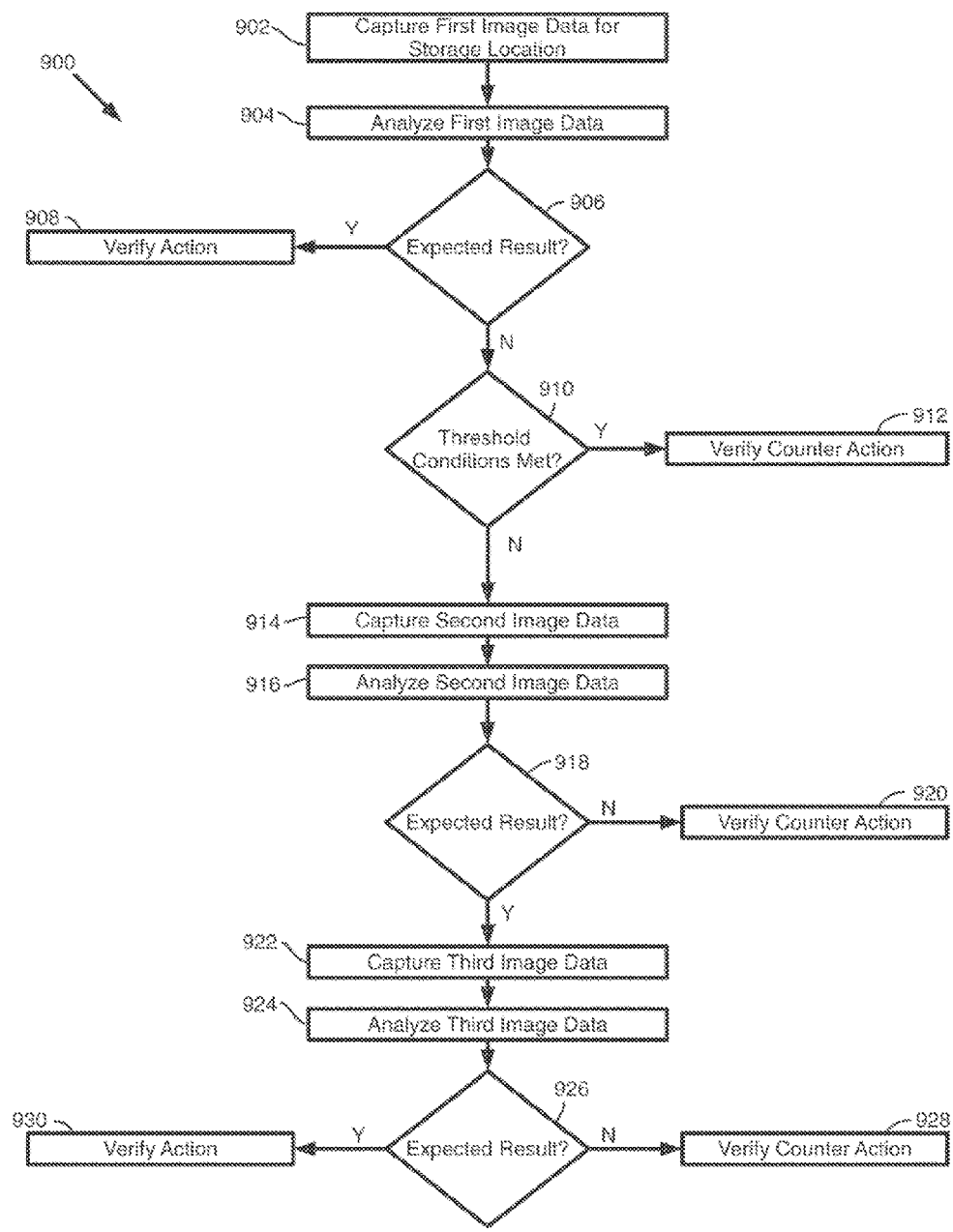
FIG. 20 is a flowchart illustrating a sequence of operations that may be performed by the distribution machine of FIG. 1 to verify stocking and/or removal of a medical item in the distribution machine.

FIG. 20 provides a flowchart 900 which illustrates a sequence of operations that may be performed by a distribution machine consistent with embodiments of the invention to verify whether a medical item was stocked and/or removed from a storage location by analyzing image data consistent with embodiments of the invention. As described previously, a camera may be utilized to capture image data of a storage location prior to and/or after a distribution or stocking of a medical item in the storage location. A processor of the distribution machine may cause the camera to capture a first image data for the storage location after a user indicates that an action has been performed (e.g., removal of a medical item or stocking of a medical item) (block 902). The processor may analyze the first image data (block 904), including, for example, digitizing the first image data, pixilating the first image data and performing pixel count analysis to determine a change of state for one or more pixels from a value of one to zero or vice versa from zero to one (block 904). The processor may determine whether the analysis indicates that the expected result has occurred (block 906). For example, if the medical item was supposed to be removed, the analysis would indicate that the storage location is empty. Similarly, if the medical item was supposed to be stocked, the analysis would indicate that the storage location includes the medical item.

In response to determining that the analysis indicates that the expected result occurred ("Y" branch of block 906), the action may be verified by the process (block 908). For example, the processor may output data indicating that the storage location is empty and/or contains the medical item. In response to determining that the analysis indicates that the expected result did not occur ("N" branch of block 906), the processor may determine whether threshold conditions in the image data were met (block 910). Threshold conditions may include, for example a percentage of an area of interest defined for the storage location that is different from the rest of the area of interest. In another example, a threshold condition may include a percentage of color change for pixels of an area of interest defined for the storage location. Other such threshold conditions may be defined for determining whether a medical item is present in a storage location based on image data for the storage location. In response to determining that the threshold conditions are met ("Y" branch of block 910), the processor may verify that the counter action to the expected action was performed (block 912). For example, if the expected action was to stock a medical item, the counter action would be that the analysis indicated that the storage location was empty.

In response to determining that the threshold conditions were not met ("N" branch of block 910), the processor may cause the camera to capture second image data for the storage location (block 914) and the processor may analyze the second image data (block 916). Hence in embodiments of the invention, in the event that the threshold conditions for the first image data are not met, to reduce the possibility of a false positive from image data not meeting threshold conditions, second image data may be captured and analyzed. The processor may determine whether the analysis indicates that the expected result has occurred (block 918). In response to determining that the expected result has not occurred ("N" branch of block 918), the processor may verify the counter action (block 920). As such, by determining twice that the expected result did not occur, the processor may determine, even with image data not meeting threshold conditions, which the expected result did not occur.

In response to determining that the expected result did occur based on the second image data ("Y" branch of block 918), the processor may cause the camera to capture third image data for the storage location (block 922), and the processor may analyze the third image data (block 924). In response to the analysis indicating that the expected result occurred ("Y" branch of block 926), the processor may verify the action (block 930). In response to the analysis indicating that the expected result did not occur, the processor may output data indicating that the expected action did not occur (block 928). Hence, in embodiments of the invention, the processor may analyze three sets of captured image data to determine whether a medical item was properly stocked or removed from a storage location if after a first inspection the opposite of the expected result is indicated or if the threshold conditions are not met for the first image data.

A plurality of distribution machines connected to a server consistent with embodiments of the invention may facilitate determining a quantity of each medical item on hand for a facility including the plurality of distribution machines distributed locally and/or remotely. Furthermore, in such a facility, a patient may be associated with a particular distribution machine of the based on a location indicated in a patient record corresponding to the patient. In response to the patient being moved to a different location, the patient may be associated with a different distribution machine. In these embodiments, particular medical items prescribed to the particular patient may be stocked in the different distribution machines based on the patient's location. For example, if a patient were to be in a first area with a first distribution machine for the first five days after being admitted to the facility, the first distribution machine may be stocked with the appropriate medical items for the first five days. If the patient is moved to a second location with a second distribution machine after the first five days, the second distribution machine may be stocked accordingly, where the ordering and stocking of the appropriate medical items at the first and second distribution machines may be based on the patient record and any particular rules for the facility stored in a database connected to the server and the distribution machines.

References herein to directional terms such as "vertical", "horizontal", "upper", "lower", "raise", "lower", etc. are made by way of example, and not by way of limitation, to establish a frame of reference. It is understood by persons of ordinary skill in the art that various other frames of reference may be equivalently employed for purposes of describing the embodiments of the invention.

It will be understood that when an element is described as being "attached", "connected", or "coupled" to or with another element, the element can be directly connected or coupled to the other element or, instead, one or more intervening elements may be present. In contrast, when an element is described as being "directly attached", "directly connected", or "directly coupled" to another element, there are no intervening elements present. When an element is described as being "indirectly attached", "indirectly connected", or "indirectly coupled" to another element, there is at least one intervening element present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising."

While the invention has been illustrated by a description of various embodiments and while these embodiments have been described in considerable detail, it is not the intention of the applicants to restrict or in any way limit the scope of the appended claims to such detail. In particular, any of the blocks of the above flowcharts may be deleted, augmented, made to be simultaneous with another, combined, or be otherwise altered in accordance with the principles of the invention. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicants' general inventive concept.

What is claimed is:

1. A method for selectively distributing a plurality of medical items stored in a secure access distribution machine including a housing enclosing a plurality of bins behind at least one access door and a controller with a processor and a memory, the method comprising:
    receiving first identification data associated with a user from an input device located at the distribution machine;
    in response to receiving the first identification data, comparing with the processor the first identification data with information stored in the memory to confirm that the user is authorized to distribute medical items from the distribution machine;
    receiving second identification data associated with a patient from the input device;
    in response to receiving the second identification data, displaying a patient record stored in the memory and associated with the patient on a display located at the distribution machine, the patient record including a list of medical items previously prescribed or approved for distribution to the patient;
    receiving item selection data from the input device that identifies, from the list of medical items previously prescribed or approved, at least one medical item that is selected for distribution to the user and administration to the patient;
    in response to receiving the item selection data, distributing a first medical item identified in the item selection data by rotating a bin holding the first medical item to a position behind a corresponding one of the access doors and unlocking the corresponding access door so that the access door opens and provides access for the user to reach into the bin to manually retrieve the first medical item from the bin;
    verifying with the processor that the user received the first medical item that was identified in the item selection data after the first medical item has been manually retrieved from the bin;
    repeating the distributing and verifying steps for each other medical item identified in the item selection data such that the user is provided access to the at least one medical item individually on an bin-by-bin basis; and
    updating the patient record to assign to the patient the at least one medical item that has been distributed to the user for administration to the patient,
    wherein the plurality of bins is mounted on a plurality of carousels mounted on carousel drive axles collectively centered at a central drive axle, and distributing the first medical item to the user further comprises:
    rotating all of the plurality of carousels around the central drive axle with a first motor to move the carousel having the bin holding the first medical item to a position adjacent the access door; and
    rotating each of the plurality of carousels simultaneously around their carousel drive axles with a second motor to move the bin holding the first medical item into the position behind the corresponding access door.

2. The method of claim 1, wherein the distribution machine includes a plurality of access doors stacked on top of each other in the housing, and distributing the first medical item to the user further comprises:
    blocking access to all bins within the housing except for the bin holding the first medical item by keeping all of the plurality of access doors locked and closed except for the corresponding access door, thereby limiting the user to manual retrieval of only the first medical item.

3. The method of claim 2, wherein at least some of the access doors include stationary blocking baffles rigidly mounted to the housing adjacent to the access door so as to reduce the size of an opening provided into the housing when the access door is opened, and blocking access to all bins except for the bin holding the first medical item further comprises:
    blocking manual access to bins located adjacent to the bin holding the first medical item with the stationary blocking baffles.

4. The method of claim 1, wherein verifying that the user received the first medical item further comprises:
    in response to manually retrieving the first medical item from the bin, prompting the user to scan a machine readable indicia associated with the first medical item with a scanner;
    receiving output from the scanner at the processor; and
    determining with the processor whether the first medical item that has been scanned matches the item selection data.

5. The method of claim 4, wherein the housing also includes a return receptacle with a one-way door providing access to insert, but not remove, rejected medical items, and the method further comprises:
    prompting the user to insert the first medical item into the return receptacle when the first medical item is not determined to match the item selection data or when the distribution process is interrupted.

6. The method of claim 4, wherein the access door further includes a camera, and verifying that the user received the first medical item further comprises:
: capturing image data using the camera, wherein the image data corresponds to the bin that was holding the first medical item; and
: analyzing the image data with the processor to confirm whether the first medical item has been removed from the bin.

7. The method of claim 6, wherein analyzing the image data with the processor further comprises:
: retrieving from the memory a stored pixilated digital image associated with the bin holding the first medical item, the stored pixilated digital image having been taken when the first medical item was placed into the bin; and
: comparing the captured image data with the stored pixilated digital image to determine whether enough pixels have changed to verify the removal of the first medical item from the bin.

8. The method of claim 6, wherein a plurality of the bins enclosed in the housing may be rotated into position adjacent to the camera, and the method further comprises:
: capturing a digital image of each bin that can rotate to a position adjacent to the camera while the housing and access door is closed; and
: storing each of the captured digital images in memory for use in later verification that a first medical item has been removed from one of the bins.

9. The method of claim 1, further comprising:
: prior to distributing the first medical item to the user:
:: determining with the processor whether the first medical item is a controlled sub stance;
:: if the first medical item is a controlled substance, determining with the processor whether the user is authorized to receive a controlled substance;
:: if the user is authorized to receive a controlled substance, prompting a witness to input third identification data via the input device;
:: in response to receiving the third identification data, determining with the processor whether the witness is authorized to witness distribution of a controlled substance; and
:: allowing the distribution of the first medical item to the user only if the user is authorized to receive a controlled substance and the witness is authorized to witness the distribution of a controlled substance.

10. The method of claim 1, further comprising:
: prior to distributing the first medical item to the user:
:: prompting a witness to input third identification data via the input device when any of the following conditions are satisfied:
::: (i) when the first medical item is a controlled substance;
::: (ii) when the first medical item exceeds a threshold schedule level;
::: (iii) when the first medical item is not on the list of medical items in the patient record; or
::: (iv) when a distribution is canceled during retrieval of the first medical item.

11. The method of claim 1, wherein at least some of the plurality of bins contain a plurality of medical items that may be stored in multiples within a single bin, and verifying that the user received the first medical item further comprises:
: updating a bin record stored in memory for the bin holding the first medical item to decrement a "bin quantity on hand" variable stored in the memory by one.

12. The method of claim 1, wherein the distribution machine includes an outer camera mounted on the housing, and the method further comprises:
: capturing still or moving images of the user at the distribution machine with the outer camera during the receiving item selection data, distributing, and verifying steps; and
: storing the captured still or moving images with a transaction record in the memory when the patient record is updated.

13. The method of claim 1, wherein the distribution machine includes a document scanner, and the method further comprises:
: receiving a scanned image of a prescription document from the document scanner;
: in response to receiving the scanned image of the prescription document, transmitting the scanned image of the prescription document to a remote location for approval by a pharmacist; and
: updating the list of medical items in the patient record that have been approved for the patient to include any medical items on the prescription document after approval by the pharmacist.

14. The method of claim 1, further comprising:
: receiving additional item selection data from the input device that identifies a second medical item that is selected for distribution to the user and administration to the patient, the second medical item not being included in the list of medical items on the patient record; and
: in response to receiving the additional item selection data, distributing the second medical item identified in the item selection data to the user.

15. A secure access distribution machine for distributing a plurality of medical items, comprising:
: a housing enclosing an interior and including at least one access door and an input device;
: a plurality of carousels located within the interior, wherein each carousel includes a plurality of bins for storing the plurality of medical items;
: a drive mechanism configured to rotate each of the plurality of carousels such that each of the plurality of bins may be positioned adjacent to the at least one access door; and
: a controller including a processor and a memory, the controller operatively coupled to the access door, the input device, and the drive mechanism, and the controller configured to perform a series of operations to distribute medical items from the housing including (i) determining that an user is an authorized user permitted to distribute medical items, (ii) display a patient record stored in the memory, the patient record including a list of medical items previously prescribed or approved for distribution to the patient, (iii) receive item selection data which identifies from the list of medical items previously prescribed or approved a first medical item that is selected for distribution, (iv) identifying a bin holding the first medical item that is selected for distribution to the user from the list of pre-approved or prescribed medical items associated with a patient record, (v) actuating the drive mechanism to move the bin holding the first medical item to a position behind a corresponding access door, (vi) unlocking and opening the corresponding access door to enable the user to reach into the bin and manually retrieve the first medical item, (vii) verifying that the first medical item that was selected for distribution was removed by the user, and (viii) updating the patient record to assign to the patient the first medical item that has been distributed, wherein the plurality of carousels are mounted on carousel drive axles collectively centered at a central drive axle, and the drive mechanism further comprises:
- a first motor that rotates all of the plurality of carousels around the central drive axle in order to move the carousel having the bin holding the first medical item to a position adjacent the access door; and
- a second motor that rotates each of the plurality of carousels simultaneously around their carousel drive axles in order to move the bin holding the first medical item into the position behind the corresponding access door.

16. A method for selectively distributing a plurality of medical items stored in a secure access distribution machine including a housing enclosing a plurality of bins behind at least one access door and a controller with a processor and a memory, the method comprising:

receiving first identification data associated with a user from an input device located at the distribution machine;

in response to receiving the first identification data, comparing with the processor the first identification data with information stored in the memory to confirm that the user is authorized to distribute medical items from the distribution machine;

receiving second identification data associated with a patient from the input device;

in response to receiving the second identification data, displaying a patient record stored in the memory and associated with the patient on a display located at the distribution machine, the patient record including a list of medical items previously prescribed or approved for distribution to the patient;

receiving item selection data from the input device that identifies, from the list of medical items previously prescribed or approved, at least one medical item that is selected for distribution to the user and administration to the patient;

in response to receiving the item selection data, distributing a first medical item identified in the item selection data by rotating a bin holding the first medical item to a position behind a corresponding one of the access doors and unlocking the corresponding access door so that the access door opens and provides access for the user to reach into the bin to manually retrieve the first medical item from the bin;

verifying with the processor that the user received the first medical item that was identified in the item selection data after the first medical item has been manually retrieved from the bin;

repeating the distributing and verifying steps for each other medical item identified in the item selection data such that the user is provided access to the at least one medical item individually on an bin-by-bin basis;

updating the patient record to assign to the patient the at least one medical item that has been distributed to the user for administration to the patient; and during a restocking process for the distribution machine, receiving a scan of a machine readable indicia on a purchase or shipping order with a scanner located at the housing, the purchase or shipping order being associated with a plurality of medical items to be stocked inside the housing;

receiving a verification scan of machine readable indicia on a first item to be stocked;

rotating a first available bin configured to receive the first item to a position adjacent one of the access doors;

unlocking and opening the one of the access doors to provide the user access to manually place the first item in the first available bin;

locking the one of the access doors in a closed position when the one of the access doors is closed by the user;

capturing an image of the first available bin to verify the manual placement of the first item into the first available bin; and repeating the receiving a verification scan, rotating, opening, locking, and scanning steps for each other item associated with the purchase or shipping order.

17. The method of claim 16, wherein the restocking process further comprises:

in response to receiving the scan of the purchase or shipping order, automatically updating an inventory record stored in memory to include various information about each of the plurality of medical items to be stocked, including a lot number, an expiration date, a National Drug Code, and a UPC, thereby not requiring separate manual entry of these items of information for each of the plurality of medical items to be stocked.

* * * * *

UNITED STATES PATENT AND TRADEMARK OFFICE
CERTIFICATE OF CORRECTION

| | | |
|---|---|---|
| PATENT NO. | : 9,443,370 B2 | |
| APPLICATION NO. | : 13/801944 | |
| DATED | : September 13, 2016 | |
| INVENTOR(S) | : Bradley E. Carson et al. | |

It is certified that error appears in the above-identified patent and that said Letters Patent is hereby corrected as shown below:

In the Specification

In Column 1, Line 15, reads "and associated methods, and more particularly, to a distri-" should read -- and associated methods and, more particularly, to a distri- --

In Column 3, Line 22, reads "individually on an bin-by-bin basis. The patient record is" should read -- individually on a bin-by-bin basis. The patient record is --

In Column 4, Line 55, reads "medical items and items are individually scanned in and out" should read -- medical items and other items are individually scanned in and out --

In Column 6, Line 26, reads "configured to record still images or moving images of an" should read -- configured to record still images or moving images of a --

In Column 6, Line 30, reads "removal, or rejected or incorrect medical items from the" should read -- removal, of rejected or incorrect medical items from the --

In Column 9, Line 30, reads "ventional refrigeration unit 29 and its operation are not" should read -- ventional refrigeration unit 29 and its operation is not --

In Column 13, Line 2, reads "partial carousels 92 already is directed radially outwardly" should read -- partial carousels 92 already are directed radially outwardly --

In Column 13, Line 37, reads "interior 14 of the distribution machine 10 are minimized if" should read -- interior 14 of the distribution machine 10 is minimized if --

In Column 17, Line 3, reads "access door 30 adjacent the access door 30 adjacent the" should read -- access door 30 adjacent the --

Signed and Sealed this
Thirty-first Day of January, 2017

Michelle K. Lee
*Director of the United States Patent and Trademark Office*

CERTIFICATE OF CORRECTION (continued)

U.S. Pat. No. 9,443,370 B2

In Column 17, Line 50, reads "170 stores in the bins 128 may have common SKU." should read -- 170 stored in the bins 128 may have common SKU. --

In Column 18, Line 5, reads "some other similar motor that operates with withdraw the" should read -- some other similar motor that operates to withdraw the --

In Column 22, Line 25, reads "ond output gear 254 are located higher in elevation than the" should read -- ond output gear 254) are located higher in elevation than the --

In Column 27, Line 66, reads "age schedule, associated medical items allergies and/or other" should read -- age schedule, associated medical items, allergies and/or other --

In Column 31, Line 25, reads "location record the location record may be updated to" should read -- location record may be updated to --

In Column 38, Line 14, reads "conditions, which the expected result did not occur" should read -- conditions, which of the expected results did not occur --

In Column 38, Line 38, reads "bution machine of the based on a location indicated in a" should read -- bution machine based on a location indicated in a --

In the Claims

In Column 40, Line 14, Claim 1, reads "medical item individually on an bin-by-bin basis; and" should read -- medical item individually on a bin-by-bin basis; and --

In Column 41, Line 33, Claim 9, reads "cal item is a controlled sub stance;" should read -- cal item is a controlled substance; --

In Column 42, Line 54, Claim 15, reads "determining that an user is an authorized user permitted" should read -- determining that a user is an authorized user permitted --

In Column 44, Line 13, Claim 16, reads "medical item individually on an bin-by-bin basis;" should read -- medical item individually on a bin-by-bin basis; --